US006421612B1

(12) United States Patent
Agrafiotis et al.

(10) Patent No.: US 6,421,612 B1
(45) Date of Patent: Jul. 16, 2002

(54) SYSTEM, METHOD AND COMPUTER PROGRAM PRODUCT FOR IDENTIFYING CHEMICAL COMPOUNDS HAVING DESIRED PROPERTIES

(75) Inventors: Dimitris K. Agrafiotis, Downington, PA (US); Roger F. Bone, Bridgewater, NJ (US); Francis R. Salemme, Yardley, PA (US); Richard M. Soll, Lawrenceville, NJ (US)

(73) Assignee: 3-Dimensional Pharmaceuticals Inc., Exton, PA (US)

(*) Notice: Subject to any disclaimer, the term of this patent is extended or adjusted under 35 U.S.C. 154(b) by 0 days.

(21) Appl. No.: 08/963,870

(22) Filed: Nov. 4, 1997

Related U.S. Application Data

(60) Provisional application No. 60/030,187, filed on Nov. 4, 1996.

(51) Int. Cl.[7] .............................................. G06F 19/00

(52) U.S. Cl. ...................................................... 702/19

(58) Field of Search ............................................ 702/19

(56) References Cited

U.S. PATENT DOCUMENTS

| | | | |
|---|---|---|---|
| 4,773,099 A | 9/1988 | Bokser | 382/14 |
| 4,811,217 A | 3/1989 | Tokizane et al. | 364/300 |
| 4,859,736 A | 8/1989 | Rink | 525/54.1 |
| 4,908,773 A | 3/1990 | Pantoliano et al. | 364/496 |
| 4,935,875 A | 6/1990 | Shah et al. | 364/497 |
| 4,939,666 A | 7/1990 | Hardman | 436/89 |
| 5,010,175 A | 4/1991 | Rutter et al. | 530/334 |
| 5,025,388 A | 6/1991 | Cramer, III et al. | 364/496 |
| 5,155,801 A | 10/1992 | Lincoln | 395/22 |
| 5,167,009 A | 11/1992 | Skeirik | 395/27 |
| 5,181,259 A | 1/1993 | Rorvig | 382/36 |
| 5,240,680 A | 8/1993 | Zuckerman et al. | 422/67 |
| 5,260,882 A | 11/1993 | Blanco et al. | 364/499 |
| 5,265,030 A | 11/1993 | Skolnick et al. | 364/496 |
| 5,270,170 A | 12/1993 | Schatz et al. | 435/7.37 |
| 5,288,514 A | 2/1994 | Ellman | 427/2 |
| 5,307,287 A | 4/1994 | Cramer, III et al. | 364/496 |
| 5,323,471 A | 6/1994 | Hayashi | 382/15 |
| 5,331,573 A | 7/1994 | Balaji et al. | 364/500 |
| 5,434,796 A | 7/1995 | Weininger | 364/496 |
| 5,436,850 A | 7/1995 | Eisenberg et al. | 364/496 |
| 5,442,122 A | 8/1995 | Noda et al. | 564/426 |
| 5,463,564 A | 10/1995 | Agrafiotis et al. | 364/496 |
| 5,499,193 A | 3/1996 | Sugawara et al. | 364/500 |
| 5,519,635 A | 5/1996 | Miyake et al. | 364/497 |
| 5,524,065 A | 6/1996 | Yagasaki | 382/226 |
| 5,526,281 A | 6/1996 | Chapman et al. | 364/496 |
| 5,545,568 A | 8/1996 | Ellman | 436/518 |
| 5,549,974 A | 8/1996 | Holmes | 428/403 |
| 5,553,225 A | 9/1996 | Perry | 395/157 |
| 5,565,325 A | 10/1996 | Blake | 435/7.1 |
| 5,574,656 A | 11/1996 | Agrafiotis et al. | 364/500 |
| 5,585,277 A | 12/1996 | Bowie et al. | 436/518 |

(List continued on next page.)

FOREIGN PATENT DOCUMENTS

| | | | |
|---|---|---|---|
| EP | 0 355 266 B1 | 6/1993 | B01J/19/00 |
| EP | 0 770 876 A1 | 5/1997 | G01N/33/68 |
| EP | 0 818 744 A2 | 1/1998 | G06F/17/50 |
| WO | WO 91/19735 | 12/1991 | C07K/7/02 |
| WO | WO 92/00091 | 1/1992 | A61K/37/02 |
| WO | WO 93/20242 | 10/1993 | C12Q/1/70 |
| WO | WO 97/09342 | 3/1997 | C07H/21/02 |
| WO | WO 97/20952 | 6/1997 | C12Q/1/68 |

OTHER PUBLICATIONS

Andrea et al., "Applications of Neural Networks in QSARs of Dihydrofolate Reductase Inhibitors" J. Med. Chem. vol. 34, pp. 2824–2836, 1991.*

Loew et al., "Straefies for Indirect Computer Aided Drug Design" Pharmaceutical Research vol. 10, pp. 475–486, 1993.*

(List continued on next page.)

*Primary Examiner*—John S. Brusca
(74) *Attorney, Agent, or Firm*—Sterne, Kessler, Goldstein & Fox, P.L.L.C.

(57) ABSTRACT

An automatic, partially automatic, and/or manual iterative system, method and/or computer program product for generating chemical entities having desired or specified physical, chemical, functional, and/or bioactive properties. The present invention identifies a set of compounds for analysis; collects, acquires or synthesizes the identified compounds; analyzes the compounds to determine one or more physical, chemical and/or bioactive properties (structure-property data); and uses the structure-property data to identify another set of compounds for analysis in the next iteration. An Experiment Planner generates Selection Criteria and/or one or more Objective Functions for use by a Selector. The Selector searches the Compound Library to identify a subset of compounds (a Directed Diversity Library) that maximizes or minimizes the Objective Functions. The compounds listed in the Directed Diversity Library are then collected, acquired or synthesized, and are analyzed to evaluate their properties of interest. In one embodiment, when a compound in a Directed Diversity Library is available in a Chemical Inventory, the compound is retrieved from the Chemical Inventory instead of re-synthesizing the compound. The Analysis Module receives the compounds of the Directed Diversity Library from the Chemical Inventory and/or the Synthesis Module, analyzes the compounds and outputs Structure-Property data. The Structure-Property data is provided to the Experiment Planner and is also stored in the Structure-Property database. The Experiment Planner defines one or more new Selection Criteria and/or Objective Functions for the next iteration of the invention. In one embodiment, a Structure-Property Model Generator generates Structure-Property Models and provides them to the Experiment Planner which uses the Models to generate subsequent Selection Criteria and/or Objective Function.

42 Claims, 19 Drawing Sheets

U.S. PATENT DOCUMENTS

| | | | |
|---|---|---|---|
| 5,602,755 A | 2/1997 | Ashe et al. | 364/498 |
| 5,602,938 A | 2/1997 | Akiyama et al. | 382/155 |
| 5,612,895 A | 3/1997 | Balaji et al. | 364/496 |
| 5,634,017 A | 5/1997 | Mohanty et al. | 395/326 |
| 5,635,598 A | 6/1997 | Lebl et al. | 530/334 |
| 5,670,326 A | 9/1997 | Beutel | 435/7.1 |
| 5,679,582 A | 10/1997 | Bowie et al. | 436/518 |
| 5,684,711 A | 11/1997 | Agrafiotis et al. | 364/500 |
| 5,703,792 A | 12/1997 | Chapman | 364/496 |
| 5,712,171 A | 1/1998 | Zambias et al. | 436/518 |
| 5,712,564 A | 1/1998 | Hayosh | 324/210 |
| 5,736,412 A | 4/1998 | Zambias et al. | 436/518 |
| 5,740,326 A | 4/1998 | Boulet et al. | 395/27 |
| 5,789,160 A | 8/1998 | Eaton et al. | 435/6 |
| 5,807,754 A | 9/1998 | Zambias et al. | 436/518 |
| 5,811,241 A | 9/1998 | Goodfellow et al. | 435/7.1 |
| 5,832,494 A | 11/1998 | Egger et al. | 707/102 |
| 5,858,660 A | 1/1999 | Eaton et al. | 435/6 |
| 5,861,532 A | 1/1999 | Brown et al. | 564/142 |
| 5,866,334 A | 2/1999 | Beutel | 435/6 |
| 5,901,069 A | 5/1999 | Agrafiotis et al. | 364/528.03 |
| 5,908,960 A | 6/1999 | Newlander | 564/177 |
| 5,933,819 A | 8/1999 | Skolnick et al. | 706/21 |
| 6,014,661 A | 1/2000 | Ahlberg et al. | 707/3 |
| 6,037,135 A | 3/2000 | Kubo et al. | 435/7.24 |
| 6,049,797 A | 4/2000 | Guha et al. | 707/6 |

OTHER PUBLICATIONS

Guez et al., "Neural etworks and fuzzy logic in clinical laboratory computing with applications to integrated monitoring" Clinica Chimica Acta, vol. 248, pp. 73–90, 1996.*

"Similarity in Chemistry Past Present Future" Topics in Current Chemistry, vol. 173, pp. 1–30, 1995.*

Gasteiger et al., "Analysis of the Reactivity of Single Bonds in Aliphatic Molecules by Statistical and Pattern Recognition Methods" J. Chem. Inf. Comput. Sci. vol. 33, pp. 385–394, 1993.*

Agrafiotis, D.K., "A New Method For Analyzing Protein Sequence Relationships Based On Sammon Maps," Protein Science, vol. 6, No. 2, Feb. 1997, pp. 287–293.

International Search Report for Appl. No. PCT/US99/09963, 7 pages.

Grayhill, T.L. et al., "Enhancing the Drug Discovery Process by Integration of High–Throughput Chemistry and Structure–Based Drug Design," from Molecular Diversity and Combinatorial Chemistry: Libraries and Drug Discovery, Chaiken and Janda (eds.), American Chemical Society, 1996, pp. 16–27.

Saund, E., "Dimensionality–Reduction Using Connectionist Networks," IEEE Transactions on Pattern Analysis and Machine Intelligence, vol. 11, No. 3, Mar. 1989, pp. 304–314.

Amzel, L.M., "Structure–base drug design," Current Opinion in Biotechnology, vol. 9, No. 4, Aug. 1998, pp. 366–369.

Blaney, J.M. and Martin, E.J., "Computational approaches for combinatorial library design and molecular diversity analysis," Current Opinion in Chemical Biology, vol. 1, No. 1, Jun. 1997, pp. 54–59.

Brown, R.D. and Clark, D.E., "Genetic diversity: applications of evolutionary algorithms to combinatorial library design," Expert Opinion on Therapeutic Patents, vol. 8, No. 11, Nov. 1998, pp. 1447–1459.

Caflisch, A. and Karplus, M., "Computational combinatorial chemistry for de novo ligand design: Review and Assessment," Perspectives in Drug Discovery and Design, vol. 3, 1995, pp. 51–84.

Danheiser, S.L., "Current Trends in Synthetic Peptide and Chemical Diversity Library Design," Genetic Engineering News, May 1, 1994, pp. 10 and 31.

Eichler, U. et al., "Addressing the problem of molecular diversity," Drugs of the Future, vol. 24, No. 2, 1999, pp. 177–190.

Felder, E.R. and Poppinger, D., "Combinatorial Compound Libraries for Enhanced Drug Discovery Approaches," Advances in Drug Research, vol. 30, 1997, pp. 112–199.

Geysen, H.M. and Mason, T.J., "Screening Chemically Synthesized Peptide Libraries for Biologically–Relevant Molecules," Bioorganic & Medicinal Chemistry Letters, vol. 3, No. 3, 1993, pp. 397–404.

Houghten, R.A. et al., "The Use of Synthetic Peptide Combinatorial Libraries for the Identification of Bioactive Peptides," Peptide Research, vol. 5, No. 6, 1992, pp. 351–358.

Klopman, G., "Artificial Intelligence Approach to Structure–Activity Studies. Computer Automated Structure Evaluation of Biological Activity of Organic Molecules," J. Am. Chem. Soc., vol. 106, No. 24, Nov. 28, 1984, pp. 7315–7321.

Lajiness, M.S. et al., "Implementing Drug Screening Programs Using Molecular Similarity Methods," QSAR: Quantitative Structure–Activity Relationships in Drug Design, 1989, pp. 173–176.

Loew, G.H. et al., "Strategies for Indirect Computer–Aided Drug Design," Pharmaceutical Research, vol. 10, No. 4, 1993, pp. 475–486.

Lynch, M.F. et al., "Generic Structure Storage and Retrieval," J. Chem. Inf. Comput. Sci., vol. 25, No. 3, Aug. 1985, pp. 264–270.

Myers, P.L. et al., "Rapid, Reliable Drug Discovery," Today's Chemist At Work, Jul./Aug. 1997, pp. 46–48, 51 & 53.

Pabo et al., "Computer–Aided Model Building Strategies for Protein Design," Biochemistry, vol. 25, No. 20, 1986, pp. 5987–5991.

Saudek et al., "Solution Conformation of Endothelin–1 by H NMR, CD, and Molecular Modeling," International Journal of Peptide Protein Res., vol. 37, No. 3, 1991, p. 174–179.

Singh, J. et al., "Application of Genetic Algorithms to Combinatorial Synthesis: A Computational Approach to Lead Identification and Lead Optimization," J. Am. Chem. Soc., vol. 118, No. 7, Feb. 21, 1996, pp. 1669–1676.

Van Drie, J.H. and Lajiness, M.S., "Approaches to virtual library design," Drug Discovery today, vol. 3, No. 6, Jun. 1998, pp. 274–283.

Walters, W.P., "Virtual screening—an overview," Drug Discovery today, vol. 3, No. 4, Apr. 1998, pp. 160–178.

Weber, L., "Evolutionary combinatorial chemistry: application of genetic algorithms," Drug Discovery today, vol. 3, No. 8, Aug. 1998, pp. 379–385.

Weber, L. et al., "Optimization of the Biological Activity of Combinatorial Compound Libraries by a Genetic Algorithm," Angewandte Chemie International Edition in English, vol. 34, No. 20, 1995, pp. 2280–2282.

"3DP gains drug research patent", Source of publication unclear, vol. 32, No. 1, Jan. 1996, 2 pages.

"Accelerate the Discovery Cycle with Chem–X!", Source and date of publication unclear, 2 pages.

Agrafiotis, D. K., et al., "Stochastic Algorithms for Maximizing Molecular Diversity", *Journal of Chemical Information and Computer Sciences.* vol. 37, pp. 841–851, (1997).

Alsberg, B.K. et al., "Classification of pyrolysis mass spectra by fuzzy multivariate rule induction–comparison with regression, K–nearest neighbour, neural and decision–tree methods", *Analytica Chimica Acta,* vol. 348, No. 1–3, pp. 389–407, (Aug. 20, 1997).

Andrea, T.A. et al., "Applications of Neural Networks in Quantitative Structure–Activity Relationships of Dihydrofolate Reductase Inhibitors", *Journal of Medicinal Chemistry,* vol. 34, No. 9, pp. 2824–2836, (1991).

Aoyama, T. et al., "Neural Networks Applied to Quantitative Structure–Activity Relationship Analysis", *Journal of Medicinal Chemistry,* vol. 33, No. 9, pp. 2583–2590, (1990).

Aoyama, T. and Hiroshi Ichikawa, "Obtaining the Correlation Indices between Drug Activity and Structural Parameters Using a Neural Network", *Chemical & Pharmaceutical Bulletin,* vol. 39, No. 2, pp. 372–378, (1991).

"ArQule Inc", from http://www.biportfolio.com/arqule/products.htm, 5 pages, (Mar. 18, 1998).

Baum, R.M., "Combinatorial Approaches Provide Fresh Leads for Medicinal Chemistry", *Chemical & Engineering News,* Feb. 7, 1994, (pp. 20–26).

Bentley, J. L., "Multidimensional Binary Search Trees Used for Associative Searching", *Communications of the ACM,* vol. 18, No. 9, pp. 509–517, (Sep. 1975).

Bottou, L. and Vladimir Vapnik, "Local Learning Algorithms", *Neural Computation,* vol. 4, No. 6, pp. 888–900, (Nov. 1992).

Boulu, L.G. and Gordon M. Crippen, "Voronoi Binding Site Models: Calculation of Binding Modes and Influence of Drug Binding Data Accuracy", *Journal of Computational Chemistry,* vol. 10, No. 5, pp. 673–682, (1989).

Boulu, L.G. et al., "Voronoi Binding Site Model of a Polycyclic Aromatic Hydrocarbon Binding Protein", *Journal of Medicinal Chemistry,* vol. 33, No. 2, pp. 771–775, (1990).

Brown, R. D. and Yvonne C. Martin, "Use of Structure–Activity Data To Compare Structure–Based Clustering Methods and Descriptors for Use in Compound Selection", *Journal of Chemical Information and Computer Sciences,* vol. 36, No. 3, pp. 572–584, (1996).

Cacoullos, T., "Estimation of a Multivariate Density", *Annals of The Institute of Statistical Mathematics,* vol. 18, No. 2, pp. 179–189, (1966).

Clark, R.D., "OptiSim: An Extended Dissimilarity Selection Method for Finding Diverse Representative Subsets", *Journal of Chemical Information and Computer Sciences.* vol. 37, No. 6, pp. 1181–1188 (12 Page Internet printout), 1997.

Clark, D. E., and David R. Westhead, "Evolutionary algorithms in computer–aided molecular design", *Journal of Computer–Aided Molecular Design,* vol. 10, No. 4, pp. 337–358, (Aug. 1996).

Cramer, R. D. III et al., "Comparative Molecular Field Analyisis (CoMFA). 1. Effect of Shape on Binding of Steroids to Carrier Proteins", *Journal of The American Chemical Society,* vol. 100, No. 18, pp. 5959–5967, (Aug. 31, 1988).

Cramer, R. D. III et al., "Substructural Analysis. A Novel Approach to the Problem of Drug Design", *Journal of Medicinal Chemistry,* vol. 17, No. 5, pp. 533–535, (May 1974).

Crippen, G. M., "Voronoi binding Site Models", *Journal of Computational Chemistry,* vol. 8, No. 7, pp. 943–955, (Oct./Nov. 1987).

Friedman, J. H. et al., "An Algorithm for Finding Best Matches in Logarithmic Expected Time", *ACM Transactions on Mathematical Software,* vol. 3, No. 3, pp. 209–226, (Sep. 1977).

Friedman, J.H., "Fitting Functions To Noisy Data In High Dimensions", Department of Statistics–Stanford University Technical Report No. 101, (Aug., 1988).

Gallop, M. A. et al., "Applications of Combinatorial Technologies to Drug Discovery. 1. Background and Peptide Combinatorial Libraries", *Journal of Medicinal Chemistry,* vol. 37, No. 9, pp. 1233–1251, (Apr. 29, 1994).

Ghose, A. K. and Gordon M. Crippen, "Use of Physicochemical Parameters in Distance Geometry and Related Three–Dimensional Qantitative Structure–Activity Relationships: A Demonstration Using *Escherichia coli* Dihydrofolate Reductase Inhibitors", *Journal of Medicinal Chemistry,* vol. 28, No. 3, pp. 333–346, (1985).

Good, A. C. et al., "Structure–Activity Relationships from Molecular Similarity Matrices", *Journal of Medicinal Chemistry,* vol. 36, No. 4, pp. 433–438, (Feb. 19, 1993).

Gordon, E. M., "Applications of Combinatorial Technologies to Drug Discovery. 2. Combinatorial Organic Synthesis, Library Screening Strategies, and Future Directions", *Journal of Medicinal Chemistry,* vol. 37, No. 10, (May 13, 1994).

Hartigan, J. A., "Representation of Similarity Matrices By Trees", *Journal of the American Statistical Association.* vol. 62, No. 320, pp. 1140–1158, (Dec., 1967).

Hopfinger, A. J., "A QSAR Investigation of Dihydrofolate Reductase Inhibition by Baker Triazines based upon Molecular Shape Analysis", *Journal of the American Chemical Society,* vol. 102, No. 24, pp. 7196–7206, (Nov. 19, 1980).

Jackson, R. C., "Update on computer–aided drug design", *Current Opinion in Biotechnology,* vol. 6, No. 6, pp. 646–651, (Dec., 1995).

Kim, K. H., "Comparative molecular field analysis (CoFMA)", *Molecular Similarity in Drug Design,* ed. P. M. Dean, Blackie Academic & Professional, 1995, Ch. 12 (pp. 291–324).

Kohonen, T., "Self–Organized Formation of Topologically Correct Feature Maps", *Biological Cybernetics,* vol. 43, pp. 59–69, (1982).

Koile, K. and Richard Shapiro, "Building A Collaborative Drug Design System", *Proceedings of the 25h Hawaii International Conference on System Sciences,* pp. 706–716, (1992).

Kowalski, B. R. and C. F. Bender, "Pattern Recognition. II. Linear and Nonlinear Methods for Displaying Chemical Data", *Journal of the American Chemical Society,* pp. 686–693, (Feb. 7, 1973).

Kruskal, J. B., "Nonmetric Multidimensional Scaling: A Numerical Method", *Psychometrika,* vol. 29, No. 2, pp. 115–129, (Jun., 1964).

Lengauer, T. and Matthias Rarey, "Computational methods for biomolecular docking", *Current Opinion in Structural Biology,* vol. 6, No. 3, pp. 402–406, (Jun., 1996).

Luke, B. T., "Evolutionary Programming Applied to the Development of Quantitative Structure–Activity Relationships and Quantitative Structure–Property Relationships", *Journal of Chemical Information and Computer Sciences,* vol. 34, pp. 1279–1287, (Nov./Dec., 1994).

Martin, E. J. et al., "Does Combinatorial Chemistry Obviate Computer–Aided Drug Design?", *Reviews in Computational Chemistry*, vol. 10, pp. 75–99, (1997).

Martin, E. J. et al., "Measuring Diversity: Experimental Design of Combinatorial Libraries for Drug Discovery", *Journal of Medicinal Chemistry*, vol. 38, No. 9, pp. 1431–1436, (Apr. 28, 1995).

McMartin, C. and Regine S. Bohacek, "QXP: Powerful, rapid computer algorithms for structure–based drug design", *Journal of Computer–Aided Molecular Design*, vol. 11, pp. 333–344, (1997).

Mezey, P. G. and P. Duane Walker, "Fuzzy molecular fragments in drug research", *Drug Discovery Today*, vol. 2, No. 4, (Apr., 1997).

Müller, K., "On the paradigm shift from rational to random design", *Journal of Molecular Structure (Theochem)398–399*, Special Issue, pp. 467–471, (1997).

Myers, P., "The Design Of A Universal, Informer™ Library", Combichem, Inc., 10 pages, Date unknown.

Oinuma, H. et al., "Neural Networks Applied to Structure–Activity Relationships", *Journal of Medicinal Chemistry*, vol. 33, No. 3, pp. 905–908, (1990).

Omohundro, S. M., "Bumptrees for Efficient Function, Constraint, and Classification Learning", International Computer Science Institute, pp. 693–699, Source and Date unknown.

Parrill, A. L., "Evolutionary and genetic methods in drug design", *Drug Discovery Today*, vol. 1, No. 12, pp. 514–521, (Dec., 1996).

Polanski, J., "A neural network for the simulation of biological systems", *Journal of Molecular Structure (Theochem)398–399*, Special Issue, pp. 565–571, (1997).

Ramos–Nino, M. E. et al., "A comparison of quantitative structure–activity relationships for the effect of benzoic and cinnamic acids on *Listeria monocytogenes* using multiple linear regression, artificial neural network and fuzzy systems", *Journal of Applied Microbiology*, vol. 82, No. 2, pp. 168–175, (Feb., 1997).

Rogers, D. and A. J. Hopfinger, "Application of Genetic Function Approximation to Quantitative Structure–Activity Relationships and Quantitative Structure–Property Relationships", *Journal of Chemical Information and Computer Sciences*, vol. 34, No. 4, pp. 854–866, (Jul./Aug., 1994).

Sammon, J. W., Jr., "A Nonlinear Mapping for Data Structure Analysis", *IEEE Transactions on Computers*, vol. C–18, No. 5, pp. 401–409, (May, 1969).

Simon, Z. et al., "Mapping of dihydrofolate–reductase Receptor Site by Correlation with Minimal Topological (Steric) Differences", *Journal of Theoretical Biology*, vol. 66, No. 3, pp. 485–495, (Jun. 7, 1997).

Smellie, A. S. et al., "Fast Drug–Receptor Mapping by Site–Directed Distances; A Novel Method of Predicting New Pharmacological Leads", *Journal of Chemical and Computer Sciences*, vol. 31, No. 3, pp. 386–392, (Aug. 1991).

Specht, D. F., "A General Regression Neural Network", *IEEE Transactions on Neural Networks*, vol. 2, No. 6, pp. 568–576, (Nov., 1991).

Svozil, D. et al., "Neural Network Prediction of the Solvatochromic Polarity/Polarizability Paramter $\pi^H_2$", *Journal of Chemical Information and Computer Sciences*, vol. 37, No. 2 (1997).

Todorov, N. P. and P. M. Dean, "Evaluation of a method for controlling molecular scaffold diversity in de novo ligand design", *Journal of Computer–Aided Molecular Design*, vol. 11, pp. 175–192, (1997).

Torgerson, W. S., "Multidimensional Scaling: I. Theory and Method", *Psychometrika*, vol. 17, No. 4, pp. 401–419, (Dec., 1952).

Vapnik, V., "Principles of Risk Minimization for Learning Theory", *Advances in Neural Information Processing Systems 4*, pp. 831–838, Date unknown.

Vapnik, V. and L. Bottou, "Local Algorithms for Pattern Recognition and Dependencies Estimation", *Neural Computation*, vol. 5, No. 6, pp. 893–909, (Nov., 1993).

Viswanadhan, V. N. et al., "Mapping the binding site of the nucleoside transporter protein: a 3D–QSAR study", *Biochimica et Biophysica Acta*, vol. 1039, No. 3, pp. 356–366, (1990).

Warr, W. A., "Exploiting Molecular Diversity: Small Molecule Libraries for Drug Discovery", Report of Conference held in La Jolla, California, Jan. 23–25, 1995.

Westhead, D. R. et al., "A comparison of heuristic search algorithms for molecular docking", *Journal of Computer–Aided Molecular Design*, vol. 11, pp. 209–228, (1997).

Willett, P., "Genetic algorithms in molecular recognition and design", *Trends in Biotechnology*, vol., 13, No. 12, pp. 516–521, (Dec., 1995).

Willett, P. and Vivienne Winterman, "A Comparison of Some Measures for the Determination of Inter–Molecular Structural Similarity Measures of Inter–Molecular Structural Similarity", *Quantitative Structure–Activity Relationships*, vol. 5, No. 1, pp. 18–25, (Mar., 1986).

Zadeh, L. A., "Communication Fuzzy Algorithms", *Information and Control*, vol. 12 No. 2, pp. 94–102, (Feb., 1968).

Zadeh, L. A., "Fuzzy Sets", *Information and Control*, vol. 8, No. 3, pp. 338–353, (Jun., 1965).

Copy of International Search Report issued May 13, 1998 for PCT/US97/20918.

Copy of International Search Report issued Apr. 21, 1998 for PCT/US97/20919.

de Riddler, D. and Duin, R.P.W., "Sammon's mapping using neural networks: A comparison," *Pattern Recognition Letters*, Elsevier Science B.V., vol. 18, No. 11–13, 1997, pp. 1307–1316.

Kim, H. et al., "Self–Organized Distributed Networks for Learning Highly Nonlinear Mapping," *Intelligent Engineering Systems Through Artificial Neural Networks*, vol. 4, Nov. 13–16, 1994, pp. 109–114.

Pal, N.R. and Eluri, V.K., "Two Efficient Connectionist Schemes for Structure Preserving Dimensionality Reduction," *IEEE Transactions on Neural Networks*, IEEE, vol. 9, No. 6, Nov. 1998, pp. 1142–1154.

Domine, D. et al., "Non–Linear Mapping for Structure–Activity and Structure–Property Modelling," *Journal of Chemometrics*, John Wiley & Sons, Ltd., vol. 7, No. 4, Jul.–Aug. 1993, pp. 227–242.

Borg, Inger and Groenen, Patrick, *Modern Multidimensional Scaling Theory and Applications*, Springer Series in Statistics, 1997, entire book submitted.

Agrafiotis, D.K. et al., "Advances in diversity profiling and combinatorial series design," *Molecular Diversity*, vol. 4, 1999, pp. 1–22.

Agrafiotis, D.K. and Lobanov, V.S., "An Efficient Implementation of Distance–Based Diveristy Measure based on k–d Trees," *J. Chem. Inf. Comput. Sci.,* vol. 39, No. 1, Jan./Feb. 1999, pp. 51–58.

Agrafiotis, D.K. and Lobanov, V.S., "Bridging The Gap Between Diversity And QSAR," *Abstracts of Papers Part 1: 215th ACS National Meeting,* Mar. 29–Apr. 2, 1998, p. 181–COMP.

Agrafiotis, D.K. and Jaeger, E.P., "Directed Diversity®: An Operating System for Combinatorial Chemistry," *Abstracts of Papers Part 1: 211th ACS National Meeting,* Mar. 24–28, 1996, p. 46–COMP.

Agrafiotis, D.K., "Diversity of Chemical Libraries," *Encyclopedia of Computational Chemistry,* vol. 1:A–D, 1998, pp. 742–761.

Agrafiotis, D.K., "On the Use of Information Theory for Assessing Molecular Diversity," *J. Chem. Inf. Comput. Sci.,* vol. 37, No. 3, May/Jun. 1997, pp. 576–580.

Agrafiotis, D.K. et al., "Parallel QSAR," *Abstracts of Papers Part 1: 217th ACS National Meeting,* Mar. 21–25, 1999, p. 50–COMP.

Agrafiotis, D.K. et al., "PRODEN: A New Program for Calculating Integrated Projected Populations," *Journal of Computational Chemistry,* vol. 11, No. 9, Oct. 1990, pp. 1101–1110.

Agrafiotis, D.K. and Jaeger, E.P., "Stochastic Algorithms for Exploring Molecular Diversity," *Abstracts of Papers Part 1: 213th ACS National Meeting,* Apr. 13–17, 1997, p. 16–CINF.

Agrafiotis, D., "Theoretical Aspects of the Complex: Arts and New Technologies," *Applications and Impacts Information Processing '94,* vol. II, 1994, pp. 714–719.

Biswas, G. et al., "Evaluation of Projection Algorithms," *IEEE Transactions On Pattern Analysis And Machine Intelligence,* vol. PAMI–3, No. 6, Nov. 1981, pp. 701–708.

Bonchev, D. and Trinajstić, N., "Information theory, distance matrix, and molecular branching," *The Journal of Chemical Physics,* vol. 67, No. 10, Nov. 15, 1977, pp. 4517–4533.

Chang, C.L. and Lee, R.C.T., "A Heuristic Relaxation Method for Nonlinear Mapping in Cluster Analysis," *IEEE Transactions on Systems, Man, and Cybernetics,* vol. SMC–3, Mar. 1973, pp. 197–200.

Cramer, R.D. et al., "Virtual Compound Libraries: A New Approach to Decision Making in Molecular Discovery Research," *J. Chem. Inf. Comput. Sci.,* vol. 38, No. 6, Nov./Dec., 1998, p. 1010–1023.

DeMers, D. and Cottrell, G., "Non–Linear Dimensionality Reduction," *Advances in Neural Information Processing Systems,* vol. 5, 1993, pp. 580–587.

Frey, P.W. and Slate, D.J., "Letter Recognition Using Holland–Style Adaptive Classifiers," *Machine Learning,* vol. 6, 1991, pp. 161–182.

Friedman, J.H., "Exploratory Projection Pursuit," *Journal of the American Statistical Association,* vol. 82, No. 397, Mar. 1987, pp. 249–266.

Friedman, J.H. and Tukey, J.W., "A Projection Pursuit Algorithm for Exploratory Data Analysis," *IEEE Transactions on Computers,* vol. C–23, No. 9, Sep. 1974, pp. 881–889.

Garrido, L. et al., "Use of Multilayer Feedforward Neural Nets As A Display Method for Multidimensional Distributions," *International Journal of Neural Systems,* vol. 6, No. 3, Sep. 1995, pp. 273–282.

Ghose, A.K. et al., "Prediction of Hydrophobic (Lipophilic) Properties of Small Organic Molecules Using Fragmental Methods: An Analysis of ALOGP and CLOGP Methods," *J. Phys. Chem. A,* vol. 102, No. 21, May 21, 1998, pp. 3762–3772.

Hall, L.H. and Kier, L.B., "The Molecular Connectivity Chi Indexes and Kappa Shape Indexes in Structure–Property Modeling," *Reviews in Computational Chemistry: Advances,* 1991, pp. 367–422.

Hecht–Nielsen, R., "Replicator Neural Networks for Universal Optimal Source Coding," *Science,* vol. 269, Sep. 29, 1995, pp. 1860–1863.

Hotelling, H., "Analysis of a Complex of Statistical Variables into Principal Components," *The Journal of Educational Psychology,* vol. XXIV, No. 6, Sep. 1993, pp. 417–441.

Hotelling H., "Analysis of a Complex of Statistical Variables into Principal Components," *The Journal of Educational Psychology,* vol. XXIV, No. 7, Oct. 1933, pp. 498–520.

Lee, R.C.T. et al., "A Triangulation Method for the Sequential Mapping of Points from N–Space to Two–Space," *IEEE Transactions on Computers,* Mar. 1977, pp. 288–292.

Lipinski, C.A. et al., "Experimental and computational approaches to estimate solubility and permeability in drug discovery and development settings," *Advanced Drug Delivery Reviews,* vol. 23, 1997, pp. 3–25.

Lobanov, V.S. and Agrafiotis, D.K., "Intelligent Database Mining Techniques," *Abstracts of Papers Part 1: 215th ACS National Meeting,* Mar. 29–Apr. 2, 1998, p. 19–COMP.

Lobanov, V.S. et al., "Rational Selections from Virtual Libraries," *Abstracts of Papers Part 1: 217th ACS National Meeting,* Mar. 21–25, 1999, p. 181–COMP.

Mao, J. and Jain, A.K., "Artificial Neural Networks for Feature Extraction and Multivariate Data Projection," *IEEE Transactions on Neural Networks,* vol. 6, No. 2, Mar. 1995, pp. 296–317.

Oja, E., "Principal Components, Minor Components, and Linear Neural Networks," *Neural Networks,* vol. 5, 1992, pp. 927–935.

Patterson, D.E. et al., "Neighborhood Behavior: A Useful Concept for Validation of 'Molecular Diversity' Descriptors," *Journal of Medicinal Chemistry,* vol. 39, No. 16, 1996, pp. 3049–3059.

Pykett, C.E., "Improving the Efficiency of Sammon's Nonlinear Mapping by Using Clustering Archetypes," *Electronics Letters,* vol. 14, No. 25, Dec. 7, 1978, pp. 799–800.

Rubner, J. and Tavan, P., "A Self–Organizing Network for Principal–Component Analysis," *Europhysics Letters,* vol. 10, No. 7, Dec. 1, 1989, pp. 693–698.

Sadowski, J. et al., "Assessing Similarity and Diversity of Combinatorial Libraries by Spatial Autocorrelation Functions and Neural Networks," *Angewandte Cheme,* vol. 34, No. 23/24, Jan. 5, 1996, pp. 2674–2677.

Thompson, L.A. and Ellman, J.A., "Synthesis and Applications of Small Molecule Libraries," *Chemical Reviews,* vol. 96, No. 1, Jan./Feb. 1996, pp. 555–600.

Barnard, John M. and Downs, Geoff M., "Computer representation and manipulation of combinatorial libraries," *Perspectives in Drug Discovery and Design,* 1997, pp. 13–30.

Brint, Andrew, T. and Willett, Peter, "Upperbound procedures for the identification of similar three–dimensional chemical structures," *Journal of Computer–Aided Molecular Design,* vol. 2, No. 4, 1988, pp. 311–320.

Brown, Robert D. and Martin, Yvonne C., "Designing Combinatorial Library Mixtures Using a Genetic Algorithm," *Journal of Medicinal Chemistry*, vol. 40, No. 15, 1997, pp. 2304–2313.

Gillet, Valerie J. et al., "The Effectiveness of Reactant Pools for Generating Structurally–Diverse Combinatorial Libraries," *Journal of Chemical Information Computer Sciences*, vol. 37, No. 4, 1997, pp. 731–740.

Gillet, Valerie J. et al., "Selecting Combinatorial Libraries to Optimize Diversity and Physical Properties," *Journal of Chemical Information Computer Sciences*, vol. 39, No. 1, 1999, pp. 169–177.

Kearsley, Simon K. et al., "Chemical Similarity Using Physiochemical Property Descriptors," *Journal of Chemical Information Computer Science*, vol. 36, No. 1, 1996, pp. 118–127.

Leland, Burton A. et al., "Managing the Combinatorial Explosion," *Journal of Chemical Information Computer Science*, vol. 37, No. 1, 1997, pp. 62–70.

Lewis, Richard A. et al., "Similarity Measures for Rational Set Selection and Analysis of Combinatorial Libraries: The Diverse Property–Derived (DPD) Approach," *Journal of Chemical Information Computer Science*, vol. 37, No. 3, 1997, pp. 599–614.

Martin, Eric J. and Critchlow, Roger E., "Beyond Mere Diversity: Tailoring Combinatorial Libraries for Drug Discovery," *Journal of Combinatorial Chemistry*, vol. 1, No. 1, 1999, pp. 32–45.

Sheridan, Robert P. et al., "Chemical Similarity Using Geometric Atom Pair Descriptors," *Journal of Chemical Information Computer Science*, vol. 36, No. 1, 1996, pp. 128–136.

Willett, Peter et al., "Chemical Similarity Searching," *Journal of Chemical Information Computer Science*, vol. 38, No. 6, 1998, pp. 983–996.

Agrafiotis, Dimitris K. and Lobanov, Victor S., "Ultrafast Algorithm for Designing Focused Combinational Arrays," *J. Chem. Inf. Comput. Sci.*, 2000, vol. 40, No. 4, pp. 1030–1038.

Ajay et al., "Can We Learn To Distinguish between 'Drug–Like' and 'Nondrug–like' Molecules?" *J. Med. Chem.*, 1998, vol. 41, No. 18, pp. 3314–3324.

Brown, Robert D. and Martin, Yvonne C., "Designing Combinatorial Library Mixtures Using a Genetic Algorithm," *J. Med. Chem.*, 1997, vol. 40, No. 15, pp. 2304–2313.

Brown, Robert D. and Martin, Yvonne C., "The Information Content of 2D and 3D Structural Descriptors Relevant to Ligand–Receptor Binding," *J. Chem. Info. Comput. Sci.*, 1997, vol. 37, No. 1, pp. 1–9.

Brown, Robert D. and Martin, Yvonne C., "Use of Structure–Activity Data To Compare Structure–Based Clustering Methods and Descriptors for Use in Compound Selection," *J. Chem. Inf. Sci.*, 1996, vol. 36, No. 3, pp. 572–584.

Cummins, David J. et al., "Molecular Diversity in Chemical Databases: Comparison of Medicinal Chemistry Knowledge Bases and Databases of Commercially Available Compounds," *American Chemical Society*, 1996, 14 pages.

*Daylight Theory: Fingerprints* (visited Sep. 26, 2000) <http://www.daylight.com/dayhtml/doc/theory/theory.finger.html>, 8 pages.

*Daylight Theory: Smarts* (visited Sep. 26, 2000) <http://www.daylight.com/dayhtml/doc/theory/theory.smarts.html>, 10 pages.

Downs, Geoff M. and Barnard, John M., "Techniques for Generating Descriptive Fingerprints in Combinatorial Libraries," *J. Chem. Inf. Comput. Sci.*, 1997, vol. 37, No. 1, pp. 59–61.

Gillet, Valerie J., "Background Theory of Molecular Diversity," *Molecular Diversity in Drug Design*, 1999, pp. 43–65.

Good, Andrew C. and Lewis, Richard A., "New Methodology for Profiling Combinatorial Libraries and Screening Sets: Cleaning Up the Design Process with HARPick," *J. Med. Chem.*, 1997, vol. 40, pp. 3926–3936.

Gorse, Dominique and Lahana, Roger, "Functional diversity of compound libraries," *Current opinion in chemical biology*, 2000, vol. 4, pp. 287–294.

Jamois, Eric A. et al., "Evaluation of Reagent–Based and Product–Based Strategies in the Design of Combinatorial Library Subsets," *J. Chem. Inf. Comput. Sci.*, 2000, vol. 40, pp. 63–70.

Leach, Andrew R. et al., "Implementation of a System for Reagent Selection and Library Enumeration, Profiling, and Design," *J. Chem. Inf. Comput. Sci.*, 1999, vol. 39, No. 6, pp. 1161–1172.

Leach, Andrew R. and Hann, Michael M., "The in silico world of virtual libraries," *Drug discovery today*, 2000, vol. 5, No. 8, pp. 326–336.

Leland, Burton A. et al., "Managing the Combinatorial Explosion," *J. Chem. Inf. Comput. Sci.*, 1997, vol. 37, No. 1, pp. 62–70.

Lobanov, Victor S. and Agrafiotis, Dimitris K., "Stochastic Similarity Selections from Large Combinatorial Libraries," *J. Chem. Inf. Comput. Sci.*, 2000, vol. 40, No. 2, pp. 460–470.

Matter, Hans and Pötter, Thorsten, "Comparing 3D Pharmacophore Triplets and 2D Fingerprints for Selecting Diverse Compound Subsets," *J. Chem. Inf. Comput. Sci.*, 1999, vol. 39, No. 6, pp. 1211–1225.

Matter, Hans, "Selecting Optimally Diverse Compounds from Structure Databases: A Validation Study of Two–Dimensional and Three–Dimensional Molecular Descriptors," *J. Med. Chem.*, 1997, vol. 40, No. 8, pp. 1219–1229.

Sadowski, Jens and Kubinyi, Hugo, "A Scoring Scheme for Discriminating between Drugs and Nondrugs," *J. Med. Chem.*, 1998, vol. 41, No. 18, pp. 3325–3329.

Schnur, Dora, "Design and Diversity Analysis of Large Combinatorial Libraries Using Cell–Based Methods," *J. Chem. Inf. Comput. Sci.*, 1999, vol. 39, No. 1, pp. 36–45.

Schuffenhauer, Ansgar et al., "Similarity Searching in Files of Three–Dimensional Chemical Structures: Analysis of the BIOSTER Database Using Two–Dimensional Fingerprints and Molecular Field Descriptors," *J. Chem. Inf. Comput. Sci.*, 2000, vol. 40, No. 2, pp. 295–307.

Turner, David B. et al., "Rapid Quantification of Molecular Diversity for Selective Database Acquisition," *J. Chem. Inf. Sci.*, 1997, vol. 37, No. 1, pp. 18–22.

Wang, Jing and Ramnarayan, Kal, "Toward Designing Drug–Like Libraries: A Novel Computational Approach for Prediction of Drug Feasibility of Compounds," *J. Comb. Chem.*, 1999, vol. 1, No. 6, pp. 524–533.

Gasteiger et al, "Assessment of the Diversity of Combinatorial Libraries by an Encoding of Melcular Surface properties," *Abstracts of Papers, American Chemical Society*, 211th ACS National Meeting, Item 070, Mar. 1996.

Hassan, Moises et al., "Optimization and visualization of molecular diversity of combinatorial libraries," *Molecular Diversity*, 1996, vol. 2, pp. 64–74.

Bellman, R.E., *Adaptive Control Processes,* Princeton Univ. Press, Princeton, NJ (1961).

Bezdek, J.C., *Pattern Recognition with Fuzzy Objective Function Algorithms,* Plenum Press, New York, NY (1981).

Johnson, M.A., and Maggiora, G.M., *Concepts and Applications of Molecular Similarity,* John Wiley and Sons, New York, NY (1998).

Kohonen, T., *Self–Organizing Maps,* Springer–Verlag, Heidelberg (1996).

Oja, E., *Subspace Methods of Pattern Recognition,* Research Studies Press, Letchworth, England (1983).

\* cited by examiner

SYSTEM, METHOD AND COMPUTER PROGRAM PRODUCT FOR IDENTIFYING CHEMICAL COMPOUNDS HAVING DESIRED PROPERTIES

CROSS REFERENCE TO RELATED APPLICATIONS

This application is related to commonly owned U.S. provisional patent application No. 60/030,187, filed Nov. 4, 1996.

BACKGROUND OF THE INVENTION

1. Field of the Invention

The present invention relates generally to the generation of chemical entities with defined physical, chemical and/or bioactive properties, and more particularly, to iterative selection and testing of chemical entities.

2. Related Art

Conventionally, new chemical entities with useful properties are generated by identifying a chemical compound (called a "lead compound") with some desirable property or activity, creating variants of the lead compound, and evaluating the property and activity of those variant compounds. Examples of chemical entities with useful properties include paints, finishes, plasticizers, surfactants, scents, flavorings, and bioactive compounds, but can also include chemical compounds with any other useful property that depends upon chemical structure, composition, or physical state. Chemical entities with desirable biological activities include drugs, herbicides, pesticides, veterinary products, etc. There are a number of flaws with this conventional approach to lead generation, particularly as it pertains to the discovery of bioactive compounds.

One deficiency pertains to the first step of the conventional approach, i.e., the identification of lead compounds. Traditionally, the search for lead compounds has been limited to an analysis of compound banks, for example, available commercial, custom, or natural products chemical libraries. Consequently, a fundamental limitation of the conventional approach is the dependence upon the availability, size, and structural diversity of these chemical libraries. Although chemical libraries cumulatively total an estimated 9 million identified compounds, they reflect only a small sampling of all possible organic compounds with molecular weights less than 1200. Moreover, only a small subset of these libraries is usually accessible for biological testing. Thus, the conventional approach is limited by the relatively small pool of previously identified chemical compounds which may be screened to identify new lead compounds.

Also, compounds in a chemical library are traditionally screened (for the purpose of identifying new lead compounds) using a combination of empirical science and chemical intuition. However, as stated by Rudy M. Baum in his article "Combinatorial Approaches Provide Fresh Leads for Medicinal Chemistry," C&EN, Feb. 7, 1994, pages 20–26, "chemical intuition, at least to date, has not proven to be a particularly good source of lead compounds for the drug discovery process."

Another deficiency pertains to the second step of the conventional approach, i.e., the creation of variants of lead compounds. Traditionally, lead compound variants are generated by chemists using conventional chemical synthesis procedures. Such chemical synthesis procedures are manually performed by chemists. Thus, the generation of lead compound variants is very labor intensive and time consuming. For example, it typically takes many chemist years to produce even a small subset of the compound variants for a single lead compound. Baum, in the article referenced above, states that "medicinal chemists, using traditional synthetic techniques, could never synthesize all of the possible analogs of a given, promising lead compound." Thus, the use of conventional, manual procedures for generating lead compound variants operates to impose a limit on the number of compounds that can be evaluated as new drug leads. Overall, the traditional approach to new lead generation is an inefficient, labor-intensive, time consuming process of limited scope.

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds theoretically can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al., "Applications of Combinatorial Technologies to Drug Discovery, Background and Peptide Combinatorial Libraries," J. Med. Chem. 37, 1233–1250 (1994)).

To date, most work with combinatorial chemical libraries has been limited only to peptides and oligonucleotides for the purpose of identifying bioactive agents; little research has been performed using non-peptide, non-nucleotide based combinatorial chemical libraries. It has been shown that the compounds in peptide and oligonucleotide based combinatorial chemical libraries can be assayed to identify ones having bioactive properties. However, there is no consensus on how such compounds (identified as having desirable bioactive properties and desirable profile for medicinal use) can be used.

Some commentators speculate that such compounds could be used as orally efficacious drugs. This is unlikely, however, for a number of reasons. First, such compounds would likely lack metabolic stability. Second, such compounds would be very expensive to manufacture, since the chemical building blocks from which they are made most likely constitute high priced reagents. Third, such compounds would tend to have a large molecular weight, such that they would have bioavailability problems (i.e., they could only be taken by injection).

Others believe that the compounds from a combinatorial chemical library that are identified as having desirable biological properties could be used as lead compounds. Variants of these lead compounds could be generated and evaluated in accordance with the conventional procedure for generating new bioactive compound leads, described above. However, the use of combinatorial chemical libraries in this manner does not solve all of the problems associated with the conventional lead generation procedure. Specifically, the problem associated with manually synthesizing variants of the lead compounds is not resolved.

In fact, the use of combinatorial chemical libraries to generate lead compounds exacerbates this problem. Greater and greater diversity has often been achieved in combinatorial chemical libraries by using larger and larger compounds (that is, compounds having a greater number of variable subunits, such as pentameric compounds instead of tetrameric compounds in the case of polypeptides). However, it is more difficult, time consuming, and costly to synthesize variants of larger compounds. Furthermore, the real issues of structural and functional group diversity are still not directly addressed; bioactive agents such as drugs and agricultural products possess diversity that could never be achieved with available peptide and oligonucleotide libraries since the available peptide and oligonucleotide components only possess limited functional group diversity and limited topology imposed through the inherent nature of the available components. Thus, the difficulties associated with synthesizing variants of lead compounds are exacerbated by using typical peptide and oligonucleotide combinatorial chemical libraries to produce such lead compounds. The issues described above are not limited to bioactive agents but rather to any lead generating paradigm for which a chemical agent of defined and specific activity is desired.

Additional drawbacks to conventional systems are described in U.S. Pat. No. 5,574,656, titled, "System and Method of Automatically Generating Chemical Compounds with Desired Properties," issued Nov. 12, 1996, incorporated herein in its entirety by reference.

Thus, the need remains for a system and method for efficiently and effectively generating new leads designed for specific utilities.

SUMMARY OF THE INVENTION

The present invention is an automatic, partially automatic, and/or manual iterative system, method and/or computer program product for generating chemical entities having desired or specified physical, chemical, functional, and/or bioactive properties. The present invention is also directed to the chemical entities produced by this system, method and/or computer program product. In an embodiment, the following steps are performed during each iteration:

(1) identify a set of compounds for analysis;

(2) collect, acquire or synthesize the identified compounds;

(3) analyze the compounds to determine one or more physical, chemical and/or bioactive properties (structure-property data); and (4) use the structure-property data to identify another set of compounds for analysis in the next iteration.

For purposes of illustration, the present invention is described herein with respect to the production of drug leads. However, the present invention is not limited to this embodiment.

In one embodiment, the system and computer program product includes an Experiment Planner, a Selector, a Synthesis Module and an Analysis Module. The system also includes one or more databases, such as a Structure-Property database, a Compound Database, a Reagent database and a Compound Library.

The Experiment Planner receives, among other things, Historical Structure-Property data from the Structure-Property database and current Structure-Property data that was generated by the Analysis Module during a prior iteration of the invention.

The Experiment Planner generates Selection Criteria for use by the Selector. One or more of the Selection Criteria can be combined into one or more Objective Functions. An Objective Function describes the collective ability of a given subset of compounds from the Compound Library to simultaneously satisfy all the prescribed Selection Criteria. An Objective Function defines the influence of each Selection Criterion in the final selection. The Selection Criteria and the exact form of the Objective Function can be specified by a human operator or can be automatically generated by a computer program or other process, or can be specified via human/computer interaction.

The one or more Selection Criteria and/or Objective Functions can represent: one or more desired characteristics that the resulting compounds should possess, individually or collectively; one or more undesired characteristics that the resulting compounds should not possess, individually or collectively; and/or one or more constraints that exclude certain compounds and/or combinations of compounds in order to limit the scope of the selection. The Selection Criteria can be in the form of mathematical functions or computer algorithms, and can be calculated using a digital computer.

The Selector receives the Selection Criteria and Objective Functions and searches the Compound Library to identify a subset of compounds that maximizes or minimizes the Objective Functions. The Compound Library can be a collection of pre-existing or virtual chemical compounds.

The Selector identifies a smaller subset of these compounds, referred to herein as a Directed Diversity Library, based on one or more Selection Criteria and/or Objective Functions. The number of compounds in this subset can be specified by the operator or can be determined automatically or partially automatically within any limits specified by the operator.

The Selection Criteria can be applied either simultaneously or sequentially. For example, in one embodiment, one part of the Directed Diversity Library can be selected based on a first set of Criteria and/or Objective Function, while another part of that Directed Diversity Library can be selected based on a second set of Selection Criteria and/or Objective Function.

The compounds comprising the Directed Diversity Library are then collected, acquired or synthesized, and are analyzed to evaluate their physical, chemical and/or bioactive properties of interest. In one embodiment, when a compound in a Directed Diversity Library is available in a Chemical Inventory, the compound is retrieved from the Chemical Inventory. This avoids unnecessary time and expense of synthesizing a compound that is already available. Compounds that are not available from a Chemical Inventory are synthesized in the Synthesis Module.

In one embodiment, the Synthesis Module is an automated robotic module that receives synthesis instructions from a Synthesis Protocol Generator. Alternatively, synthesis can be performed manually or semi-automatically.

The Analysis Module receives the compounds of the Directed Diversity Library from the Chemical Inventory and/or the Synthesis Module. The Analysis Module analyzes the compounds and outputs Structure-Property data. The Structure-Property data is provided to the Experiment Planner and is also stored in the Structure-Property database.

The Experiment Planner defines one or more new Selection Criteria and/or Objective Functions for the next iteration of the invention. The new Selection Criteria and/or Objective Functions can be defined through operator input, through an automated process, through a partially automated process, or any combination thereof.

In one embodiment, current and historical Structure-Property data are provided to an optional Structure-Property Model Generator. The Structure-Property data can include structure-property activity data from all previous iterations or from a subset of all previous iterations, as specified by user input, for example.

The Structure-Property Model Generator generates Structure-Property Models that conform to the observed data. The Structure-Property Models are provided to the Experiment Planner which uses the Models to generate subsequent Selection Criteria and/or Objective Function. The Selection Criteria and/or Objective Functions are provided to the Selector which selects the next Directed Diversity Library therefrom.

In one embodiment, the functions of the Experiment Planner, the Selector and the optional Synthesis Protocol Generator are performed by automated machines under the control of one or more computer programs executed on one or more processors and/or human operators. Alternatively, one or more of the functions of the Experiment Planner, the Selector and the optional Synthesis Protocol Generator can be performed manually.

The functions of the Synthesis Module and the Analysis Module can be performed manually, robotically, or by any combination thereof.

Further features and advantages of the present invention, as well as the structure and operation of various embodiments of the present invention, are described in detail below with reference to the accompanying drawings. In the drawings, like reference numbers indicate identical or functionally similar elements. Also, the leftmost digit(s) of the reference numbers identify the drawings in which the associated elements are first introduced.

BRIEF DESCRIPTION OF THE FIGURES

The present invention will be described with reference to the accompanying drawings, wherein.

DETAILED DESCRIPTION OF THE PREFERRED EMBODIMENTS

Table of Contents

1. General Overview
2. Example Environment
3. Structure-Property Models
   a. Statistical Models
   b. Neural Network Models
      i. Generalized Regression Neural Networks
   c. Fuzzy Logic Models
   d. Hybrid Models
      i. Neuro-fuzzy Models
   e. Model-Specific Methods
      i. Docking Models
      ii. 3D QSAR Models
4. Experiment Planner 130
   a. Selection Criteria 104
      i. First Type of Selection Criteria 104
      ii. Second Type of Selection Criteria 104
   b. Objective Functions 105
5. Selector 106
6. Structure of the Present Invention
7. Operation of the Present Invention
8. Conclusions 1. General Overview The present invention is an iterative system, method and computer program product for generating chemical entities having desired physical, chemical and/or bioactive properties. The present invention iteratively selects, analyzes and evaluates Directed Diversity Libraries for desired properties. The present invention can be implemented as a fully or partially automated, computer-aided robotic system, or without any robotics. The present invention is also directed to the chemical entities generated by operation of the present invention.

Conventional systems perform combinatorial chemical synthesis and analysis of static compound libraries. This tends to be scattershot and random, essentially constituting a "needle in a haystack" research paradigm.

In contrast, the present invention employs a dynamic Compound Library. The Compound Library is dynamic in that the compounds comprising the Compound Library can change from one iteration of the present invention to the next. The dynamic Compound Library can expand and/or contract.

The Compound Library includes chemical compounds that already exist and/or chemical compounds that can be synthesized on demand, either individually or combinatorially. The Compound Library can be a combinatorial chemical library, a set of combinatorial chemical libraries and/or non-combinatorial chemical libraries. However, the Compound Library is not limited to a combinatorial chemical library.

Instead of searching and analyzing the whole Compound Library, the present invention identifies and analyzes particular subsets of the Compound Library. These subsets of the Compound Library are referred to herein as Directed Diversity Libraries. As opposed to conventional techniques, Directed Diversity Libraries provide an optimization approach that is focused and directed.

2. Example Environment

Figure 1:
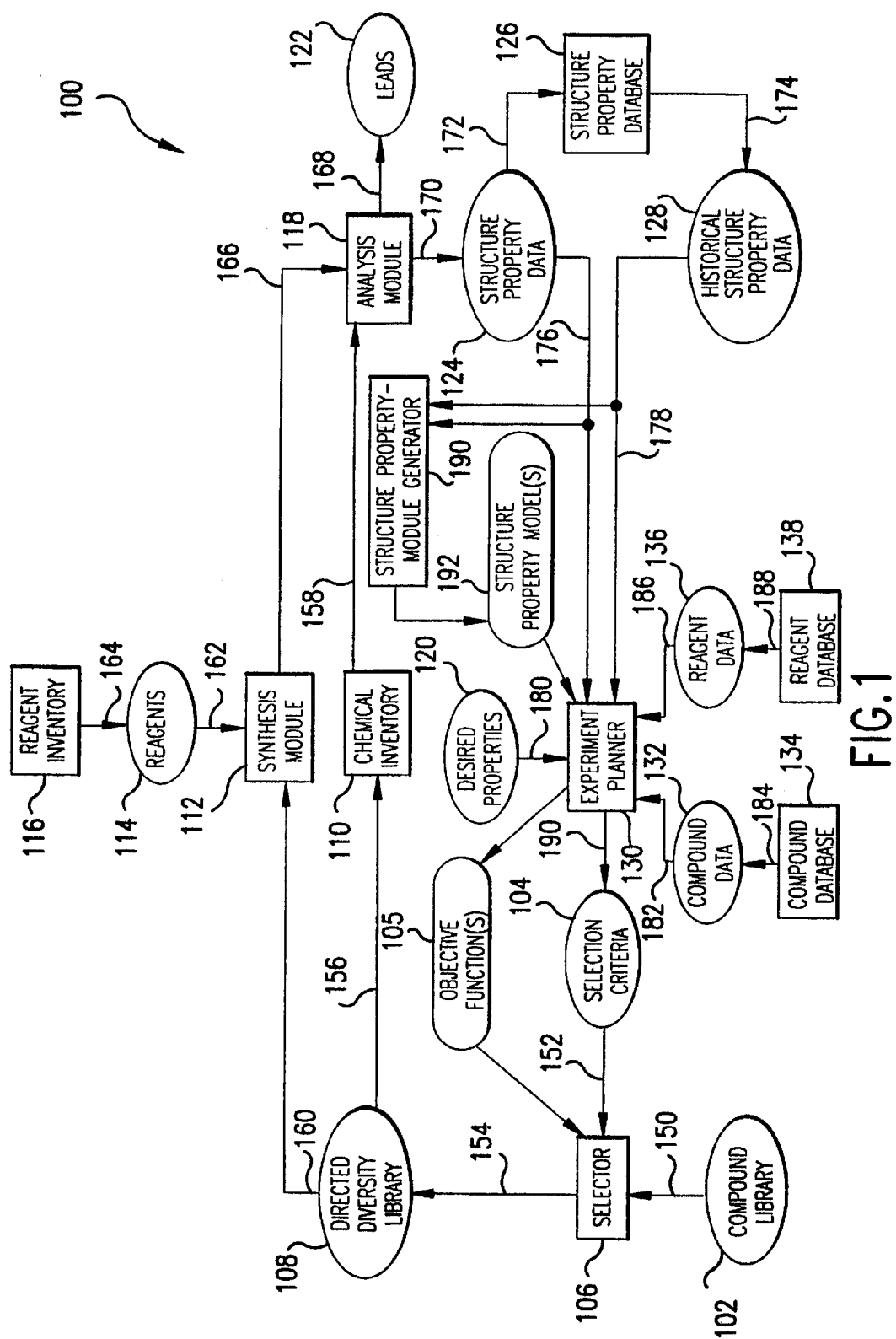
FIG. 1 is a flow diagram depicting the flow of data and materials among elements of a lead generation system, in accordance with the present invention.

Referring to the flow diagram in FIG. 1, a lead generation/optimization system 100 includes an Experiment Planner 130, a Selector 106, a Synthesis Module 112 and an Analysis Module 118. The system also includes one or more databases, such as: a Structure-Property database 126, a Compound Database 134, a Reagent database 138 and a Compound Library 102.

The Selector 106 receives Selection Criteria 104 from the Experiment Planner 130. The Selector 106 can also receive one or more Objective Functions 105 from the Experiment Planner 130.

The Selection Criteria 104 represent desired or undesired characteristics that the resulting compounds should or should not possess, either individually or collectively, and/or constraints that exclude certain compounds and/or combinations of compounds. The Selection Criteria 104 can be in the form of mathematical functions or computer algorithms, and can be calculated using a digital computer.

One or more of the Selection Criteria 104 can be combined into one or more Objective Functions 105 by the Experiment Planner 130. The Objective Functions 105 describe the extent to which a given set of compounds should satisfy all the prescribed Selection Criteria 104. The Objective Functions 105 can define the influence of each Selection Criterion 104 in the selection of a Directed Diversity Library. The Selection Criteria 104 and the exact form of the Objective Functions 105 can be specified by a human operator or can be automatically or semi-automatically generated (with human input) by the Experiment Planner 130.

The Selector 106 searches the Compound Library 102 to identify one or more subsets of compounds that maximize or minimize the Selection Criteria 104 and/or Objective Function 105. The subset of compounds is referred to herein as a Directed Diversity Library 108. Note that the Directed Diversity Library 108 is a list of compounds. These compounds may or may not already exist (i.e., they may or may not be in the Chemical Inventory 110). The properties of the Directed Diversity Library 108 of compounds are generally hitherto unknown. The number of compounds in a Directed Diversity Library can be specified by the operator, or can be determined automatically within any limits specified by the operator.

The Selection Criteria 104 can be applied either simultaneously or sequentially. For example, in one embodiment of the present invention, one part of the Directed Diversity Library 108 can be selected based on a given set of Selection Criteria 104 and/or Objective Function 105, while another part of that Directed Diversity Library 108 can be selected based on a different set of Selection Criteria 104 and/or Objective Function 105. Thus, the present invention represents a multi-objective property refinement system, in the sense that one or more Selection Criteria 104 can be used, and one or more Objective Functions 105 can be pursued, during each iteration.

Compounds from the Directed Diversity Libraries 108 are provided to the Analysis Module 118 for analysis. Alternatively, the compounds can be manually analyzed or partially manually analyzed and partially automatically analyzed. In one embodiment, one or more compounds in a Directed Diversity Library 108 that have previously been synthesized are retrieved from a Chemical Inventory 110 instead of being synthesized again. This saves time and costs associated with re-synthesizing the selected compounds. The Chemical Inventory 110 represents any source of available compounds including, but not limited to, a corporate chemical inventory, a supplier of commercially available chemical compounds, a natural product collection, etc.

A system and computer program product that determines whether a compound in a Directed Diversity Library 108 exists in the Chemical Inventory 110 can be implemented within the Selector Module 102, the Synthesis Module 112 or in any other module. For example, the Selector Module 106 can include instructions for searching the Chemical Inventory 110 to identify and retrieve any previously synthesized compounds therefrom that are listed in the Directed Diversity Library 108 (or a subset of the Directed Diversity Library 108, as determined by user input, for example).

Compounds in the Directed Diversity Library 108 that are not retrieved from the Chemical Inventory 110 are synthesized individually or combinatorially by the Synthesis Module 112. The Synthesis Module 112 can retrieve and selectively combine Reagents 114 from the Reagent Inventory 116, in accordance to a prescribed chemical synthesis protocol.

In one embodiment, the Synthesis Module 112 is used to robotically synthesize compounds. As used herein, the term "robotically" refers to any method that involves an automated or partially automated device that performs functions specified by instructions that the Synthesis Module 112 receives from the operator or some other component of the system of the present invention.

Figure 2:
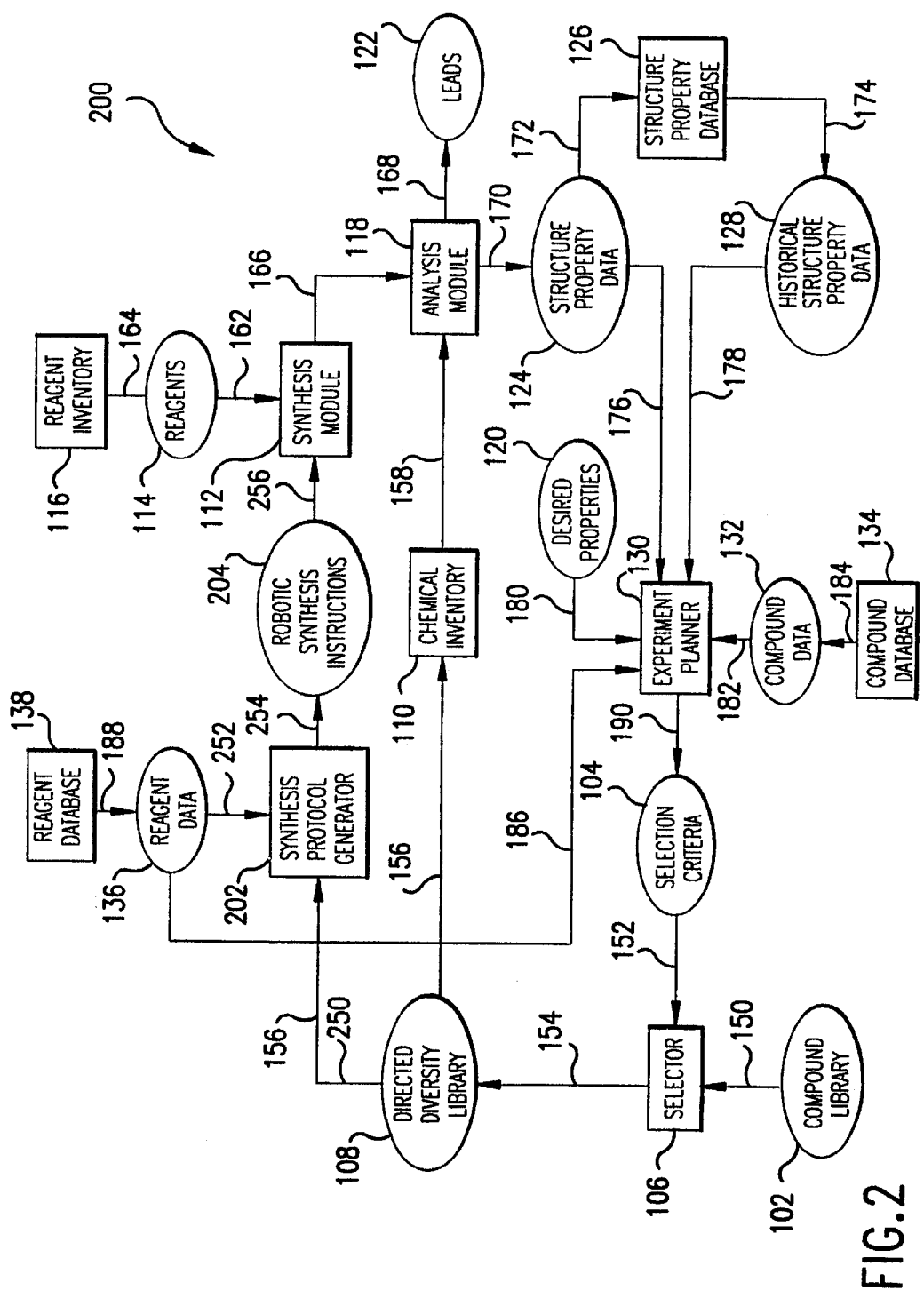
FIG. 2 is a flow diagram depicting the flow of data and materials among elements of an embodiment of the lead generation system, in accordance with the present invention.

For example, refer to FIG. 2, which is similar to FIG. 1, but which illustrates a synthesis protocol generator 202 in the path to the Synthesis Module 112. The Synthesis Protocol Generator 202 provides Robotic Synthesis Instructions 204 to the Synthesis Module 112. The Synthesis Protocol Generator 202 receives a list of compounds in the Directed Diversity Library 108 to be synthesized. The Synthesis Protocol Generator 202 extracts, under computer control, Reagent Data 136 from a Reagent Database 138, and generates Robotic Synthesis Instructions 204 that will enable the Synthesis Module 112 to automatically or partially automatically synthesize the compounds in the Directed Diversity Library 108.

The Robotic Synthesis Instructions 204 identify Reagents 114 from a Reagent Inventory 116 that are to be mixed by the Synthesis Module 112. The Robotic Synthesis Instructions 204 also identify the manner in which such Reagents 114 are to be mixed by the Synthesis Module 112. For example, the Robotic Synthesis Instructions 204 can specify which Reagents 114 are to be mixed together. The Robotic Synthesis Instructions 204 can also specify chemical and/or physical conditions, such as temperature, length of time, stirring, etc. for mixing of the specified Reagents 114.

In one embodiment, compounds from the Directed Diversity Library 108 are manually synthesized and then delivered to the Analysis Module 118 for analysis. In one embodiment, a Compound Library 102 includes a single combinatorial chemical library that can be synthesized from approximately one hundred commercially available reagents that are suitable for generating thrombin inhibitors. Preferably, the Synthesis Module 112 combines these reagents using well-known synthetic chemistry techniques to synthesize inhibitors of the enzyme thrombin. Each inhibitor is generally composed of, but not restricted to, three chemical building blocks. Thus, the Directed Diversity Library 108 preferably comprises a plurality of thrombin inhibitors generally composed of, but not restricted to, three sites of variable structure (i.e. trimers).

The present invention, however, is not limited to this thrombin example. One skilled in the art will recognize that Compound Library 102 can include many other types of libraries. For example, the present invention is equally adapted and intended to generate other chemical compounds having other desired properties, such as paints, finishes, plasticizers, surfactants, scents, flavorings, bioactive compounds, drugs, herbicides, pesticides, veterinary products, etc., and/or lead compounds for any of the above. In fact, the present invention can generate chemical compounds having any useful properties that depend up structure, composition, or state.

As noted above, the compounds in the Directed Diversity Library 108, after being synthesized or retrieved from the Chemical Inventory 110, are provided to the Analysis Module 118 for analysis. Analysis can include chemical, biochemical, physical, and/or biological analysis.

Preferably, the Analysis Module 118 assays the compounds in the Directed Diversity Library 108 to obtain, for example, enzyme activity data, cellular activity data, toxicology data, and/or bioavailability data. Optionally, the Analysis Module 118 analyzes the compounds to identify which of the compounds were adequately synthesized and which of the compounds were not adequately synthesized. The Analysis Module 118 further analyzes the compounds to obtain other pertinent data, such as structure and electronic structure data.

The Analysis Module 118 also classifies any compounds that possess the Desired Properties 120 as Leads (lead compounds) 122. Alternatively, this function can be performed by another module such as, for example, the Experiment planner 130 or the Selector Module 106.

Analysis can be performed automatically, manually or semi-automatically/semi-manually.

The Analysis Module 118 generates Structure-Property Data 124 for the analyzed compounds. Structure-Property Data 124 can include structure-property and/ or structure-activity data. For example, Structure-Property Data 124 can include physical data, synthesis data, enzyme activity data, cellular activity data, toxicology data, bioavailability data, etc. The Structure-Property Data 124 is stored in a Structure-Property Database 126. The Structure-Property Data 124 is also provided to the Experiment Planner 130.

The Experiment Planner 130 receives current Structure-Property Data 124 from the Analysis Module 118 and Historical Structure-Property Data 128 from the Structure-Property Database 126. Historical Structure-Property Data 128 can include well known structure-property or structure-activity relationship data, collectively referred to as Structure-Property Relationships or SPR, pertaining to one or more relationships between the properties and activities of a compound and the chemical structure of the compound.

The Experiment Planner 130 also receives Compound Data 132 from the Compound Database 134, Reagent Data 136 from Reagent Database 138 and Desired Properties 120. Desired Properties 120 can be sent from an automated system or database (not shown) or from user input. In one embodiment, the Experiment Planner 130 also receives one or more Structure-Property Models 192 from one or more optional Structure-Property Model Generators 190. The Experiment Planner 130 uses the above inputs to generate one or more Selection Criteria 104 and Objective Functions 105.

Compound Data 132 and Reagent Data 136 permit the Experiment Planner 130 to include, for example, one or more of the following criteria in the Selection Criteria 104:

(1) the molecular diversity of a given set of compounds (as used herein, molecular diversity refers to a collective propensity of a set of compounds to exhibit a variety of a prescribed set of structural, physical, chemical and/or biological characteristics);

(2) the molecular similarity of a given compound or set of compounds with respect to one or more reference compounds (typically known leads);

(3) the cost of a given compound or set of compounds if these compounds are to be retrieved from the Chemical Inventory 110, or the cost of the Reagents 114 if the compound(s) are to be synthesized by the Synthesis Module 112;

(4) the availability of a given compound or set of compounds from the Chemical Inventory 110, or the availability of the Reagents 114 if the compound(s) are to be synthesized by the Synthesis Module 112;

(5) the predicted ease of synthesis of a given compound or set of compounds if these compound(s) are to be synthesized by the Synthesis Module 112;

(6) the predicted yield of synthesis of a given compound or set of compounds if these compound(s) are to be synthesized by the Synthesis Module 112;

(7) the method of synthesis of a given compound or set of compounds if these compound(s) are to be synthesized by the Synthesis Module 112;

(8) the predicted ability of a given compound or set of compounds to fit a receptor binding site;

(9) the predicted ability of a given compound or set of compounds to bind selectively to a receptor binding site;

(10) the predicted ability of a given compound or set of compounds to fit a 3-dimensional receptor map model;

(11) the predicted bioavailability of a given compound or set of compounds as determined by one or more bioavailability models;

(12) the predicted toxicity of a given compound or set of compounds as determined by one or more toxicity models; and/or

(13) other selection criteria that can be derived from information pertaining to a given compound or set of compounds and that can be used to guide the selection of the Directed Diversity Library 108 for the next iteration of the system of the present invention.

The optional Structure-Property Models 192 can be used by the Experiment Planner 130 to predict the properties of compounds in the Compound Library 102 whose real properties are hitherto unknown. The Structure-Property Models 192 are used by the Experiment Planner 130 to define and/or refine a set of Selection Criteria 104 that depend upon the predictions of one or more Structure-Property Models 192.

Structure-Property Models 192 permit the Experiment Planner 130 to include one or more of the following in Selection Criteria 104:

(1) the predicted ability of a given compound or set of compounds to exhibit one or more desired properties as predicted by one or more structural-property models;

(2) the predicted ability of a given compound or set of compounds to test the validity of one or more Structure-Property Models; and/or (3) the predicted ability of a given compound or set of compounds to discriminate between two or more Structure-Property Models (one or more Structure-Property models can be tested and evaluated in parallel).

The functionality of the Experiment Planner 130 can be achieved by an automated or partially automated process, or by a trained operator, aided or not by a computer. Further details of Structure-Property Models 192 are provided below.

The one or more new Selection Criteria 104 and Objective Functions 105 are sent to the Selector 106 which uses them to select a new Directed Diversity Library 108 for the next iteration of the present invention.

Thus, in summary, the compounds in the new Directed Diversity Library 108 are retrieved from the Chemical Inventory 110 and/or synthesized by the Synthesis Module 112. The Analysis Module 118 analyzes the new Directed Diversity Library 108 to obtain Structure-Property Data 124 pertaining to the compounds in the new Directed Diversity Library 108. The Experiment Planner 130 analyzes the new Structure-Property Data 124, Historical Structure-Property Data 128, and any of Compound Data 132, Reagent Data 136, Desired Properties 120 and Structure-Property Models 192, to identify a new set of Selection Criteria 104. The new set of Selection Criteria 104 can be used by the Selector 106 to select yet another Directed Diversity Library 108 for another iteration.

Thus, the present invention is an iterative system, method and/or computer program product for generating chemical entities, including new chemical entities, having a set of physical, chemical, and/or biological properties optimized towards a prescribed set of targets. During each iteration, a Directed Diversity Library 108 is generated, the compounds in the Directed Diversity Library 108 are analyzed, Structure-Property Models are optionally derived and elaborated, a list of Selection Criteria 104 are defined, and a new Directed Diversity Library 108 is selected for the next iteration.

Preferably, elements of the present invention are controlled by a data processing device (with or without operator input, intervention or control), such as a computer operating in accordance with software. Consequently, it is possible in the present invention to store massive amounts of data, and to utilize this data in a current iteration to generate Selection Criteria 104 for the next iteration.

In particular, since the elements of the present invention are controlled by a data processing device, it is possible to store the Structure-Property Data 124 obtained during each iteration. It is also possible to utilize the Historical Structure-Property Data 128 obtained during previous iterations, as well as other pertinent structure-property data obtained by other experiments, to generate Selection Criteria 104 for the next iteration. In other words, the selection of the Directed Diversity Library 108 for the next iteration is guided by the results of all previous iterations (or any subset of the previous iterations, as determined by user input, for example). Thus, the present invention "learns" from its past performance such that the present invention is "intelligent". As a result, the Leads 122 identified in subsequent iterations are better (i.e. exhibit physical, chemical, and/or biological properties closer to the prescribed values) that the Leads 122 identified in prior iterations.

In one embodiment of the present invention, the Compound Library 102 includes one or more combinatorial chemical libraries, comprised exclusively of compounds that can be synthesized by combining a set of chemical building blocks an a variety of combinations. According to this embodiment, the Synthesis Module 112 is used to robotically synthesize the Directed Diversity Library 108 during each iteration.

The integrated use of data processing devices (i.e. the Experiment Planner 130, the Selector 106, the Synthesis Protocol Generator 202, the Synthesis Module 112, and the Analysis Module 118) in the present invention enables the automatic or semi-automatic and intelligent synthesis and screening of very large numbers of chemical compounds.

Additional details of the Structure-Property Models 192, Selection Criteria 104, Objective Functions 105, Experiment Planner 130 and the Selector 106 are now provided.

3. Structure-Property Models 192

In one embodiment of the present invention, one or more Structure-Property Model Generators 190 generate Structure-Property Models 192 that conform to observed data. The Structure-Property Models 192 are used by the Experiment planner 130 to generate Selection Criteria 104 and/or Objective Functions 105.

Figure 8:
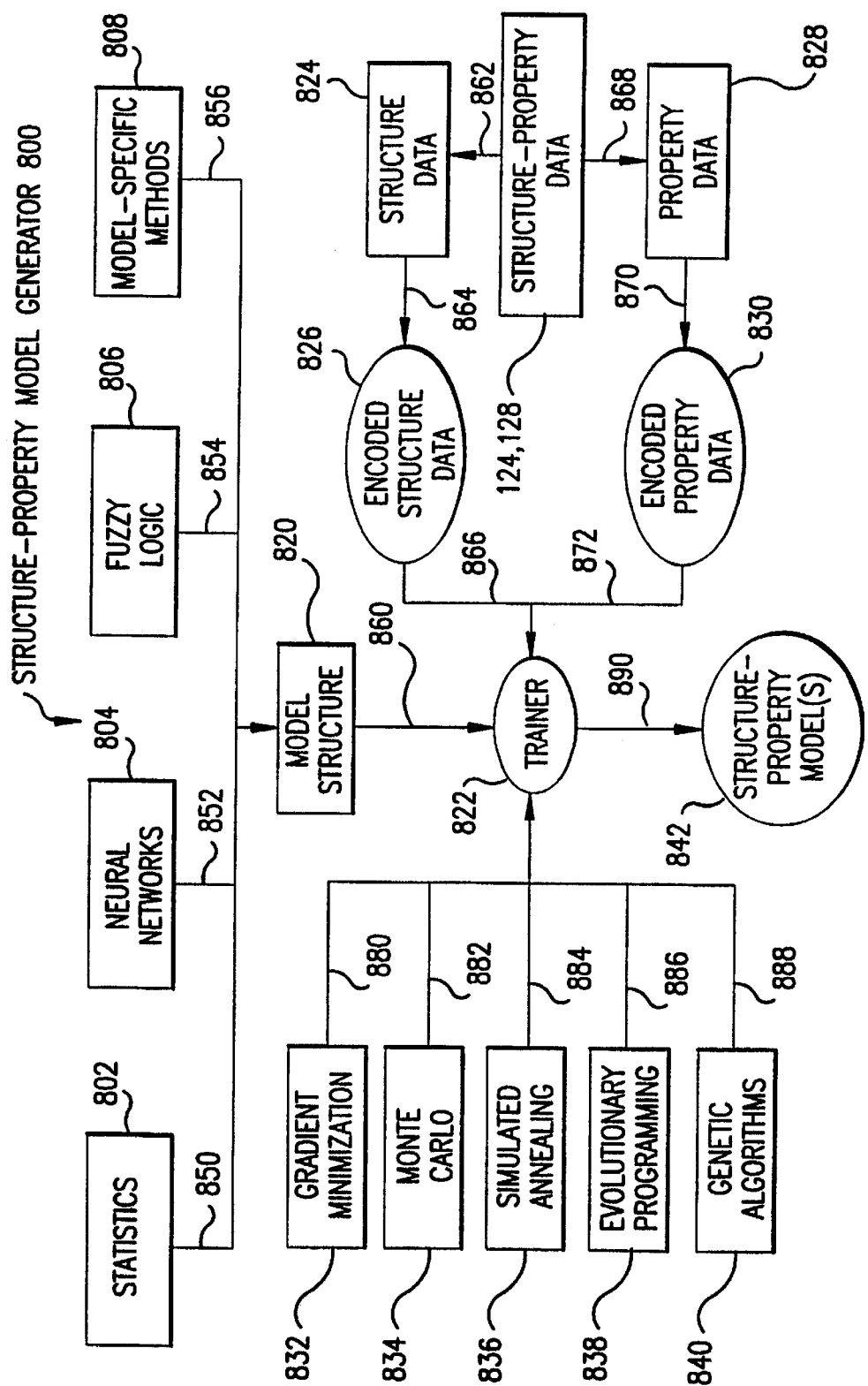
FIG. 8 is a flow diagram depicting the flow of data among elements of a structure-property model generator that can be employed by a lead generation system.

Referring to FIG. 8, one embodiment of a Structure-Property Model Generator 190 is illustrated as Structure-Property Model Generator 800. The Structure-Property Model Generator 800 defines a Model Structure 820 based on Statistics 802, Neural Networks 804, Fuzzy Logic 806, and/or other Model-Specific Methods 808.

Model-Specific Methods 808 refer to methods that are specific to the application domain of the model. Examples of such Model-Specific Methods 808 are methods that compute the energy of a particular molecular conformation or receptor-ligand complex such as an empirical force field or a quantum-mechanical method, methods that align the 3-dimensional structures of two or more chemical compounds based on their shape, electronic fields and/or other criteria, methods that predict the affinity and binding conformation of a ligand to a particular receptor binding site, methods that construct receptor models based on the 3-dimensional structures of known ligands, etc. Examples of such Model-Specific Methods 808 are described in greater detail below.

The Model Structure 820 can combine elements of Statistics 802, Neural Networks 804, Fuzzy Logic 806, and/or Model-Specific Methods 808. Such Model Structures 820 are hereafter referred to as Hybrid Model Structures or Hybrid Models. An example of such a Hybrid Model Architecture 820 is a Model Architecture that combines elements of Neural Networks 804 and Fuzzy Logic 806, hereafter referred to as a Neuro-Fuzzy Model Architecture or Neuro-Fuzzy Model. An example of a Neuro-Fuzzy Model Architecture is discussed in greater detail below.

One embodiment of a Structure-Property Model Generator 800 includes a Trainer 822 that generates one or more Structure-Property Models 842 for a given Model Architecture 820. The Trainer 822 optimizes a particular Model Structure 820 using selected Structure-Property Data 124 and 128 from the Structure-Property Database 126, as determined by user input, for example. Preferably, the Trainer 822 optimizes the Model Structure 820 by minimizing the error between the actual properties of selected compounds, as determined by the Analysis Module 118 (Structure-Property Data 124, 128), and the predicted properties of the compounds as determined by the Structure-Property Model 842. The error is referred to hereafter as the Structure-Property Prediction Error or Prediction Error.

The process of minimizing the Prediction Error shall hereafter be referred to as Training. Preferably, the Trainer 822 minimizes the Prediction Error using a search/optimization method such as Gradient Minimization 832, Monte-Carlo Sampling 834, Simulated Annealing 836, Evolutionary Programming 838, and/or a Genetic Algorithm 840. Alternatively, the Trainer 822 minimizes the Prediction Error using a hybrid search/optimization method that combines elements of Gradient Minimization 832, Monte-Carlo Sampling 834, Simulated Annealing 836, Evolutionary Programming 838, and/or a Genetic Algorithm 840. An example of a hybrid method is a method that combines Simulated Annealing 836 with Gradient Minimization 832. Another example of a hybrid method is a method that combines Monte-Carlo Sampling 834 with Gradient Minimization 832. Examples of such methods are described in greater detail below.

Preferably, the Structure-Property Data 124, 128 are divided into Structure Data 824 and Property Data 828. Structure Data 824 and Property Data 828 are preferably encoded as Encoded Structure Data 826 and Encoded Property Data 830. Encoding should be of a form that is appropriate for the particular Model Structure 820. The Encoded Structure Data 826 and Encoded Property Data 830 are used by the Trainer 822 to derive one or more final Structure-Property Models 842. The Trainer 822 can employ Gradient Minimization 832, Monte-Carlo Sampling 834, Simulated Annealing 836, Evolutionary Programming 838, and/or a Genetic Algorithm 840. The Trainer 822 trains the Model Structure 820 using a suitably encoded version of the Structure-Property Data 124, 128, or a selected subset of the Structure-Property Data 124, 128, as determined by user-input, for example.

The Trainer 822 generates one or more Structure-Property Models 842 for a given Model Structure 820. In one embodiment, Structure-Property Models 842 are represented as a linear combination of basis functions of one or more molecular features (descriptors). The descriptors collectively represent the Encoded Structure Data 826.

To illustrate the present invention, several example embodiments and implementations of the Structure-Property Model Generator 800 shall now be discussed in detail. These examples are provided to illustrate the present invention. The present invention is not limited to these examples.

a. Statistical Models

A Statistical Module 802 can define a Statistical Model Structure 820. When the trainer optimizes the Statistical Model Structure 820, the resultant Structure-Property Model 842 is referred to as a Statistical Structure-Property Model 842.

In one embodiment, Structure-Property Models 192 are represented as a linear combination of basis functions of one or more molecular features (descriptors). The descriptors can include topological indices, physicochemical properties, electrostatic field parameters, volume and surface parameters, etc. The number of descriptors can range from a few tens to tens of thousands. For example, the descriptors can include, but are not limited to, molecular volume and surface areas, dipole moments, octanol-water partition coefficients, molar refractivities, heats of formation, total energies, ionization potentials, molecular connectivity indices, substructure keys, hashed fingerprints, atom pairs and/or topological torsions, atom layers, 2D and 3D autocorrelation vectors, 3D structural and/or pharmacophoric keys, electronic fields, etc.

Such descriptors and their use in the fields of Quantitative Structure-Activity Relationships (QSAR) and molecular diversity are reviewed in Kier, L. B. and Hall L. H., *Molecular Connectivity in Chemistry and Drug Research*, Academic Press, New York (1976); Kier, L. B. and Hall L. H., *Molecular Connectivity in Structure-Activity Analysis*, Research Studies Press, Wiley, Letchworth (1986); Kubinyi, H., *Methods and Principles in Medicinal Chemistry*, Vol. 1, VCH, Weinheim (1993); and Agrafiotis, D. K., *Encyclopedia of Computational Chemistry*, Wiley (in press), the contents of which are incorporated herein by reference.

In one embodiment, the coefficients of the linear combination of the basis functions of Statistical Structure-Property Models 842 are determined using linear regression techniques. If many features are used, linear regression can be combined with principle component analysis, factor analysis, and/or multi-dimensional scaling. These are well known techniques for reducing the dimensionality and extracting the most important features from a large table.

In one embodiment, the basis functions and/or features used by the Trainer 822 to optimize the Statistical Structure-Property Models 842 are selected using Monte-Carlo Sampling 834, Simulated Annealing 836, Evolutionary Programming 838, and/or a Genetic Algorithm 840. A method for selecting the basis functions and/or features using a Genetic Algorithm 840, known as a genetic function approximation (GFA), is described in Rogers and Hopfinger, *J. Chem. Inf. Comput. Sci.*, 34: 854 (1994) incorporated herein by reference in its entirety.

In the GFA algorithm, a Structure-Property Model 842 is represented as a linear string that encodes the features and basis functions employed by the model. A population of linearly encoded Structure-Property Models 842 is then initialized by a random process, and allowed to evolve through the repeated application of genetic operators, such as crossover, mutation and selection. Selection is based on the relative fitness of the models, as measured by a least-squares error procedure, for example. Friedman's lack-of-fit algorithm, described in J. Friedman, Technical Report No. 100, Laboratory for Computational Statistics, Department of Statistics, Stanford University, Stanford, Calif., November 1988, herein incorporated by reference in its entirety, or other suitable metrics well known to persons skilled in the art, can also be used. GFA can build models using linear polynomials as well as higher-order polynomials, splines and Gaussians. Upon completion, the procedure yields a population of models, ranked according to their fitness score.

Another method for selecting basis functions and/or features is described in Luke, *J. Chem. Info. Comput. Sci.*, 34: 1279 (1994), incorporated herein by reference in its entirety. This method is similar to the GFA method of Rogers and Hopfinger described above, but uses Evolutionary Programming 838 instead of a Genetic Algorithm 840 to control the evolution of the population of models.

Alternatively, the basis functions and/or features can be selected using a Monte-Carlo Sampling 834 or Simulated Annealing 834 technique. In this embodiment, an initial model is generated at random, and is gradually refined by a series of small stochastic 'steps'. Here, the term 'step' is taken to imply a stochastic (random or semi-random) modification of the model's underlying structure.

As in the GFA algorithm, the model in this embodiment is also defined as a linear combination of basis functions, whose coefficients are determined by linear regression. During each step, the model is modified by making a 'small' stochastic step. For example, the model can be modified by inserting a new basis function, by removing an existing basis function, by modifying an existing basis function (i.e. by modifying one or more of the features and/or parameters associated with that particular basis function), and/or by swapping features and/or parameters between two (compatible) basis functions.

The quality of the model is assessed using a least-squares error criterion. Alternatively, Friedman's lack-of-fit criterion, or any other suitable error criterion can be used. At the end of each step, the new model is compared to the old model using the Metropolis criterion. Alternatively, any other suitable comparison criterion can be used. If the new model is approved, it replaces the old model and the process is repeated. If the new model is not approved, the old model is retained as the current model, and the process is repeated. This general process is controlled by a Monte-Carlo Sampling protocol 834, a Simulated Annealing protocol 836, or variants thereof, which are well known to the people skilled in the art.

During the training process, the Trainer 822 can be configured to retain a list of models according to some predefined criteria. For example, the Trainer 822 can be configured to retain the ten best Structure-Property Models 842 discovered during the simulation. Alternatively, the Trainer 822 can be configured to retain the ten best Structure-Property Models 842 discovered during the simulation, which differ from each other by some predetermined amount. The difference between two models can be defined 'genotypically' or 'phenotypically'. A 'genotypical' comparison between two models involves a comparison of their underlying structure (i.e. the basis functions and/or coefficients used to represent the Structure-Property Models 842). Conversely, a 'phenotypical' comparison between two models involves a comparison based on their respective predictions.

b. Neural Network Models

The Structure-Property Model Generator 800 can generate Structure-Property Models 842 based on Neural Networks 804. Neural Networks 804 are physical cellular systems that can acquire, store, and utilize experimental knowledge. Neural Networks 804 are extensively reviewed in Haykin, *Neural Networks. A Comprehensive Foundation*, MacMillan, New York (1994), incorporated herein by reference in its entirety.

As in the functional models described above, Structure Data 824 can be encoded using one or more molecular features (descriptors). Molecular features collectively represent the Encoded Structure Data 826. Molecular features can include topological indices, physicochemical properties, electrostatic field parameters, volume and surface parameters, etc., and their number can range from a few tens to tens of thousands. For example, these features can include, but are not limited to, molecular volume and surface areas, dipole moments, octanol-water partition coefficients, molar refractivities, heats of formation, total energies, ionization potentials, molecular connectivity indices, substructure keys, hashed fingerprints, atom pairs and/or topological torsions, atom layers, 2D and 3D auto-correlation vectors, 3D structural and/or pharmacophoric keys, electronic fields, etc. If many features are used, neural network training can be combined with principle component analysis, factor analysis, and/or multi-dimensional scaling, which are well known techniques for reducing the dimensionality and extracting the most important features from a large table.

One embodiment of a Neural Network Model Structure 820 is a Multi-Layer Feed-Forward Neural Network or Multi-Layer Perceptron, trained using the error back-propagation algorithm. Alternatively, the Multi-Layered Perceptron can be trained using Monte-Carlo Sampling 834, Simulated Annealing 836, Evolutionary Programming 838, and/or a Genetic Algorithm 840. In general, Neural Network training is the process of adjusting the number of neurons, synaptic weights, and/or transfer functions in the input, output and hidden layers of the Neural Network, so that the overall prediction error is minimized. Many variants of such training algorithms have been reported, and are well known to those skilled in the art.

As in the functional models described above, the Trainer 822 can be configured to retain more than one Neural Network Models 842 during the training phase (flow arrow 890 in FIG. 8). For example, the Trainer 822 can be configured to retain the ten best Neural Network Models 842 discovered during the training phase. Alternatively, the Trainer 822 can be configured to retain the ten best Neural Network Models 842 discovered during training, which differ from each other by some predetermined amount. Again, the difference between two models can be defined 'genotypically' or 'phenotypically', i.e. by comparing the models based either on their internal structure, or their predictions.

i. Generalized Regression Neural Networks

Another embodiment of a Neural Network Model Structure 820 is a Generalized Regression Neural Network Model Structure (or Generalized Regression Neural Network). Generalized Regression Neural Networks are described in Specht, D. *IEEE Trans. Neural Networks*, 2(6): 568 (1991), and Masters, T., *Advanced Algorithms for Neural Networks*, Wiley (1995), incorporated herein by reference.

Figure 9:
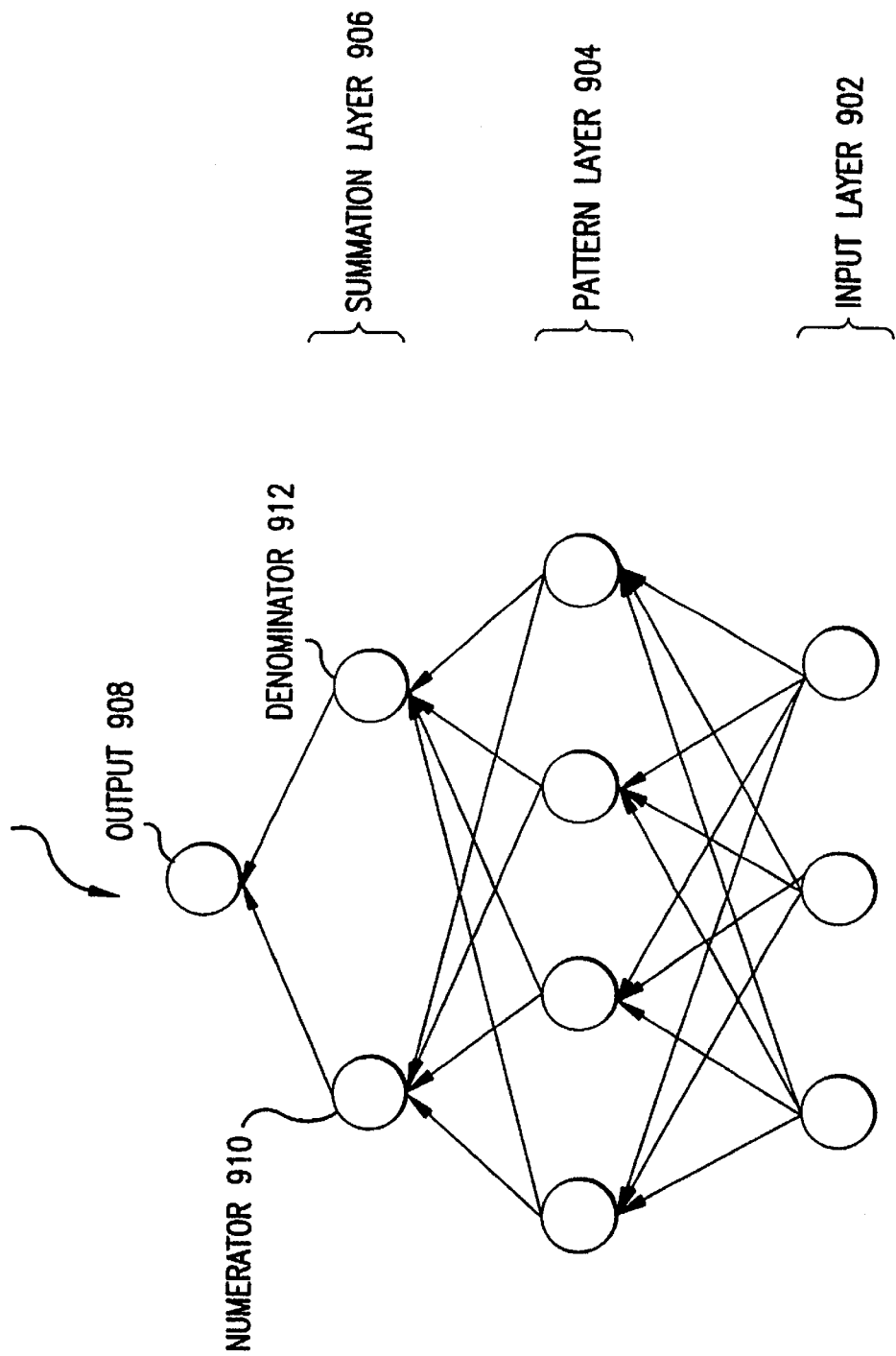
FIG. 9 is an illustration of a generalized regression neural network model that can be generated by the structure-property model generator illustrated in FIG. 8 and that can employ a K-Nearest-Neighbor classifiers.

An example of a Generalized Regression Neural Network 900 is shown in FIG. 9. A Generalized Regression Neural Network 900 is comprised of four layers of neurons (units). The first layer is the Input Layer 902, the second layer is the Pattern Layer 904, the third layer is the Summation Layer 906, and the fourth layer is the Output Layer 908, which is comprised of a single unit.

The Pattern Layer 904 contains one unit per input-output pair or structure-property pair (referred to hereafter as a Training Case). The collection of all Training Cases used in the Pattern Layer 904 is hereafter referred to as the Training Set. In the example shown in FIG. 9, there are four Training Cases. The input vector (or input case, which in the example shown in FIG. 9 consists of 3 variables) is simultaneously presented to all units in the Pattern Layer 904. Each of these units computes a distance measure separating the Training Case represented by that unit from the input case. This distance is acted on by the transfer function associated with that unit, to compute the output of that particular unit. The transfer function is also referred to as an activation function or kernel.

The Summation Layer 906 of the Generalized Regression Neural Network 900 (i.e. the third layer) is comprised of two units. The first unit is called the Numerator 910, and the second unit is called the Denominator 912. Each unit in the Pattern Layer 904 is fully connected to the Numerator 910 and Denominator 912 units in the Summation Layer 906. Both the Numerator 910 and Denominator 912 units are simple summation units, i.e. they accumulate the input received from all units in the Pattern Layer 904. For the Denominator 912 unit, the weight vector is unity, so a simple sum is performed. For the Numerator 910 unit, the weight connecting each pattern unit is equal to the value of the dependent variable for the training case of that pattern unit (i.e. the output in the input-output pair, or the property in the structure-property pair).

The output of the Numerator 910 and Denominator 912 units in the Summation Layer 906 are forwarded to the Output unit 908. The Output unit 908 divides the output of the Numerator 910 unit by the output of the Denominator 912 unit, to compute the output of the network for a particular input case.

The activation used by the units in the Pattern Layer 904 is typically a Parzen Window. Parzen Windows is a well known method for estimating a univariate or multivariate probability density function from a random sample. They are described in Parzen, *Annals Math. Stat.*, 33: 1065 (1962), and Cacoullos, *Annals Inst. Stat. Meth.*, 18(2): 179 (1966), incorporated herein by reference in their entirety. The Parzen Window is a weight function w(d) that has its largest value at d=0, and decreases rapidly as the absolute value of d increases. Examples of such weight functions are histogram bins, Gaussians, triangular functions, reciprocal functions, etc. If the number of input variables (features) exceeds one, the Parzen Window can involve different scaling parameters for each input variable. Thus, a Parzen Window can be configured to perform feature scaling in the vicinity of the Training Case on which it is centered. If the Parzen Windows associated with each Training Case share common feature weights, the Generalized Regression Neural Network 900 is said to be globally weighted. Conversely, if the Parzen Windows associated with each Training Case do not share common feature weights, the Generalized Regression Neural Network 900 is said to be locally weighted.

Referring back to FIG. 8, a Generalized Regression Neural Network 900 can be trained to minimize the prediction error using Gradient Minimization 832, Monte-Carlo Sampling 834, Simulated Annealing 836, Evolutionary Programming 838, and/or a Genetic Algorithm 840. Alternatively, the Generalized Regression Neural Network 900 can be trained to minimize the prediction error using a combination of Gradient Minimization 832, Monte-Carlo Sampling 834, Simulated Annealing 836, Evolutionary Programming 838, and/or a Genetic Algorithm 840.

The training process involves adjusting the parameters of the activation function associated with each unit in the Pattern Layer 904 to minimize the mean prediction error for the entire Training Set, or some other suitable error criterion. During training, the input-output pairs in the Training Set are presented to the network, and a prediction error for the entire Training get is computed. In particular, each Training Case is presented to each of the units (Training Cases) in the Pattern Layer 904, and the output of these units are summed by the units in the Summation Layer 906. The output of the summation units 910 and 912 are then divided to compute the output of the network for that particular Training Case.

This process is repeated for each Training Case in the Training Set. The parameters of the transfer functions are then adjusted so that the prediction error is reduced. This process is repeated until the prediction error for the entire Training Set is minimized, within some prescribed tolerance. Alternatively, the process is repeated for a prescribed number of cycles (as determined by user input, for example), even though the prediction error for the entire Training Set may not be at a minimum, within a prescribed tolerance. Preferably, during the training phase, each Training Case is not presented to itself, i.e. the output of each Training Case is computed based on every Training Case other than itself. Thus, it is said that the resulting Generalized Regression Neural Network Models 842 are cross-validated, in the sense that they were designed to resist over fitting.

If the number of features is large, the Trainer 822 can also perform feature selection in addition to scaling (i.e. adjusting the parameters of the transfer functions). Feature selection refers to the process of selecting a subset of features, and applying the Generalized Regression Neural Network 900 algorithm only on that subset of features.

For example, in one embodiment, the Generalized Regression Neural Network 900 is trained using a Monte-Carlo Sampling 834 or Simulated Annealing 836 algorithm. In this embodiment, an initial model is generated at random, by selecting a random set of features and randomizing the transfer functions associated with each Training Case.

The model is then gradually refined by a series of small stochastic 'steps'. Here, the term 'step' is taken to imply a stochastic (random or semi-random) modification of the model's underlying structure. For example, the model can be modified by inserting a new feature, by removing an existing feature, by modifying an existing feature weight if the model is globally weighted, and/or by modifying a randomly chosen transfer function (i.e. by modifying one or more of the parameters associated with that particular transfer function, such as a feature weight). After the 'step' is performed, the quality of the resulting model is assessed, and the new model is compared to the old model using the Metropolis criterion. Alternatively, any other suitable comparison criterion can be used. If the new model is approved, it replaces the old model and the process is repeated. If the new model is not approved, the old model is retained as the current model, and the process is repeated.

This general process is controlled by a Monte-Carlo Sampling protocol 834, a Simulated Annealing protocol 836, or variants thereof, which are well known to people skilled in the art. However, it should be understood that the system of the present invention is not limited to these embodiments. Alternatively, the Generalized Regression Neural Network 900 can be trained using Evolutionary Programming 838, Genetic Algorithms 840, or any other suitable search/optimization algorithm. The implementation of these methods should be straightforward to persons skilled in the art.

The training of a Generalized Regression Neural Network 900 using the method described above involves (N−1)*(N−1) distance comparisons during each optimization cycle, where N is the number of Training Cases. That is, in order to compute the prediction error for the entire Training Set, each Training Case must be presented to all other (N−1) Training Cases in the network. Thus, it is said that the system operating in the manner described above exhibits quadratic time complexity.

For large Training Sets, such as those anticipated in a typical operation of the system of the present invention, this process can become computationally intractable. To remedy this problem, a preferred embodiment of the system of the present invention uses a hybrid approach that combines Generalized Regression Neural Networks 900 with K-Nearest-Neighbor classifiers.

K-Nearest-Neighbor prediction is a well known technique for property prediction and classification. It is described in detail in Dasarathy, *Nearest Neighbor (NN) Norms: NN pattern classification techniques*, IEEE Computer Society Press, Los Alamitos, Calif. (1991), incorporated herein by reference in its entirety. K-Nearest-Neighbor prediction forms the basis of many 'lazy learning' algorithms, that are commonly used in artificial intelligence and control. The K-Nearest-Neighbor algorithm predicts the output (property) of a particular input query by retrieving the K nearest (most similar) Training Cases to that query, and averaging their (known) outputs according to some weighting scheme. Therefore, the quality of K-Nearest-Neighbor generalization depends on which Training Cases are considered most similar, which is, in turn, determined by the distance function.

In the embodiment described herein, Generalized Regression Neural Networks 900 are combined with K-Nearest-Neighbor classifiers, to generate a hybrid Model Structure 820 referred to hereafter as a Nearest Neighbor Generalized Regression Neural Network. The operation of a Nearest Neighbor Generalized Regression Neural Network is similar to that of a regular Generalized Regression Neural Network, except that the query (input case) is not presented to all Training Cases in the Pattern Layer 904. Instead, the query is presented to the K nearest Training Cases in the Pattern Layer 904, as determined by a suitable distance metric.

To accelerate the performance of a Nearest Neighbor Generalized Regression Neural Network, the K nearest neighbors are retrieved using a nearest neighbor detection algorithm such as a k–d tree (Bentley, *Comm. ACM*, 18(9): 509 (1975), Friedman et al., *ACM Trans. Math. Soft.*, 3(3): 209 (1977)). Alternatively, any other suitable algorithm can be used including, but not limited to, ball trees (Omohundro, *International Computer Science Institute Report TR*-89-063, Berkeley, Calif. (1989)), bump trees (Omohundro, Advances in *Neural Information Processing Systems* 3, Morgan Kaufmann, San Mateo, Calif. (1991)), gridding, and/or Voronoi tesselation (Sedgewick, *Algorithms in C*, Addison-Wesley, Princeton (1990). The contents of all of the aforementioned publications are incorporated herein by reference.

The Generalized Regression Neural Network 900 can be trained in multiple phases using different optimization algorithms (i.e. Monte-Carlo Sampling 834, Simulated Annealing 836, Evolutionary Programming 838, and/or Genetic Algorithms 840), and/or different kernel parameters and number of nearest-neighbors during each phase. For example, the Generalized Regression Neural Network 900 can be initially trained to perform feature detection using Simulated Annealing 836, ten nearest neighbors, a uniform kernel (i.e. the same kernel for all Training Cases), and a common scaling factor for all features. The resulting (partially optimized) network can then be further refined using Gradient Minimization 832 using fifty nearest neighbors, a uniform kernel, and a different scaling factor for each feature. Any number of phases and training schemes can be used as appropriate.

As in the functional models and multi-layer perceptrons described above, the Trainer 822 can be configured to retain more than one Generalized Regression Neural Network Models 842 during the training phase (flow arrow 890 in FIG. 8). For example, the Trainer 822 can be configured to retain the ten best Generalized Regression Neural Network Models 842 discovered during the training phase. Alternatively, the Trainer 822 can be configured to retain the ten best Generalized Regression Neural Network Models 842 discovered during training, which differ from each other by some predetermined amount. Again, the difference between two models can be defined 'genotypically' or 'phenotypically', i.e. by comparing the models based either on their internal structure, or their predictions.

C. Fuzzy Logic Models

The Structure-Property Model Generator 800 can generate Structure-Property Models 842 based on Fuzzy Logic 806. Fuzzy Logic was developed by Zadeh (Zadeh, *Information and Control*, 8: 338 (1965); Zadeh, *Information and Control*, 12: 94 (1968)) as a means of representing and manipulating data that is fuzzy rather than precise. The aforementioned publications are incorporated herein by reference in their entirety.

Central to the theory of Fuzzy Logic is the concept of a fuzzy set. In contrast to a traditional crisp set where an item either belongs to the set or does not belong to the set, fuzzy sets allow partial membership. That is, an item can belong to a fuzzy set to a degree that ranges from 0 to 1. A membership degree of 1 indicates complete membership, whereas a membership value of 0 indicates non-membership. Any value between 0 and 1 indicates partial membership. Fuzzy sets can be used to construct rules for fuzzy expert systems and to perform fuzzy inference.

Usually, knowledge in a fuzzy system is expressed as rules of the form "if x is A, then y is B", where x is a fuzzy variable, and A and B are fuzzy values. Such fuzzy rules are stored in a fuzzy rule base or fuzzy knowledge base describing the system of interest. Fuzzy Logic 806 is the ability to reason (draw conclusions from facts or partial facts) using fuzzy sets, fuzzy rules, and fuzzy inference. Thus, following Yager's definition, a fuzzy model is a representation of the essential features of a system by the apparatus of fuzzy set theory (Yager and Filev, *Essentials of Fuzzy Modeling and Control*, Wiley (1994)). The aforementioned publication is incorporated herein by reference in its entirety.

Fuzzy Logic 806 has been employed to control complex or adaptive systems that defy exact mathematical modeling. Applications of fuzzy logic controllers range from cement-kiln process control, to robot control, image processing, motor control, camcorder auto-focusing, etc. However, as of to date, there has been no report on the use of Fuzzy Logic 806 for chemical structure-property prediction. A preferred embodiment of a Structure-Property Model Generator 800 using Fuzzy Logic 806 shall now be described in detail.

In one embodiment, the Structure-Property Model Generator 800 generates Fuzzy Structure-Property Models 842, i.e. models that represent the essential features of the system using the apparatus of fuzzy set theory. In particular, a Fuzzy Structure-Property Model 842 makes predictions using fuzzy rules from a fuzzy rule base describing the system of interest. A fuzzy rule is an IF-THEN rule with one or more antecedent and consequent variables. A fuzzy rule can be single-input-single-output (SISO), multiple-input-single-output (MISO), or multiple-input-multiple-output (MIMO). A fuzzy rule base is comprised of a collection of one or more such fuzzy rules. A MISO fuzzy rule base is of the form:

IF $x_1$ is $X_{11}$ AND $x_2$ is $X_{12}$ AND ... AND $x_n$ is $X_{1n}$ THEN y is $Y_1$

ALSO

IF $x_1$ is $X_{21}$ AND $x_2$ is $X_{22}$ AND ... AND $x_n$ is $X_{2n}$ THEN y is $Y_2$

ALSO

...

ALSO

IF $x_1$ is $X_{r1}$ AND $x_2$ is $X_{r2}$ AND ... AND $x_n$ is $X_{rn}$ THEN y is $Y_r$, where $x_1, \ldots, x_n$ are the input variables, y is the output (dependent) variable, and $X_{ij}, Y_i$, i=(1, ..., r), j=(1, ..., n)

are fuzzy subsets of the universes of discourse of $X_1, \ldots, X_n$, and $Y_1, \ldots, Y_n$, respectively. The fuzzy model described above is referred to as a linguistic model.

An example of a fuzzy structure-activity rule is:

IF molecular weight is high AND logP is low THEN activity is low where 'high' and 'low' are fuzzy sets in the universe of discourse of molecular weight, logP, and activity.

Alternatively, a Takagi-Sugeno-Kang (TSK) model can be used. A TSK fizzy rule base is of the form:

IF $x_1$ is $X_{11}$ AND $x_2$ is $X_{12}$ AND ... AND $x_n$ is $X_{1n}$ THEN $y=b_{10}+b_{11n1}+ \ldots +b_{1n} x_n$

ALSO

IF $x_1$ is $X_{21}$ AND $x_2$ is $X_{22}$ AND ... AND $x_n$ is $X_{2n}$ THEN $y=b_{20}+b_{21x1}+ \ldots +b_{2n} x_n$

ALSO

. . .

ALSO

IF $x_1$ is $X_{r1}$ AND $x_2$ is $X_{r2}$ AND ... AND $x_n$ is $X_m$ THEN $y=b_{r0}+b_{r1x1}+ \ldots +b_m x_n$ Thus, unlike a linguistic model that involves fuzzy consequents, a TSK model involves functional consequents, typically implemented as a linear function of the input variables.

Figure 10:
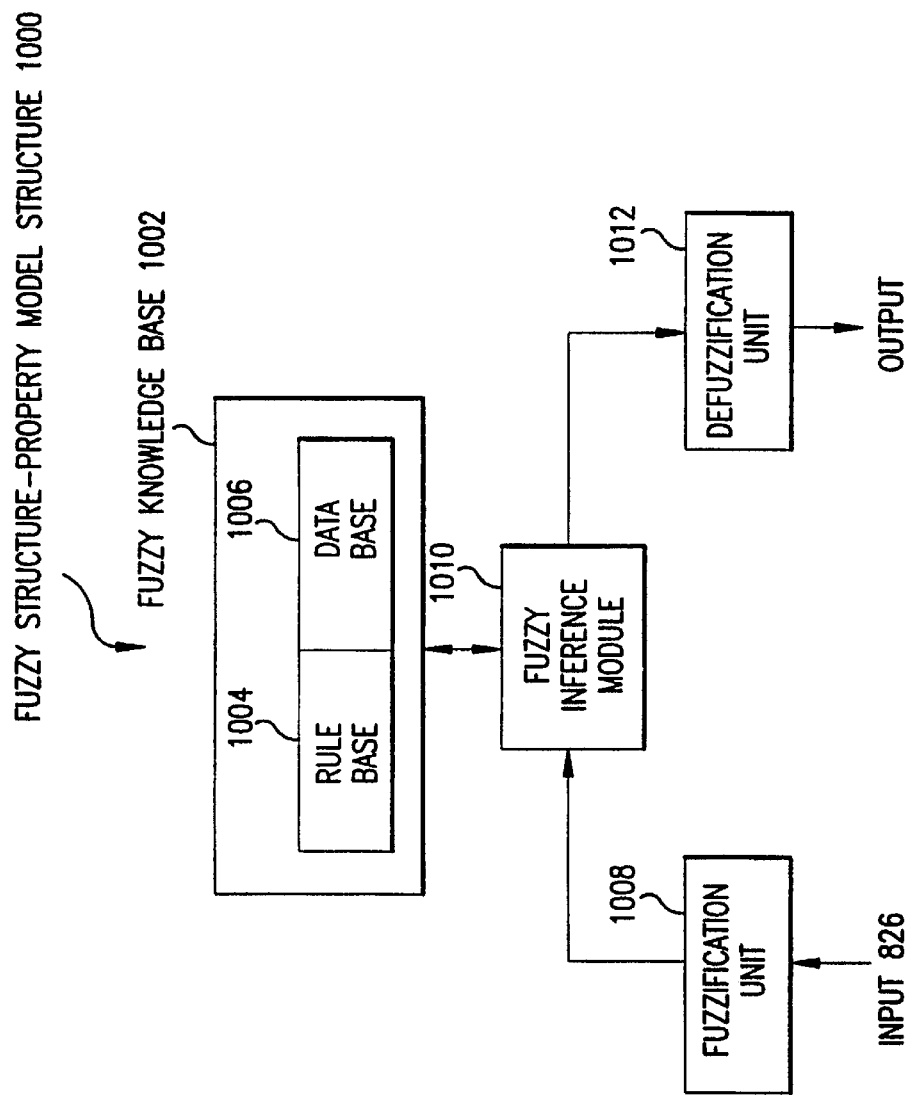
FIG. 10 is a flow diagram depicting the flow of data among elements of a fuzzy structure-property model than can be generated by the structure-property model generator illustrated in FIG. 8.

Referring to FIG. 10, a Fuzzy Structure-Property Model 1000 is illustrated. In this embodiment, the Fuzzy Knowledge Base 1002 is comprised of a Rule Base 1004 and a Data Base 1006. The Data Base 1006 defines the membership functions of the fuzzy sets used as values for each system variable, while the Rule Base 1004 is a collection of fuzzy rules of the type described above. The system variables are of two main types: input variables and output variables.

In one embodiment, the input variables in a Fuzzy Structure-Activity Model 842 can be molecular features (descriptors). Such molecular features, which collectively represent the Encoded Structure Data 826, can include topological indices, physicochemical properties, electrostatic field parameters, volume and surface parameters, etc., and their number can range from a few tens to tens of thousands.

For example, these features can include, but are not limited to, molecular volume and surface areas, dipole moments, octanol-water partition coefficients, molar refractivities, heats of formation, total energies, ionization potentials, molecular connectivity indices, substructure keys, hashed fingerprints, atom pairs and/or topological torsions, atom layers, 2D and 3D auto-correlation vectors, 3D structural and/or pharmacophoric keys, electronic fields, etc.

If many features are used, Fuzzy Logic 806 can be combined with principle component analysis, factor analysis, and/or multi-dimensional scaling, which are well known techniques for reducing the dimensionality and extracting the most important features from a large table.

In one embodiment, the input variables (i.e. the Encoded Structure Data 826, which are usually crisp) are first converted into fuzzy sets by the Fuzzification Unit 1008 using the fuzzy set definitions in the Data Base 1006. Then, the Fuzzy Inference Module 1010 evaluates all the rules in the Rule Base 1004 to produce the output, using the method described below. In particular, the Fuzzy Inference Module 1010 performs the following steps:

(1) determines the degree of match between the fuzzified input data and the fuzzy sets defined for the input variables in the Data Base 1006;

(2) calculates the firing strength of each rule based on the degree of match of the fuzzy sets computed in step 1 and the connectives used in the antecedent part of the fuzzy rule (i.e. AND, OR, etc.); and (3) derives the output based on the firing strength of each rule computed in step 2 and the fuzzy sets defined for the output variable in the Data Base 1006.

If the Fuzzy Structure-Property Model is a linguistic model, the fuzzy output of the Fuzzy Inference Module 1010 is finally defuzzified by the Defuzzification Unit 1012, using the output fuzzy set definitions in the Data Base 1006, and a defuzzification strategy such as the mean-of-maximum method. Alternatively, the center-of-area or any other suitable deffuzification method can be used.

Referring back to FIG. 8, the Trainer 822 of the Fuzzy Structure-Property Model Generator 800 preferably trains the Fuzzy Knowledge Base 1002 using Gradient Minimization 832, Monte-Carlo Sampling 834, Simulated Annealing 836, Evolutionary Programming 838, and/or a Genetic Algorithm 840, in order to minimize the overall prediction error for a prescribed set of Training Cases. The Trainer 822 can use a pre-existing Fuzzy Knowledge Base 1002 or may construct one directly from the Structure-Property Data 124, 128. Training is the process of creating, modifying and/or refining the fuzzy set definitions and fuzzy rules in the Fuzzy Knowledge Base 1002.

For example, in a preferred embodiment, the Fuzzy Knowledge Base 1002 is trained using a Monte-Carlo Sampling 834 or Simulated Annealing 836 algorithm. In this embodiment, an initial model is generated at random, by selecting a random set of rules and randomizing the membership functions associated with each input variable. The model is then gradually refined by a series of small stochastic 'steps'. Here, the term 'step' is taken to imply a stochastic (random or semi-random) modification of the model's underlying structure.

For example, the model can be modified by inserting a new rule, by removing an existing rule, by modifying an existing rule (i.e. by inserting or removing a variable from the antecedent part of the fuzzy rule), by modifying, the membership function of an existing fuzzy set, and/or by modifying the number of fuzzy partitions of a fuzzy variable (i.e. by increasing or decreasing the number of fuzzy partitions of the fuzzy variable). After the 'step' is performed, the quality of the resulting model is assessed, and the new model is compared to the old model using the Metropolis criterion. Alternatively, any other suitable comparison criterion can be used. If the new model is approved, it replaces the old model and the process is repeated. If the new model is not approved, the old model is retained as the current model, and the process is repeated.

This general process is controlled by a Monte-Carlo Sampling protocol 834, a Simulated Annealing protocol 836, or variants thereof, which are well known to people skilled in the art. However, it should be understood that the system of the present invention is not limited to these embodiments. Alternatively, the Fuzzy Knowledge Base 1002 can be trained using Evolutionary Programming 838, Genetic Algorithms 840, or any other suitable search/optimization algorithm. The implementation of these methods should be straightforward to persons skilled in the art.

As in the functional and neural network models described above, the Trainer 822 can be configured to retain more than one Fuzzy Structure-Property Models 842 during the training phase (flow arrow 890 in FIG. 8). For example, the Trainer 822 can be configured to retain the ten best Fuzzy Structure-Property Models 842 discovered during the training phase. Alternatively, the Trainer 822 can be configured to retain the ten best Fuzzy Structure-Property Models 842 discovered during training, which differ from each other by some predetermined amount. Again, the difference between two models can be defined 'genotypically' or 'phenotypically', i.e. by comparing the models based either on their internal structure, or their predictions.

d. Hybrid Models

The Structure-Property Model Generator 800 can generate Model Structures 820 that combine elements of Statistics 802, Neural Networks 804, Fuzzy Logic 806, and/or Model-Specific Methods 808. Such Model Structures 820 are referred to as Hybrid Model Structures, and the corresponding models are referred to as Hybrid Models. A preferred embodiment of such a Hybrid Model Structure 820 that combines elements of Neural Networks 804 and Fuzzy Logic 806 is referred to as a NeruoFuzzy Model Structure, and shall now be described in detail.

An example of such a Hybrid Model Structure 820 is a Model Structure that combines elements of Neural Networks 804 and Fuzzy Logic 806, hereafter referred to as a Neuro-Fuzzy Model Structure or Neuro-Fuzzy Model. An example of a Neuro-Fuzzy Model Structure is discussed in greater detail below.

i. Neuro-Fuzzy Models

A Neuro-Fuzzy Model Structure is a Model Structure 820 that combines the advantages of Fuzzy Logic 806 (e.g. human-like rule-based reasoning, ease of incorporating expert knowledge) and Neural Networks 804 (e.g. learning ability, optimization ability, and connectionist structure). On the neural side, more transparency is obtained by pre-structuring a neural network to improve its performance, or by interpreting the weight matrix that results from training. On the fuzzy side, the parameters that control the performance of a fuzzy model can be tuned using techniques similar to those used in neural network systems. Thus, neural networks can improve their transparency, making them closer to fuzzy systems, while fuzzy systems can self-adapt, making them closer to neural networks.

Neuro-Fuzzy systems can be of three main types:

(1) neural fuzzy systems that use neural networks as tools in fuzzy models;

(2) fuzzy neural networks that fuzzify conventional neural networks; and (3) Neuro-Fuzzy hybrid systems that incorporate neural networks and fuzzy systems into hybrid systems.

Neuro-Fuzzy modeling is reviewed in Lin and Lee, *Neural Fuzzy Systems*, Prentice-Hall (1996), incorporated herein by reference in its entirety.

Figure 11:
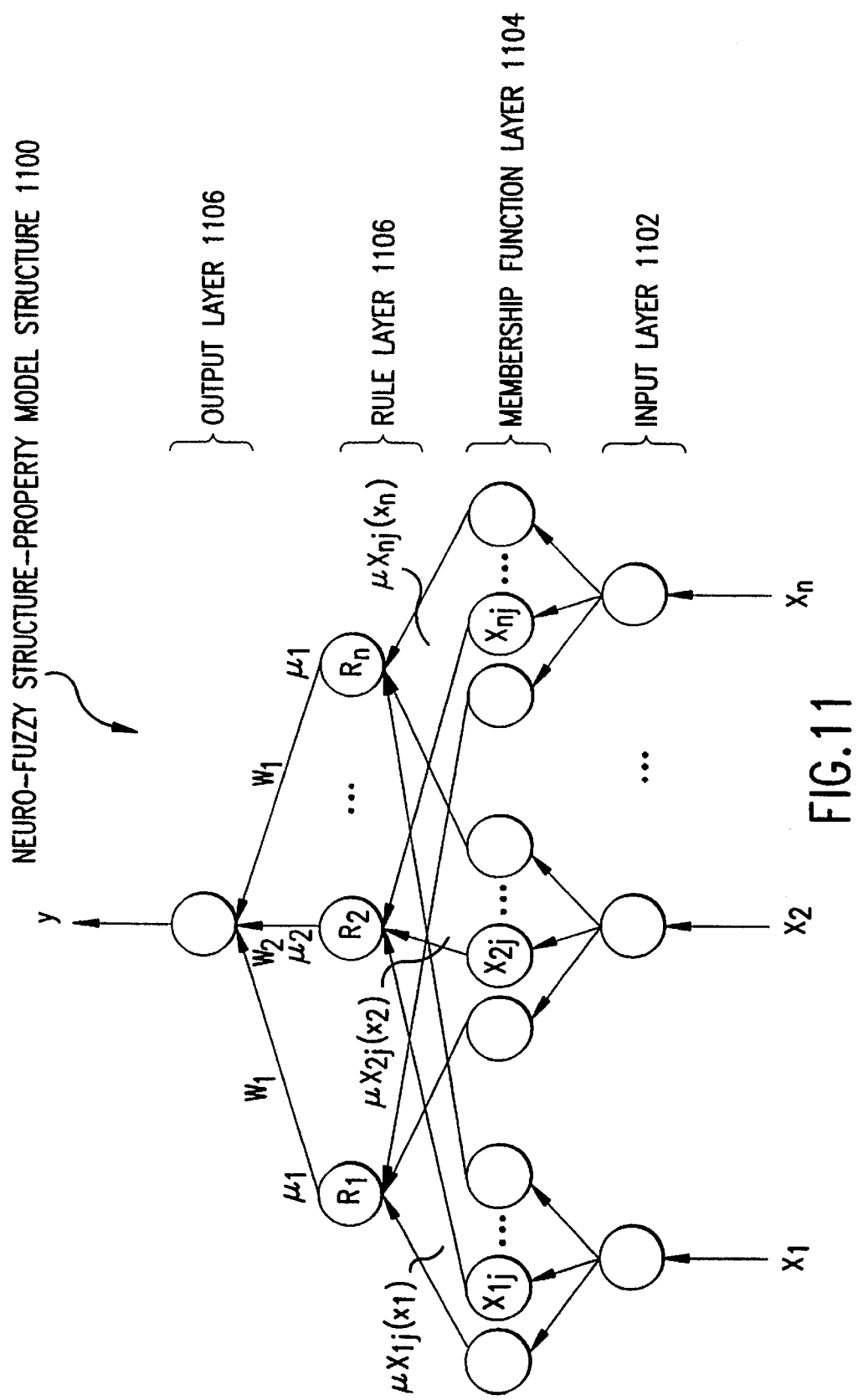
FIG. 11 is a Neuro-Fuzzy structure-property model that can be generated by the structure-property model generator illustrated in FIG. 8.

One embodiment of a Neuro-Fuzzy Structure-Property Model is a Neural Fuzzy Model with Fuzzy Singleton Rules described in Nomura et al., *Proc. IEEE Int. Conf. Fuzzy Syst.*, 1320, San Diego (1992), incorporated herein by reference in its entirety. The Structure of a Neural Fuzzy Model with Fuzzy Singleton Rules 1100 is shown in FIG. 11. Fuzzy singleton rules are of the form:

IF $x_1$ is $X_{11}$ AND $x_2$ is $X_{12}$ AND ... AND $x_n$ is $X_{1n}$ THEN $y=w_1$, where $x_1, \ldots, x_n$ are the input variables, y is the output (dependent) variable, $X_{ij}$, i=(1, ..., m), j=(1, ..., n) are fuzzy subsets of the universes of discourse of $X_1, \ldots, X_n$ with fuzzy membership functions $\mu x_{ij}(x_i)$, and $w_i$ is a real number of the consequent part. If product inference and a centroid defuzzifier are used, the output y of such a Neuro-Fuzzy Structure-Property Model 1100 is computed by EQ. 1:

$$y = \frac{\sum_{i=1}^{r} \mu_i w_i}{\sum_{i=1}^{r} \mu_i} \quad \text{EQ. 1}$$

where:

$$\mu_i = \mu_{1i}(x_1)\mu_{x_{2i}}(X_2) \ldots \mu_{x_{ni}}(x_n) \quad \text{EQ. 2}$$

Alternatively, the output y can be computed by EQ. 3:

$$y = \sum_{i=1}^{r} \mu_i W_i \quad \text{EQ. 3}$$

Referring back to FIG. 8, the Trainer 822 of the Neuro-Fuzzy Structure-Property Model Generator 800 preferably trains (i.e. constructs and/or refines) the Neuro-Fuzzy Structure-Property Model Structure 820 using Gradient Minimization 832, Monte-Carlo Sampling 834, Simulated Annealing 836, Evolutionary Programming 838, and/or a Genetic Algorithm 840, in order to minimize the overall prediction error for a prescribed set of Training Cases. The Trainer 822 can use a pre-existing Neuro-Fuzzy Structure-Property Model 842 or can construct a new one directly from the Structure-Property Data 124, 128. In the preferred embodiment described above (i.e. if the Neuro-Fuzzy Structure-Property Model Structure is a Neural Fuzzy Model with Fuzzy Singleton Rules), training is the process of constructing and/or refining the rules, membership functions $\mu x_{ij}(x_i)$, and/or the real numbers $w_i$. As in traditional fuzzy systems, the membership functions can be Gaussians, triangular functions, or trapezoidal functions. Alternatively, any other suitable functional form can be used.

An example of a training procedure for a Neural Fuzzy Model with Fuzzy Singleton Rules based on Gradient Minimization 832 is given in Nomura et al., and Lin and Lee, Supra. However, the present invention is not limited to this embodiment. Alternatively, the Trainer 822 can train the Neuro-Fuzzy Structure-Property Model Structure 820 using Gradient Minimization 832, Monte-Carlo Sampling 834, Simulated Annealing 836, Evolutionary Programming 838, and/or a Genetic Algorithm 840. Each of these methods requires a suitable encoding of the free parameters of the model, and their implementation should be straightforward to persons skilled in the art.

Again, the Trainer 822 can be configured to retain more than one Neuro-Fuzzy Structure-Property Models 842 during the training phase (flow arrow 890 in FIG. 8). For example, the Trainer 822 can be configured to retain the ten best Neuro-Fuzzy Structure-Property Models 842 discovered during the training phase. Alternatively, the Trainer 822 can be configured to retain the ten best Neuro-Fuzzy Structure-Property Models 842 discovered during training, which differ from each other by some predetermined amount. Again, the difference between two models can be defined 'genotypically' or 'phenotypically', i.e. by comparing the models based either on their internal structure, or their predictions.

e. Model-Specific Methods

The Structure-Property Model Generator 800 can generate Structure Property Models 842 based on Model-Specific Methods 808. Model-Specific Methods 808 refer to methods that are specific to the application domain of the model. Examples of such Model-Specific Methods 808 are methods that compute the energy of a particular molecular conformation or receptor-ligand complex such as an empirical force field or a quantum-mechanical method, methods that align the 3-dimensional structures of two or more chemical compounds based on their shape, electronic fields and/or other criteria, methods that predict the affinity and binding conformation of a ligand to a particular receptor binding site, methods that construct receptor models based on the 3-dimensional structures of known ligands, etc. Examples of such Model-Specific Methods 808 are described in greater detail below.

Model-Specific Methods 808 can include methods that take into account the 3-dimensional structures of the chemical compounds and/or their biological targets. Such methods are of two main types: docking methods and 3D QSAR methods. Examples of such methods that can be used shall now be described.

i. Docking Methods

Docking methods are methods that attempt to predict the binding conformation between a ligand and a receptor based on their 3-dimensional fit, and/or provide an absolute or relative measure of the affinity of a particular ligand for a particular receptor, based on the quality of their 3-dimensional fit. Docking methods require a 3-dimensional model of the receptor (or parts of the receptor), which can be determined directly through X-ray crystallography, nuclear magnetic resonance, or some other 3D structure-determination technique, or indirectly through homology modeling based on the 3-dimensional structure of a related receptor, for example.

Most docking methods reported to date are static in nature. That is, a suitable energy function is derived based on an analysis of the 3-dimensional structures of known receptor-ligand complexes, and that energy function is subsequently used to evaluate the energy of a particular receptor-ligand binding conformation. The terms 'energy' and 'energy function' are used herein to denote any numerical method for evaluating the quality of the interaction between a ligand and a receptor at a particular binding conformation. Such energy functions are usually combined with a search/optimization method such as Gradient Minimization 832, Monte-Carlo Sampling 834, Simulated Annealing 836, Evolutionary Programming 838, and/or a Genetic Algorithm 840, to identify one or more low energy binding conformations, and to predict the affinity of a particular ligand for a particular receptor.

Docking methods are reviewed in Lybrand, *Curr. Opin. Struct. Biol.* (April 1995), Shoichet et al., *Chem. Biol.* (March 1996), Lengauer et al., *Curr. Opin. Struct. Biol.* (June 1996), Willett, *Trends Biotechnol.* (1995), and Jackson, *Curr. Opin. Biotechnol.* (December 1995), incorporated herein by reference in their entirety.

A docking method can be used to derive 3-dimensional structural models of ligands bound to a particular receptor (s), and/or to obtain estimates of the binding affinity of ligands for a particular receptor(s). In a preferred embodiment, the Analysis Module 118 determines the 3-dimensional structures of selected receptor-ligand complexes from the Directed Diversity Library 108. Preferably, the 3-dimensional structures of the complexes are determined using X-ray crystallography, nuclear magnetic resonance, or some other suitable 3D structure-determination technique.

It is not necessary that every compound in the Directed Diversity Library 108 is analyzed by the Analysis Module 118 to derive a 3-dimensional receptor map. It should be understood that it is possible that none of the compounds in a given Directed Diversity Library 108 or a sequence of Directed Diversity Libraries 108 will be analyzed by the Analysis Module 118 to obtain a 3-dimensional receptor map. It is also possible that every compound in the Directed Diversity Library 108 is analyzed by the Analysis Module 118 to derive a 3-dimensional receptor map. The determination as to which compounds from the Directed Diversity Library 108 will actually be analyzed by the Analysis Module 118 to derive a 3-dimensional receptor map can be determined manually (as specified by operator input, for example) or automatically by the Directed Diversity Manager 310.

In one embodiment, the 3D Receptor Map Data 522 (FIG. 5) generated by the 3D Receptor Mapping Module 418 is used by the Trainer 822 to train (i.e. construct and/or refine) the energy function that is used by the docking method to evaluate the energy of a particular receptor-ligand binding conformation. The training of the energy function is carried out using Gradient Minimization 832, Monte-Carlo Sampling 834, Simulated Annealing 836, Evolutionary Programming 838, and/or a Genetic Algorithm 840, so that the prediction error for a prescribed Training Set of 3D Receptor Map Data 522 is minimized. The prediction error is specified based on the difference between the actual and predicted 3-dimensional structures of the receptor-ligand complexes in the Training Set (such as the RMSD criterion, for example), and/or based on the difference between the actual and predicted affinities of the receptor-ligand complexes in the Training Set. Several energy functions and several methods for training such energy functions have been reported, and their implementation should be straightforward to persons skilled in the art.

ii. 3D QSAR Methods

The Structure-Property Model Generator 800 can also be used to generate one or more 3D QSAR models. 3D QSAR models are models that are based on an analysis of the 3-dimensional structures of a series of ligands whose biological activities/properties are known. Unlike docking methods, however, 3D QSAR methods do not require knowledge of the 3-dimensional structure of the receptor or receptor-ligand complex. 3D QSAR methods are reviewed in Kubinyi (Ed.), *3D QSAR in Drug Design*, ESCOM, Leiden (1993), incorporated herein by reference in its entirety.

In one embodiment, the Structure-Property Model Generator 800 generates Structure-Property Models 842 based on one or more 3D QSAR methods. Such 3D QSAR methods include, but are not limited to, pharmacophore identification, structural alignment and molecular superposition, molecular shape analysis, mini-receptors and pseudo-receptors, distance geometry, hypothetical active site lattice, and/or molecular interaction fields. Alternatively, any other suitable 3D QSAR method can be used.

Referring back to FIG. 8, a 3D QSAR Model Structure 820 can be trained to minimize the prediction error using Gradient Minimization 832, Monte-Carlo Sampling 834, Simulated Annealing 836, Evolutionary Programming 838, and/or a Genetic Algorithm 840. Alternatively, the 3D QSAR Model Structure 820 can be trained to minimize the prediction error using a combination of Gradient Minimization 832, Monte-Carlo Sampling 834, Simulated Annealing 836, Evolutionary Programming 838, and/or Genetic Algorithms 840. The training process involves adjusting the free parameters of the 3D QSAR Structure-Property Model Structure 820 to minimize the mean prediction error (or some other suitable error criterion) for a Training Set of Structure-Property Data 124, 128 within some prescribed tolerance. The implementation of such method should be straightforward to persons skilled in the art.

As in the functional, Neural Network, Fuzzy, and Neuro-Fuzzy models described above, the Trainer 822 can be configured to retain more than one 3D QSAR Models 842 during the training phase (flow arrow 890 in FIG. 8). For example, the Trainer 822 can be configured to retain the ten best 3D QSAR Models 842 discovered during the training phase. Alternatively, the Trainer 822 can be configured to retain the ten best 3D QSAR Models 842 discovered during training, which differ from each other by some predetermined amount. Again, the difference between two models can be defined 'genotypically' or 'phenotypically', i.e. by comparing the models based either on their internal structure, or their predictions.

4. Experiment Planner 130
a. Selection Criteria 104

The Experiment planner 130 can define two general types of Selection Criteria 104. The first type of Selection Criteria 104 represents functions or algorithms that receive a compound and/or a list of compounds from the Compound Library 102, and that return a numerical value that represents an individual or collective property of these compounds. The second type of Selection Criteria 104 represents specific constraints and/or methods for generating such lists of compounds. Both types of Selection Criteria 104 are discussed below.

i. First Type of Selection Criteria 104

The first type of Selection Criteria 104 represent functions or algorithms that receive a compound and/or a list of compounds from the Compound Library 102, and return a numerical value that represents an individual or collective property of these compounds. Examples of such Selection Criteria 104 that can be used in a preferred embodiment shall now be described. However, it should be understood that the present invention is not limited to this embodiment, and that other suitable Selection Criteria 104 can also be used.

One such Selection Criterion 104 (referred to hereafter as a Compound Availability Criterion) receives as input a list of compounds from the Compound Library 102, and returns the number or fraction of these compounds that are available from the Chemical Inventory 110.

Another such Selection Criterion 104 (referred to hereafter as a Reagent Count Criterion) receives as input a list of compounds from the Compound Library 102, and returns the number of Reagents 114 that must be mixed together in the Synthesis Module 112 in order to synthesize these compounds according to a prescribed synthetic scheme.

Another such Selection Criterion 104 (referred to hereafter as a Reagent Availability Criterion) receives as input a list of compounds from the Compound Library 102, identifies which Reagents 114 must be mixed together in the Synthesis Module 112 in order to synthesize these compounds according to a prescribed synthetic scheme, and returns the number or fraction of these Reagents 114 that are available from the Reagent Inventory 116.

Another such Selection Criterion 104 (referred to hereafter as a Reagent Cost Criterion) receives as input a list of compounds from the Compound Library 102, identifies which Reagents 114 must be mixed together in the Synthesis Module 112 in order to synthesize these compounds according to a prescribed synthetic scheme, identifies which of these Reagents 114 need to be purchased from an external source, and returns the cost of purchasing these Reagents 114 from such an external source.

Another such Selection Criterion 104 (referred to hereafter as a Molecular Diversity Criterion) receives as input a list of compounds from the Compound Library 102, and returns a numerical value that represents the molecular diversity of these compounds. Molecular diversity refers to the ability of a given set of compounds to exhibit a variety of prescribed structural, physical, chemical and/or biological characteristics. The field of molecular diversity is reviewed in Martin et al., *Reviews in Computational Chemistry*, Vol 10, VCH, Weinheim (1977), and Agrafiotis, *Encyclopedia of Computational Chemistry*, Wiley (in press), incorporated herein by reference in their entirety.

Molecular diversity is a collective property, and is usually defined in a prescribed 'chemical space', i.e. in a space defined by a prescribed set of molecular properties or characteristics. Consequently, a diverse collection of compounds in one definition of chemical space may not necessarily be diverse in another definition of chemical space.

A number of methods and algorithms to extract a diverse subset of compounds from a larger collection have been reported. Such algorithms include clustering, maximin, stepwise elimination, cluster sampling, d-optimal design, etc. Most of these methods are 'greedy' methods that select compounds in an incremental manner. The system of the present invention represents molecular diversity as a Selection Criterion 104, i.e. as a function or algorithm that receives as input a list of compounds, and returns a numerical value that represents the molecular diversity of these compounds. Moreover, the Diversity Criterion can be used as part of an Objective Function that is used by the Selector 106 to select a Directed Diversity Library 108 for the next iteration.

A preferred embodiment of a Diversity Criterion is given by EQ. 4:

$$D(S) = \frac{\sum_{i}^{n} \min_{j \neq i}^{n} d_{ij}}{n(n-1)/2} \qquad \text{EQ. 4}$$

where S is a set of compounds, D(S) is the diversity of the compounds in S, n is the number of compounds in S, i, j are used to index the elements of S, and $d_{ij}$ is the distance between the i-th and j-th compounds in S. In a preferred embodiment, the distance $d_{ij}$ is a Minkowski metric (e.g. Manhattan distance, Euclidean distance, ultrametric distance, etc.) in a multivariate property space. Preferably, the property space is defined using one or more molecular features (descriptors). Such molecular features can include topological indices, physicochemical properties, electrostatic field parameters, volume and surface parameters, etc. For example, these features can include, but are not limited to, molecular volume and surface areas, dipole moments, octanol-water partition coefficients, molar refractivities, heats of formation, total energies, ionization potentials, molecular connectivity indices, substructure keys, hashed fingerprints, atom pairs and/or topological torsions, atom layers, 2D and 3D auto-correlation vectors, 3D structural and/or pharmacophoric keys, electronic fields, etc. Alternatively, the Hamming distance:

$$d_{ij} = \frac{|XOR(x_i, x_j)|}{k} \qquad \text{EQ. 5}$$

Tanimoto coefficient:

$$d_{ij} = \frac{|AND(x_i, x_j)|}{|IOR(x_i, x_j)|} \quad \text{EQ. 6}$$

or Dice coefficient:

$$d_{ij} = \frac{2|AND(x_i, x_j)|}{|x_i| + |x_j|} \quad \text{EQ. 7}$$

can be used. In EQ. 5–7, $x_i$ and $x_j$ represent binary strings encoding the i-th and j-th structures, respectively (e.g. a substructure key, pharmacophore key, or hashed fingerprint), k is the length of the binary sets $x_i$ and $x_j$, $AND(x_i, x_j)$, $IOR(x_i, x_j)$ and $XOR(x_i, x_j)$ are the binary intersection, union ('inclusive or') and 'exclusive or' of $x_i$ and $x_j$, respectively, and $|x_i|$ is the number of bits that are 'on' in $x_i$. However, the present invention is not limited to these embodiments, and any suitable distance measure and/or definition of chemical space can alternatively be used.

EQ. 4 exhibits quadratic time complexity, i.e. the time required to compute D(S) scales to the square of the number of compounds in the set S. To remedy this problem, in a preferred embodiment, the method can be combined with a nearest neighbor algorithm such as a k-d tree (Bentley, *Comm. ACM*, 18(9): 509 (1975), Friedman et al., *ACM Trans. Math. Soft.*, 3(3): 209 (1977)), incorporated herein by reference in its entirety. Alternatively, any other suitable algorithm can be used, including, but not limited to:

(1) ball trees (Omohundro, *International Computer Science Institute Report TR*-89-063, Berkeley, Calif. (1989)), incorporated herein by reference in its entirety;

(2) bump trees (Omohundro, *Advances in Neural Information Processing Systems* 3, Morgan Kaufmann, San Mateo, Calif. (1991)), incorporated herein by reference in its entirety; and (3) gridding, and Voronoi tesselation (Sedgewick, *Algorithms in C*, Addison-Wesley, Princeton (1990), incorporated herein by reference in its entirety.

Another such Selection Criterion 104 (referred to hereafter as a Molecular Similarity Criterion) receives as input a list of compounds from the Compound Library 102 and a list of reference compounds, and returns a numerical value that represents the molecular similarity of these compounds to the reference compounds. In a preferred embodiment, the similarity of a list of compounds to a prescribed set of reference compounds is computed using EQ. 8:

$$M(S, L) = \frac{\sum_{i=1}^{n} \min_{j=i}^{k} d_{ij}}{n} \quad \text{EQ. 8}$$

where S is a set of compounds, L is a set of reference compounds, M(S, L) is the measure of similarity of the compounds in S to the compounds in L, n is the number of compounds in S, k is the number of compounds in L, i and j are used to index the elements of S and L, respectively, and $d_{ij}$ is the distance between the i-th compound in S and the j-th compound in L. Thus, EQ. 8 represents the mean distance of a compound in S from its nearest reference compound in L. In a preferred embodiment, the distance $d_{ij}$ is a Minkowski metric (e.g. Manhattan distance, Euclidean distance, ultrametric distance, etc.) in a multivariate property space. Preferably, the property space is defined using one or more molecular features (descriptors). Such molecular features can include topological indices, physicochemical properties, electrostatic field parameters, volume and surface parameters, etc. For example, these features can include, but are not limited to, molecular volume and surface areas, dipole moments, octanol-water partition coefficients, molar refractivities, heats of formation, total energies, ionization potentials, molecular connectivity indices, substructure keys, hashed fingerprints, atom pairs and/or topological torsions, atom layers, 2D and 3D auto-correlation vectors, 3D structural and/or pharmacophoric keys, electronic fields, etc. Alternatively, the distance $d_{ij}$ can be computed by the Hamming (EQ. 5), Tanimoto (EQ. 6), or Dice coefficients (EQ. 7) using a binary molecular representation, such as a substructure key, pharmacophore key, or hashed fingerprint, for example. However, the present invention is not limited to these embodiments, and any suitable definition of chemical space, distance measure, and/or Similarity Criterion can alternatively be used.

The set of reference compounds may or may not represent real or synthesizable compounds. For example, the set of reference compounds can represent an 'ideal' or 'target' set of properties that the selected compounds should possess. In this case, the Similarity Criterion in EQ. 8 (or any other suitable Similarity Criterion) measures how well a particular set of compounds matches a prescribed set of target properties.

The Similarity Criterion can be used to design a set of compounds close to a reference set of compounds, or to design a set of compounds far from a reference set of compounds. For example, if EQ. 8 is used, this can be achieved by simply reversing the sign of D(S, L).

Another Selection Criterion 104 (referred to hereafter as a Synthetic Confidence Criterion) receives as input a compound (or list of compounds) from the Compound Library 102, and returns a confidence factor that this compound can be synthesized by the Synthesis Module 112 using a prescribed synthetic scheme. For example, this confidence factor can be computed by an expert system for computer-assisted organic synthesis. However, it should be understood that the present invention is not limited to this embodiment.

Another such Selection Criterion 104 (referred to hereafter as a Synthetic Yield Criterion) receives as input a compound (or list of compounds) from the Compound Library 102, and returns a predicted yield for the compound (s), if the compound(s) were to be synthesized by the Synthesis Module 112 according to a prescribed synthetic scheme. For example, the synthetic yield can be computed by an expert system for computer-assisted organic synthesis. However, it should be understood that the present invention is not limited to this embodiment.

Another such Selection Criterion 104 (referred to hereafter as a Synthetic Ease or Synthetic Planning Criterion) receives as input a list of compounds from the Compound Library 102, and returns a numerical value that represents the ease of planning and executing the synthesis of these in the Synthesis Module 112 according to a prescribed synthetic scheme. For example, one such Synthetic Planning Criterion can be a value indicating if (and by how much) a particular collection of compounds exceeds the synthetic capacity of an automated robotic Synthesis Module 112. Another example of such a Synthetic Planning Criterion may be the number of different synthetic schemes that must be executed by the Synthesis Module 112 in order to synthesize a particular collection of compounds. However, it should be understood that the present invention is not limited to these embodiments.

Another such Selection Criterion 104 (referred to hereafter as a Structure-Property Model Confirmatory Criterion) receives as input a list of compounds from the Compound Library 102 and a Structure-Property Model 842, and returns the mean predicted property (or activity) of these compounds, as inferred by the specified model. Alternatively, any other suitable numerical value that can be derived from the predicted properties of the specified compounds as inferred by the specified Structure-Property Model can be used. For example, the Structure-Property Model Confirmatory Criterion can return the minimum property, maximum property, or deviation of properties of the specified list of compounds, as inferred by the specified Structure-Property Model. However, it should be understood that the present invention is not limited to these embodiments. Any form of a Structure-Property Model 842 can be used in this regard. For example, the Structure-Property Models 842 can include models derived from Statistics 802, Neural Networks 804, Fuzzy Logic 806, and/or Model-Specific Methods 808, and/or models derived from a combination of Statistics 802, Neural Networks 804, Fuzzy Logic 806, and/or Model-Specific Methods 808, such as the Neuro-Fuzzy Structure Property Model 1100 described above, for example. These Structure-Property Models 842 can also include models derived from docking methods and/or 3D QSAR methods including, but not limited to, pharmacophore identification, structural alignment and molecular superposition, molecular shape analysis, mini-receptors and pseudo-receptors, distance geometry, hypothetical active site lattice, and/or molecular interaction fields. However, it should be understood that the present invention is not limited to these embodiments.

Another such Selection Criterion 104 (referred to hereafter as a Structure-Property Model Discriminatory Criterion) receives as input a compound (or list of compounds) from the Compound Library 102 and two or more Structure-Property Models 842, and returns a numerical value that represents the ability (or collective ability) of this compound (or list of compounds) to discriminate between the specified models. The term 'discriminate' is used herein to denote the ability of a compound (or list of compounds) to distinguish between two or more models. A compound is said to possess high discriminatory ability if the models differ substantially in their predictions of the properties of that compound. Structure-Property Model Discriminatory Criteria 104 can be used if the Structure-Property Models 842 are weak or under-determined, for example. In such cases, it is often difficult to select which Structure-Property Model(s) 842 should be used to select the Directed Diversity Library 108 for the next iteration. Thus, it may be desirable to select compounds that can discriminate between two or more Structure-Property Models 842, so that the Structure-Property Models 842 that reflect true correlations are reinforced, while the Structure-Property Models 842 that do not reflect true correlations are eliminated. An example of a Structure-Property Model Discriminatory Criterion is the difference between the minimum and maximum property predictions for a given compound as inferred by the specified Structure-Property Models 842, or the deviation of the property predictions for a given compound as inferred by the specified Structure-Property Models 842. However, it should be understood that the present invention is not limited to these embodiments. As with Structure-Property Model Confirmatory Criteria 104, any form of a Structure-Property Model 842 can be used in this regard. For example, the Structure-Property Models 842 can include models derived from Statistics 802, Neural Networks 804, Fuzzy Logic 806, and/or Model-Specific Methods 808, and/or models derived from a combination of Statistics 802, Neural Networks 804, Fuzzy Logic 806, and/or Model-Specific Methods 808, such as the Neuro-Fuzzy Structure Property Model 1100 described above, for example. These Structure-Property Models 842 can also include models derived from docking methods and/or 3D QSAR methods including, but not limited to, pharmacophore identification, structural alignment and molecular superposition, molecular shape analysis, mini-receptors and pseudo-receptors, distance geometry, hypothetical active site lattice, and/or molecular interaction fields. However, it should be understood that the present invention is not limited to these embodiments.

Structure-Property Model Discriminatory Criteria can also be used to determine if a particular compound or list of compounds exhibits selective properties. For example, Structure-Property Model Discriminatory Criteria 104 can be used to determine whether a particular compound can bind selectively to a specific target (also referred to herein as a Selectivity Criterion). For example, a Selectivity Criterion 104 can be implemented using EQ. 9:

$$s_i = \frac{p_i}{\sum_i p_i} \qquad \text{EQ. 9}$$

where $s_i$ denotes the selectivity of a particular compound for the i-th property (EQ. 9 assumes that the properties $p_i$ are normalized). For example, EQ. 9 can be used to describe whether a particular compound binds selectively to the enzyme Thrombin versus the enzymes Trypsin and Urokinase, by substituting $p_i$ with the binding affinities of that compound for Thrombin, Trypsin and Urokinase as predicted by a Thrombin, Trypsin and Urokinase Structure-Property Model 842, respectively. If more than one Structure Property Models 842 are available for a particular property (or properties), EQ. 9 can be replaced by EQ. 10:

$$s_i = \frac{\text{mean}(p_{ij})}{\sum_i \text{mean}(p_{ij})} \qquad \text{EQ. 10}$$

where $p_{ij}$ is the i-th property of the compound as predicted by the j-th Structure-Property Model 842, and mean(.) is a function that returns the mean of its arguments.

Another such Selection Criterion 104 (referred to hereafter as a Patentability Criterion) receives as input a compound (or list of compounds) from the Compound Library 102, and returns a value indicating whether this compound is protected by an issued US or foreign patent. Preferably, the Experiment Planner 130 searches a patent database to determine is the specified compound (or list of compounds) has been patented or has not been patented.

Another such Selection Criterion 104 (referred to hereafter as a Bioavailability Criterion) receives as input a compound (or list of compounds) from the Compound Library 102, and returns a value that represents the predicted bioavailability of that compound, as inferred by a suitable Bioavailability Structure-Property Model.

Another such Selection Criterion 104 (referred to hereafter as a Toxicity Criterion) receives as input a compound (or list of compounds) from the Compound Library 102, and returns a value that represents the predicted toxicity of that compound, as inferred by a suitable Toxicity Structure-Property Model.

Alternatively, the Experiment Planner 130 can define other Selection Criteria 104 that can be derived from information pertaining to a given compound or list of compounds, and that can be used to guide the selection of the Directed Diversity Library 108 for the next iteration.

ii. Second Type of Selection Criteria 104

The second type of Selection Criteria 104 represent specific constraints and/or methods for generating such lists of compounds. A few examples of such Selection Criteria 104 shall now be described.

One such Selection Criterion 104 defines a list of compounds that should not be included in the Directed Diversity Library 108 for the next iteration (referred to herein as the Excluded Compounds Criterion). For example, these compounds (referred to herein as the Excluded Compounds) can be compounds whose properties of interest are already known (e.g. compounds previously analyzed by the Analysis Module 118). Alternatively, the Excluded Compounds can be compounds whose predicted bioavailability as predicted by a Bioavailability Structure-Property Model can be below a prescribed threshold, compounds whose predicted toxicity as predicted by a Toxicity Structure-Property Model can be above a prescribed threshold, compounds that require expensive Reagents 114 to be mixed together in order to be generated by the Synthesis Module 112 (e.g. Reagents 114 whose const exceeds a prescribed value), compounds that cannot be made in an automated or partially automated fashion by the Synthesis Module 112, etc.

The Excluded Compounds can also represent combinations of compounds that cannot all be part of a Directed Diversity Library 108 for the next iteration. For example, the Excluded Compounds can be a set of compounds that require more than one synthetic scheme to be executed by the Synthesis Module 112 in order to be synthesized. For example, if the Compound Library 102 is comprised of two or more combinatorial chemical libraries, each of which requires a different synthetic scheme to be executed by the Synthesis Module 112 in order for the compounds in these libraries to be synthesized, the Excluded Compounds Criterion can be used to exclude combinations of compounds that cannot all be made using a single synthetic scheme, or to limit the selection of compounds for the next Directed Diversity Library 108 to a specific combinatorial library (or libraries). Alternatively, the Excluded Compounds can represent combinations of compounds that require more than a prescribed number of Reagents 114 to be mixed together by the Synthesis Module 112 in order for these compounds to be synthesized. However, the present invention is not limited to these embodiments.

Another such Selection Criterion 104 defines the number and/or subset of Reagents 114 that can be mixed together by the Synthesis Module 112. Such a Selection Criterion limits the selection of the Directed Diversity Library 108 for the next iteration to a specific number and/or subset of building blocks.

Another such Selection Criterion 104 defines the way in which the Reagents 114 are to be mixed together by the Synthesis Module 112. For example, such a Selection Criterion 104 can specify that twenty Reagents 114 must be divided into two sets of ten, and these two sets of ten Reagents 114 must be mixed together in a combinatorial fashion to generate all one hundred combinations of a combinatorial library with two variable sites (referred to as an Array Design hereafter). However, the present invention is not limited to this embodiment.

b. Objective Functions 105

The Experiment planner 130 uses one or more Selection Criteria 104 to define one or more Objective Functions 105.

The Objective Function 105 represents a function and/or algorithm that receives a list of compounds from the Compound Library 102 and a list of Selection Criteria 104, and returns a numerical value that represents a collective property of the specified compounds.

Any functional form can be used to implement the Objective Function 105 and to combine the specified Selection Criteria 104. For example, a suitable Objective Function 105 is a linear combination of a prescribed set of Selection Criteria 104, as given by EQ. 11:

$$f(S) = \sum_{i=1}^{n} w_i c_i(S) \qquad \text{EQ. 11}$$

where S is a set of compounds, $c_i(S)$ is the value of the i-th Selection Criterion 104 for the set S, $w_i$ is a weighting factor, and f(S) is the value of the Objective Function 105 for the set of compounds S. Alternatively, any other suitable functional form can be used.

An Objective Function 105 might combine, for example, a Molecular Diversity Criterion with a Molecular Similarity Criterion using EQ. 11. In this case, the weights $w_i$ determine the relative influence of the Molecular Diversity Criterion and the Molecular Similarity Criterion. For example, when the Molecular Diversity Criterion and Molecular Similarity Criterion are defined on a similar scale, EQ. 11 can be used to compute a numerical value that reflects the collective ability of a given set of compounds S to satisfy both the Molecular Diversity Criterion and Molecular Similarity Criterion under the specified weights $w_i$. Such Objective Functions 105 that combine multiple Selection Criteria 104 are referred to hereafter as Multi-Objective Functions or Multi-Criteria Functions. Alternatively, an Objective Function 105 can include a single Selection Criterion 104. For example, an Objective Function 105 can simply return the molecular diversity of a collection of compounds, as computed by a Molecular Diversity Criterion. Examples of the use of such Objective Functions 105 and Multi-Objective Functions (not shown) to select a Directed Diversity Library 108 for the next iteration are described below.

5. The Selector 106

The Selector 106 selects a Directed Diversity Library 108 for analysis, according to the Selection Criteria 104 and any Objective Functions 105. Preferably, the Directed Diversity Library 108 is comprised of compounds that are optimal or nearly optimal with respect to the specified Selection Criteria 104 and Objective Functions 105. Moreover, the Directed Diversity Library 108 should be comprised of compounds that satisfy any constraints specified by some of these Selection Criteria 104.

The task of identifying an optimal or nearly optimal set of compounds for the next Directed Diversity Library 108, given the Selection Criteria 104 and Objective Functions 105, involves a search of all subsets of compounds from the Compound Library 102 that satisfy the constraints defined by the Experiment Planner 130. As used herein, the term 'constraint' denotes a Selection Criterion 104 that excludes certain compounds or certain combinations of compounds from being selected as part of the Directed Diversity Library 108 for the next iteration. Contrast constraints to other Selection Criteria 104, which specify desired properties that the selected compounds should possess, either individually or collectively. The Directed Diversity Library 108 for the next iteration should satisfy any specified constraints and should maximize the desired properties, to the extent possible.

The task of identifying an optimal or nearly optimal set of compounds for the next Directed Diversity Library 108 can be an enormous combinatorial problem. For example, when one Selection Criterion 104 limits the selection to an n-membered Compound Library 102, and another Selection Criterion 104 specifies that the size of the Directed Diversity Library 108 for the next iteration should be comprised of k compounds from the aforementioned n-membered library, the number of different k-membered subsets of the n-membered library is given by the binomial:

$$N = \frac{n!}{k!(n-k)!} \qquad \text{EQ. 12}$$

This task is combinatorially explosive because, in all but the simplest cases, N is far too large to allow for the construction and evaluation of every possible subset given current data processing technology. As a result, a variety of stochastic modeling techniques can be employed, that are capable of providing good approximate solutions to combinatorial problems in realistic time frames. However, the present invention envisions and includes the construction and evaluation of every individual k-membered subset once computer technology advances to an appropriate point.

The Selector 106 receives the Selection Criteria 104 and Objective Functions 105 and returns the Directed Diversity Library 108. The Selector 106 preferably uses a stochastic (or exhaustive, if possible) search/optimization technique.

Figure 12:
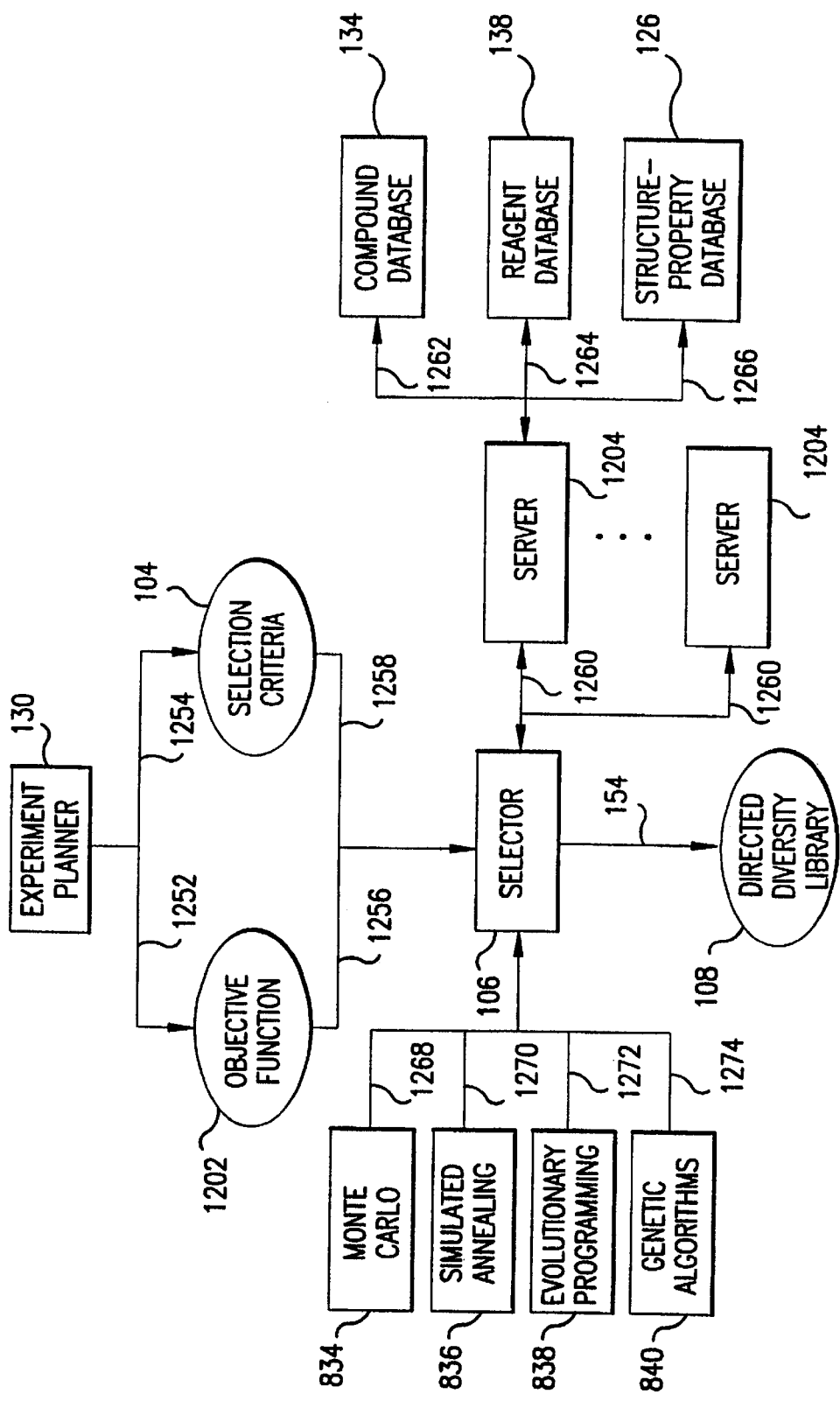
FIG. 12 is a flow diagram depicting the flow of data among an experiment planner and a selector in a lead generation system.
Figure 13:
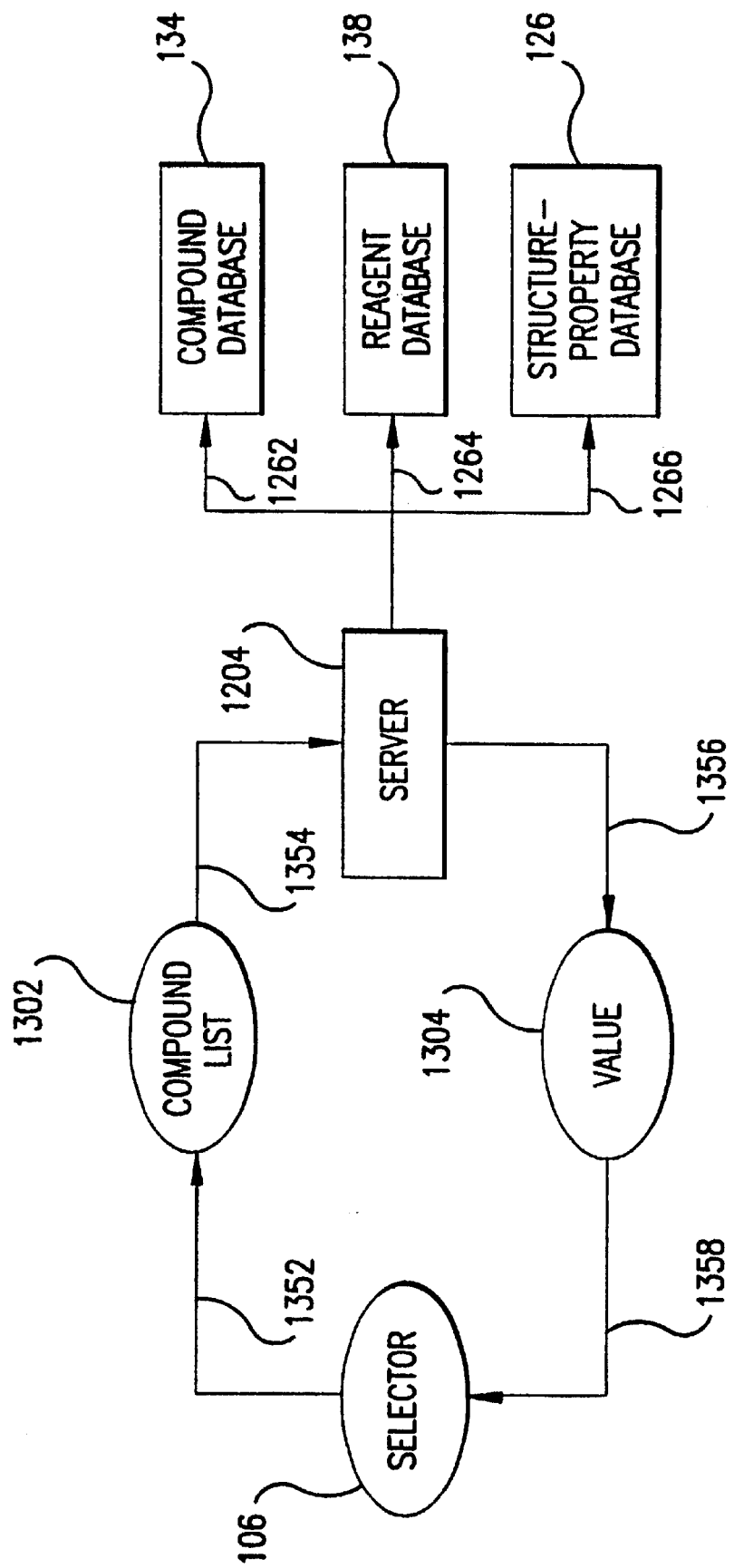
FIG. 13 is a flow diagram depicting the flow of data during selection of a directed diversity library.

Referring to FIGS. 12 and 13, in one embodiment, the Selector 106 is coupled to the Compound Database 134, the Reagent Database 138 and the Structure-Property Database 126 via dedicated Servers 1204. The Selector 106 can send a proposed Compound List 1302 the Servers 1204. The Servers 1204 can retrieve property values for the Compound List 1302 and return them to the Selector 106 as Values 1304.

Preferably, the Selector 106 generates an initial list of proposed compounds based on Selection Criteria 104 and then refines the list through an iterative process. For example, the Selector 106 can employ Monte-Carlo Sampling 834, Simulated Annealing 836, Evolutionary Programming 838, and/or a Genetic Algorithm 840, to produce a list of compounds that best satisfy all the Selection Criteria 104 in the manner specified by the Objective Function 105. The list can be refined to become the Directed Diversity Library 108 for the next iteration.

For example, referring to FIG. 13, each Server 1204 can receive a Compound List 1302 from the Selector 106. The Servers 1204 can access one or more of the databases 126, 134 and 138 to retrieve property values associated with the compounds in the Compound List 1302, and use these property values to compute the values of the respective Selection Criteria 104. The Servers 1204 can return their respective computed values as Selection Criteria Values 1304 for Compound List 1302.

Preferably, the Server 1204 can be configured by user input. For example, a user might want to select a particular method for computing molecular diversity. Similarly, a user might want to select one or more particular Structure-Property Models 192 for predicting the properties of compounds.

In one embodiment, the Selector 106 selects the Directed Diversity Library 108 for the next iteration using a Monte-Carlo Sampling 834 or Simulated Annealing 836 algorithm. Operation of this embodiment is described below with reference to FIG. 18.

6. Structure of the Present Invention

A lead generation/optimization system 100 can be implemented as a fully automated system or as a partially automated system that relies, in part, on human interaction. For example, human interaction can be employed to perform or assist in the functions described herein with respect to the Synthesis Module 112 and/or by the Analysis Module 118 and/or the Directed Diversity Manager 310.

The automated portion of the lead generation/optimization system 100 can be implemented as hardware, firmware, software or any combination thereof, and can be implemented in one or more computer systems and/or other processing systems. In one embodiment, the automated portion of the invention is directed toward one or more computer systems capable of carrying out the functionality described herein.

Figure 19:
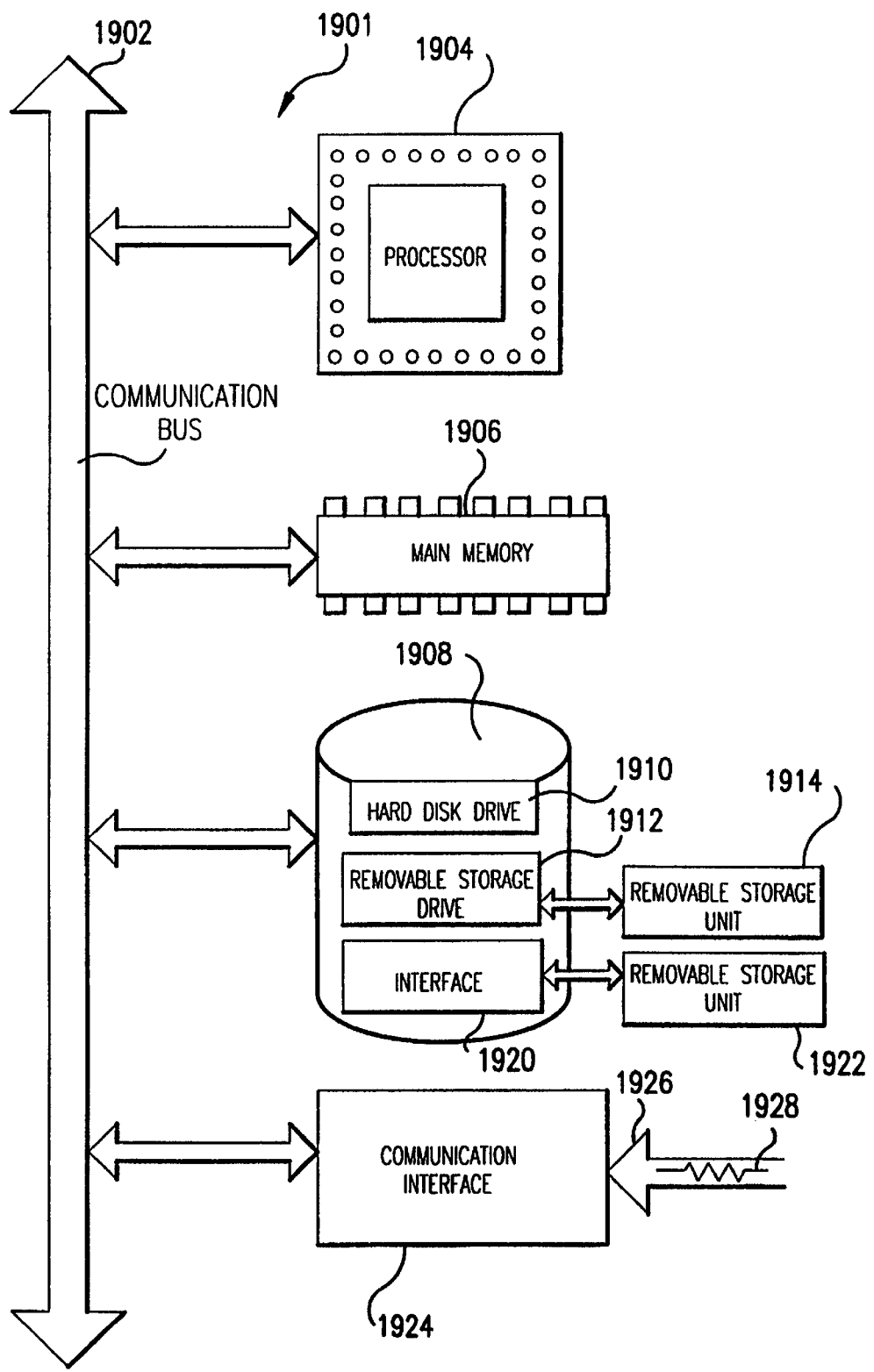
FIG. 19 is a block diagram of a computer system that can be used to implement one or more portions of the lead generation system illustrated in FIG. 3.

Referring to FIG. 19, an example computer system 1901 includes one or more processors, such as processor 1904. Processor 1904 is connected to a communication bus 1902. Various software embodiments are described in terms of this example computer system 1901. After reading this description, it will become apparent to a person skilled in the relevant art how to implement the invention using other computer systems and/or computer architectures.

Computer system 1902 also includes a main memory 1906, preferably random access memory (RAM), and can also include a secondary memory 1908. Secondary memory 1908 can include, for example, a hard disk drive 1910 and/or a removable storage drive 1912, representing a floppy disk drive, a magnetic tape drive, an optical disk drive, etc. Removable storage drive 1912 reads from and/or writes to a removable storage unit 1914 in a well known manner. Removable storage unit 1914, represents a floppy disk, magnetic tape, optical disk, etc. which is read by and written to by removable storage drive 1912. Removable storage unit 1914 includes a computer usable storage medium having stored therein computer software and/or data.

In alternative embodiments, secondary memory 1908 can include other similar means for allowing computer programs or other instructions to be loaded into computer system 1901. Such means can include, for example, a removable storage unit 1922 and an interface 1920. Examples of such can include a program cartridge and cartridge interface (such as that found in video game devices), a removable memory chip (such as an EPROM, or PROM) and associated socket, and other removable storage units 1922 and interfaces 1920 which allow software and data to be transferred from the removable storage unit 1922 to computer system 1901.

Computer system 1901 can also include a communications interface 1924. Communications interface 1924 allows software and data to be transferred between computer system 1901 and external devices. Examples of communications interface 1924 include, but are not limited to a modem, a network interface (such as an Ethernet card), a communications port, a PCMCIA slot and card, etc. Software and data transferred via communications interface 1924 are in the form of signals which can be electronic, electromagnetic, optical or other signals capable of being received by communications interface 1924. These signals 1926 are provided to communications interface via a channel 1928. This channel 1928 carries signals 1926 and can be implemented using wire or cable, fiber optics, a phone line, a cellular phone link, an RF link and other communications channels.

In this document, the terms "computer program medium" and "computer usable medium" are used to generally refer to media such as removable storage device 1912, a hard disk installed in hard disk drive 1910, and signals 1926. These computer program products are means for providing software to computer system 1901.

Computer programs (also called computer control logic) are stored in main memory and/or secondary memory 1908. Computer programs can also be received via communications interface 1924. Such computer programs, when executed, enable the computer system 1901 to perform the features of the present invention as discussed herein. In particular, the computer programs, when executed, enable the processor 1904 to perform the features of the present invention. Accordingly, such computer programs represent controllers of the computer system 1901.

In an embodiment where the invention is implemented using software, the software can be stored in a computer program product and loaded into computer system 1901 using removable storage drive 1912, hard drive 1910 or communications interface 1924. The control logic (software), when executed by the processor 1904, causes the processor 1904 to perform the functions of the invention as described herein.

In another embodiment, the automated portion of the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

Figure 3:
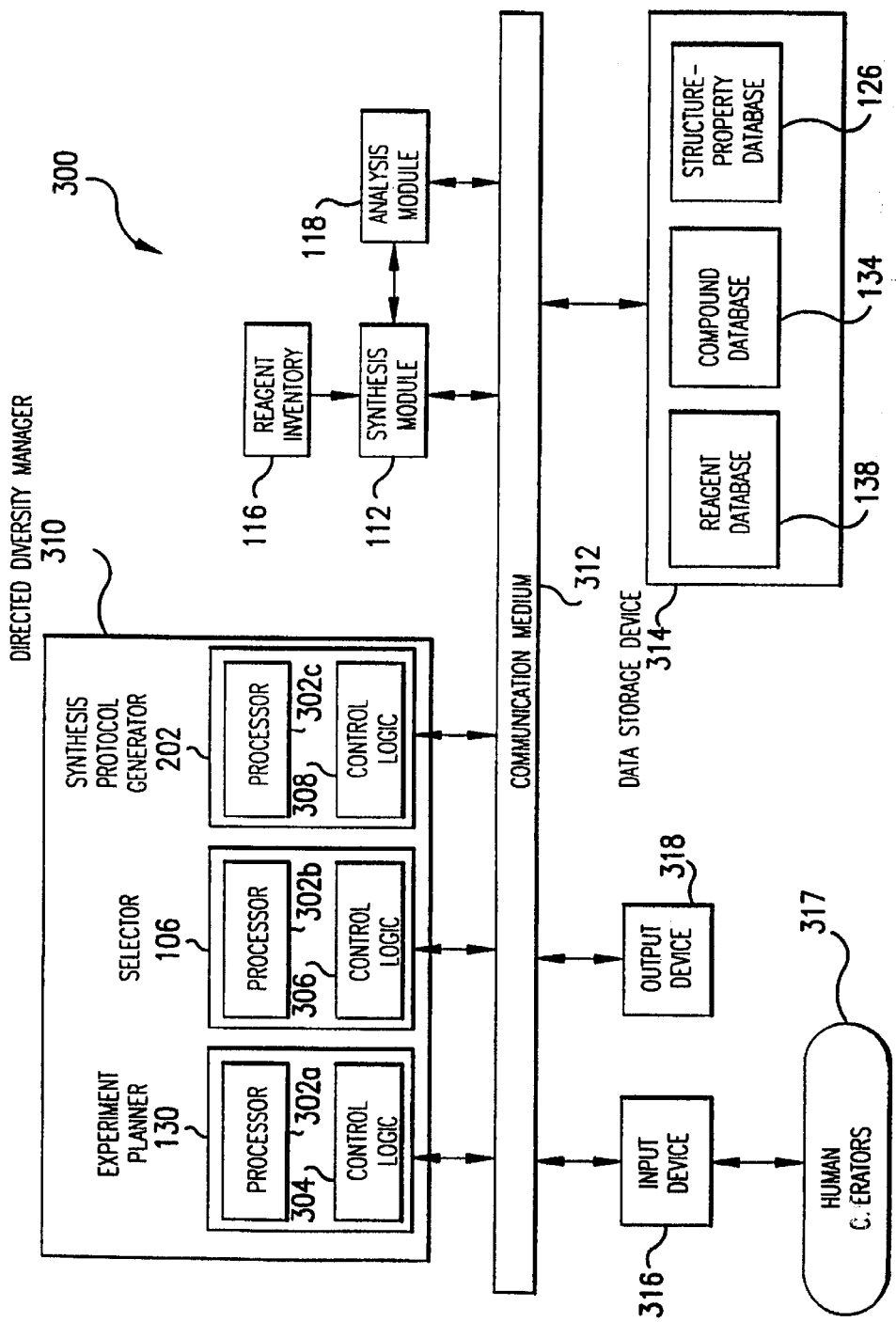
FIG. 3 is a block diagram of the lead generation system, in accordance with the present invention.

Referring to FIG. 3, a lead generation/optimization system 300 includes one or more central processing units (CPUs) 302a, 302b and 302c, which can be one or more of processors 1904. CPUs 302 operate according to control logic 304, 306, and 308, which can be software, firmware, hardware or any combination thereof.

Processors 302a, 302b and 302c can represent a single processor 302 or can represent multiple processors. Control logic 304, 306, and 308 can be executed on a single processor or on multiple processors 302.

Control logic 304, 306, and 308 preferably represent one or more computer programs such that the processor 302 operates according to software instructions contained in the control logic 304, 306, and 308. Alternatively, the processor 302 and/or the control logic 304, 306, and 308 are implemented as a hardware state machine.

Processor 302a and control logic 304 collectively represent the Experiment Planner 130. Processor 302b and control logic 306 collectively represent the Selector 106. Processor 302 and control logic 308 collectively represent the Synthesis Protocol Generator 202. The Experiment Planner 130, the Selector 106, and the Synthesis Protocol Generator 202 collectively represent a Directed Diversity Manager 310.

Directed Diversity Manager 310 can be implemented as part of a variety of computer systems. For example, Directed Diversity Manager 310 can be implemented on an Indigo, Indy, Onyx, Challenge, Power Challenge, Octane or Origin 2000 computer made by Silicon Graphics, Inc., of Mountain View, Calif. Another suitable form for the processor 302 is a DEC Alpha Workstation computer made by Digital Equipment Corporation of Maynard, Mass. Another suitable form for the Processor 302 is one of the Pentium family of processors from Intel, such as the Pentium Pro or Pentium II. Any other suitable computer system could alternatively be used.

A Communication Medium 312, comprising one or more data buses and/or IO (input/output) interface devices, connect the Experiment Planner 130, the Selector 106, and the Synthesis Protocol Generator 202 to a number of peripheral devices, such as one or more Input Devices 316, one or more Output Devices 318, one or more Synthesis Modules 112, one or more Analysis Modules 118, and one or more Data Storage Devices 314.

The Input Device(s) 316 receive input (such as data, commands, etc.) from human operators and forward such input to the Experiment Planner 130, the Selector 106, and/or the Synthesis Protocol Generator 202 via the Communication Medium 312. Any well known, suitable input device can be used in the present invention to receive input, commands, selections, etc., from operators 317, such as a keyboard, pointing device (mouse, roller ball, track ball, light pen, etc.), touch screen, voice recognition, etc. User input can also be stored and then retrieved, as appropriate, from data/command files.

The Output Device(s) 318 output information to human operators 317. The Experiment Planner 130, the Selector 106, and/or the Synthesis Protocol Generator 202 transfer such information to the Output Device(s) 318 via the Communication Medium 312. Any well known, suitable output device can be used in the present invention, such as a monitor, a printer, a floppy disk drive, a text-to-speech synthesizer, etc.

Preferably, the Synthesis Module 112 receives Robotic Synthesis Instructions 204 (FIG. 2) from the Synthesis Protocol Generator 202 via the Communication Medium 312. The Synthesis Module 112 operates according to the Robotic Synthesis Instructions 204 to selectively combine a particular set of Reagents 114 from the Reagent Inventory 116 to thereby generate the compounds from the Directed Diversity Library 108 specified by the Selector 106, that are not retrieved from the Chemical Inventory 110.

Where Directed Diversity Manager 310 is implemented as part of a computer system, Communication Medium 312, Input Device(s) 316 and Output Device(s) 318 can be an integral part of the computer system.

The Synthesis Module 112 is preferably a robot capable of mix-and-split, solid phase chemistry for coupling chemical building blocks. As used herein, the term "robot" refers to any automated or partially automated device that automatically or semi-automatically performs functions specified by instructions such as the Robotic Synthesis Instructions 204 (FIG. 2) generated by the Synthesis Protocol Generator 202.

The Synthesis Module 112 preferably performs selective micro-scale solid state synthesis of a specific combinatorial library of Directed Diversity Library 108 compounds, but is not limited to this embodiment. The Synthesis Module 112 preferably cleaves and separates the compounds of the Directed Diversity Library 108 from support resin and distributes the compounds into preferably 96 wells with from 1 to 20 Directed Diversity Library 108 compounds per well, corresponding to an output of 96 to 1920 compounds per synthetic cycle iteration, but is not limited to this embodiment. This function can alternatively be performed by a well known liquid transfer robot (not shown). Synthesis Module(s) suitable for use with the present invention are well known and are commercially available from a number of manufacturers, such as the following:

TABLE 1

| Manufacturer | City | State | Model |
| --- | --- | --- | --- |
| Advanced ChemTech | Louisville | KY | 357 MPS |
| | | | 390 MPS |
| Rainin | Woburn | MA | Symphony |
| Perkin-Elmer Corporation Applied Biosystems Division | Foster City | CA | 433A |
| Millipore | Bedford | MA | 9050 Plus |

All of the instruments listed in Table 1 perform solid support-based peptide synthesis only. The Applied Biosystems and the Millipore instruments are single peptide synthesizers. The Rainin Symphony is a multiple peptide synthesizer capable of producing up to twenty peptides simultaneously. The Advanced ChemTech instruments are also multiple peptide synthesizers, but the 357 MPS has a feature utilizing an automated mix-and-split technology. The peptide synthesis technology is preferred in producing the Directed Diversity Libraries 108 associated with the present invention. See, for example, Gallop, M. A. et al., *J. Med. Chem.* 37, 1233–1250 (1994), incorporated herein by reference in its entirety.

Peptide synthesis is by no means the only approach envisioned and intended for use with the present invention. Other chemistries for generating the Directed Diversity Libraries 108 can also be used. For example, the following are suitable-peptoids (PCT Publication No. WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., *Proc. Natl. Acad. Sci. USA* 90: 6909–6913 (1993)), vinylogous polypeptides (Hagihara et al., *J. Amer. Chem. Soc.* 114: 6568 (1992)), nonpeptidal peptidomimetics with a Beta-D-Glucose scaffolding (Hirschmann, R. et al., *J. Amer. Chem. Soc.* 114: 9217–9218 (1992)), analogous organic syntheses of small compound libraries (Chen, C. et al., *J. Amer. Chem. Soc.* 116: 2661(1994)), oligocarbamates (Cho, C. Y. et al., *Science* 261: 1303 (1993)), and/or peptidyl phosphonates (Campbell, D. A. et al., *J. Org. Chem.* 59: 658 (1994)). See, generally, Gordon, E. M. et al., *J. Med. Chem.* 37: 1385 (1994). The contents of all of the aforementioned publications are incorporated herein by reference.

Alternatively, the Synthesis Module 112 can be a robot capable of solution-phase synthesis, or a workstation that enables manual synthesis of the compounds in the Directed Diversity Library 108. A number of well-known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) that mimic the manual synthetic operations performed by a chemist. Any of the above devices are suitable for use with the present invention. The nature and implementation of modifications to these devices (if any) so that they can operate as discussed herein will be apparent to persons skilled in the relevant art.

It is noted that the functions performed by the Synthesis Module 112 can be alternatively performed by human operators, aided or not aided by robots and/or computers.

The Analysis Module(s) 118 receives the chemical compounds synthesized by the Synthesis Module(s) 112 or retrieved from the Chemical Inventory 110. The Analysis Module(s) 118 analyzes these compounds to obtain Structure-Property Data 124 pertaining to the compounds.

Figure 4:
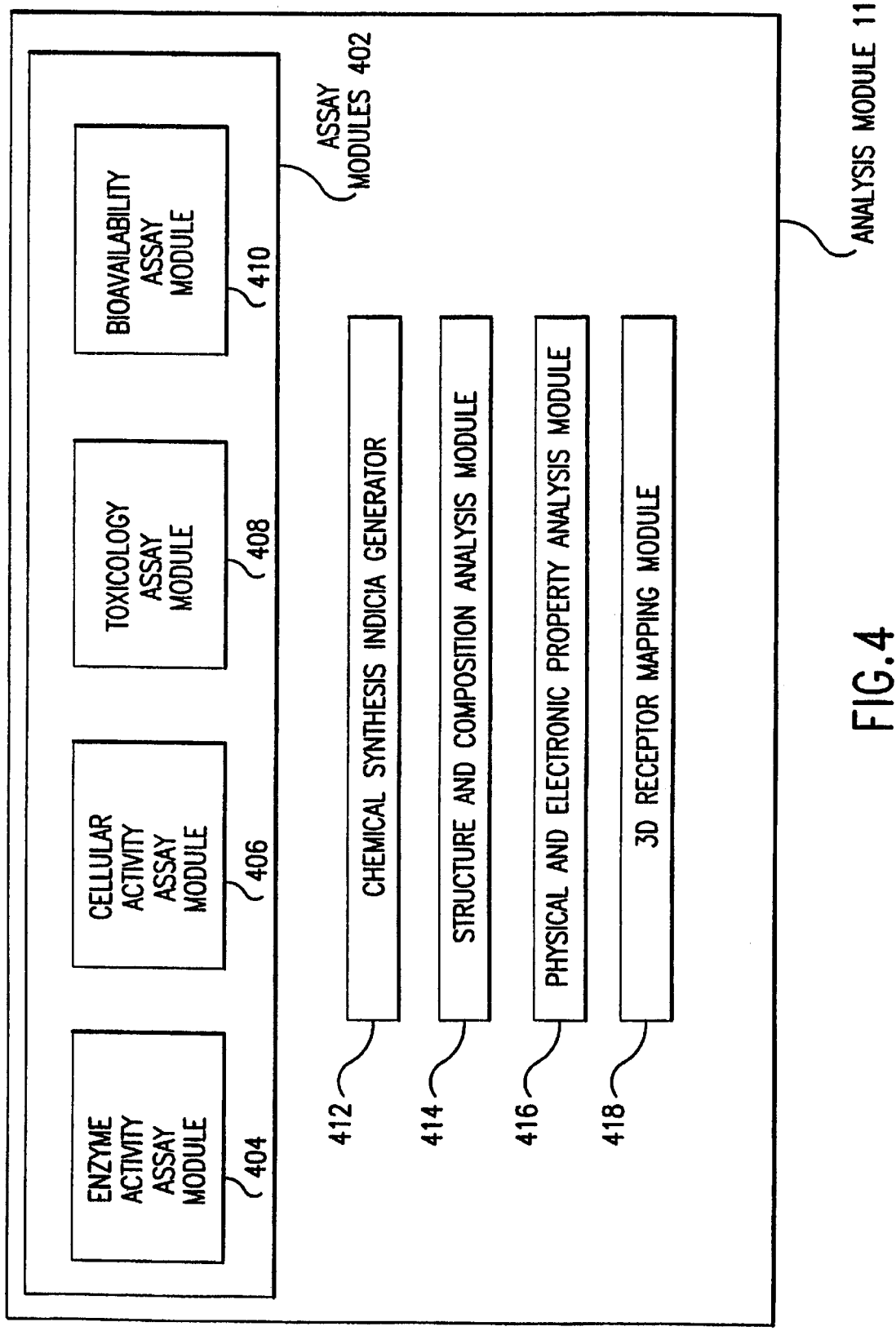
FIG. 4 is a block diagram of an analysis module that can be employed by the lead generation system illustrated in FIG. 3.

FIG. 4 is a more detailed structural block diagram of an embodiment of the Analysis Module(s) 118. The Analysis Module(s) 118 include one or more Assay Modules 402, such as an Enzyme Activity Assay Module 404, a Cellular Activity Assay Module 406, a Toxicology Assay Module 408, and/or a Bioavailability Assay Module 410. The Enzyme Activity Assay Module 404 assays the compounds synthesized by the Synthesis Module(s) 112 using well known procedures to obtain enzyme activity data relating to the compounds. The Cellular Activity Assay Module 406 assays the compounds using well known procedures to obtain cellular activity data relating to the compounds. The Toxicology Assay Module 408 assays the compounds using well known procedures to obtain toxicology data relating to the compounds. The Bioavailability Assay Module 410 assays the compounds using well known procedures to obtain bioavailability data relating to the compounds.

The Enzyme Activity Assay Module 404, Cellular Activity Assay Module 406, Toxicology Assay Module 408, and Bioavailability Assay Module 410 are implemented in a well known manner to facilitate the preparation of solutions, initiation of the biological or chemical assay, termination of the assay (optional depending on the type of assay) and measurement of the results, commonly using a counting device, spectrophotometer, fluorometer or radioactivity detection device. Each of these steps can be done manually (with or without the aid of robots or computers) or by robots, in a well known manner. Raw data is collected and stored on magnetic media under computer control or input manually into a computer. Useful measurement parameters such as dissociation constants or 50% inhibition concentrations can then be manually or automatically calculated from the observed data, stored on magnetic media and output to a relational database.

The Analysis Module(s) 118 optionally include a Structure and Composition Analysis Module 414 to obtain two dimensional structure and composition data relating to the compounds. Preferably, the structure and composition analysis module 414 is implemented using a liquid chromatograph device and/or a mass spectrometer. In one embodiment, a sampling robot (not shown) transfers aliquots from the 96 wells to a coupled liquid chromatography-mass spectrometry system to perform sample analysis.

The Structure and Composition Analysis Module 414 can be utilized to determine product composition and to monitor reaction progress by comparison of the experimental results to the theoretical results predicted by the Synthesis Protocol Generator 202. The Analysis Module(s) 118 can use, but is not limited to, infra-red spectroscopy, decoding of a molecular tag, mass spectrometry (MS), gas chromatography (GC), liquid chromatography (LC), or combinations of these techniques (i.e., GC-MS, LC-MS, or MS-MS). Preferably, the Structure and Composition Analysis Module 414 is implemented using a mass spectrometric technique such as Fast Atom Bombardment Mass Spectrometry (FABSMS) or triple quadrapole ion spray mass spectrometry, optionally coupled to a liquid chromatograph, or matrix-assisted laser desorption ionization time-of-flight mass spectrometry (MALDI-TOF MS). MALDI-TOF MS is well known and is described in a number of references, such as: Brummell et al., *Science* 264:399 (1994); Zambias et al., *Tetrahedron Lett.* 35:4283 (1994), both incorporated herein by reference in their entireties.

Liquid chromatograph devices, gas chromatograph devices, and mass spectrometers suitable for use with the present invention are well known and are commercially available from a number of manufacturers, such as the following:

TABLE 2

GAS CHROMATOGRAPHY

| Manufacturer | City | State | Model |
|---|---|---|---|
| Hewlett-Packard Company | Palo Alto | CA | 5890 |
| Varian Associates Inc. | Palo Alto | CA | |
| Shimadzu Scientific Inst. | Columbia | MD | GC-17A |
| Fisons Instruments | Beverly | MA | GC 8000 |

TABLE 3

LIQUID CHROMATOGRAPHY

| Manufacturer | City | State | Model |
|---|---|---|---|
| Hewlett-Packard Company | Palo Alto | CA | 1050, 1090 |
| Varian Associates Inc. | Palo Alto | CA | |
| Rainin Instrument Co. | Woburn | MA | |
| Shimadzu Scientific Inst. | Columbia | MD | LC-10A |
| Waters Chromatography | Milford | MA | Millenium |
| Perkin-Elmer Corporation | Norwalk | CT | |
| Hitachi Instruments Inc. | San Jose | CA | |

TABLE 4

MASS SPECTROSCOPY

| Manufacturer | City | State | Model |
|---|---|---|---|
| Hewlett-Packard Company | Palo Alto | CA | |
| Varian Associates Inc. | Palo Alto | CA | |
| Kratos Analytical Inc. | Ramsey | NJ | MS80RFAQ |
| Finnigan MAT | San Jose | CA | Vision 2000, TSQ-700 |
| Fisons Instruments | Beverly | MA | API LC/MS, AutoSpec |
| Perkin-Elmer Corporation | Norwalk | CT | API-III |

Modifications to these devices may be necessary to fully automate both the loading of samples on the systems as well as the comparison of the experimental and predicted results. The extent of the modification can vary from instrument to instrument. The nature and implementation of such modifications will be apparent to persons skilled in the art.

The Analysis Module(s) 118 can optionally further include a Chemical Synthesis Indicia Generator 412 that analyzes the structure and composition data obtained by the Structure and Composition Analysis Module 414 to determine which compounds were adequately synthesized by the Synthesis Module(s) 112, and which compounds were not adequately synthesized by the Synthesis Module(s) 112. In an embodiment, the Chemical Synthesis Indicia Generator 412 is implemented using a processor, such as Processor 302, operating in accordance with appropriate control logic, such as Control Logic 304, 306, and/or 308. Preferably, the Control Logic 304, 306, and/or 308 represents a computer program such that the Processor 302 operates in accordance with instructions in the Control Logic 304, 306, and/or 308 to determine which compounds were adequately synthesized by the Synthesis Module(s) 112, and which compounds were not adequately synthesized by the Synthesis Module(s) 112. Persons skilled in the relevant art will be able to produce such Control Logic 304, 306, and/or 308 based on the discussion of the Chemical Synthesis Indicia Generator 412 contained herein.

The Analysis Module(s) 118 can also include a three dimensional (3D) Receptor Mapping Module 418 to obtain three dimensional structure data relating to a receptor binding site. The 3D Receptor Mapping Module 418 preferably determines the three dimensional structure of a receptor binding site empirically through x-ray crystallography and/or nuclear magnetic resonance spectroscopy, and/or as a result of the application of extensive 3D QSAR (quantitative structure-activity relationship) and receptor field analysis procedures, well known to persons skilled in the art and described in: "Strategies for Indirect Computer-Aided Drug Design", Gilda H. Loew et al., *Pharmaceutical Research*, Volume 10, No. 4, pages 475–486 (1993); "Three Dimensional Structure Activity Relationships", G. R. Marshall et al., *Trends In Pharmceutical Science*, 9: 285–289 (1988). Both of these documents are herein incorporated by reference in their entireties.

The functions performed by the Analysis Modules 118 can alternatively be performed by human operators, with or without the aid of robots and/or computers.

The Analysis Module(s) 118 can additionally include a Physical and/or Electronic Property Analysis Module(s) 416 that analyzes the compounds synthesized by the Synthesis Module(s) 112 to obtain physical and/or electronic property data relating to the compounds. Such properties can include water/octanol partition coefficients, molar refractivity, dipole moment, fluorescence etc. Such properties can either be measured experimentally or computed using methods well known to persons skilled in the art.

Referring again to FIG. 3, the Data Storage Device 314 is a read/write high storage capacity device such as a tape drive unit or a hard disk unit. Data storage devices suitable for use with the present invention are well known and are commercially available from a number of manufacturers, such as the 2 gigabyte Differential System Disk, part number FTO-SD8-2NC, and the 10 gigabyte DLT tape drive, part number P-W-DLT, both made by Silicon Graphics, Inc., of Mountain View, Calif. The Reagent Database 138, Compound Database 134, and Structure-Property Database 126 are stored in the Data Storage Device 314.

The Reagent Database 138 contains information pertaining to the reagents in the Reagent Inventory 116. In particular, the Reagent Database 138 contains information pertaining to the chemical substructures, chemical properties, physical properties, biological properties, and electronic properties of the reagents in the Reagent Inventory 116.

The Structure-Property Database 126 stores Structure-Property Data 124, 128 (FIG. 1) pertaining to the compounds that were synthesized by the Synthesis Module(s) 112. Such Structure-Property Data 124, 128 is obtained as a result of the analysis of the compounds performed by the Analysis Module(s) 118, as described above. The Structure-Property Data 124, 128 obtained by the Analysis Module(s) 118 is transferred to and stored in the Structure-Property Database 126 via the Communication Medium 312.

Figure 5:
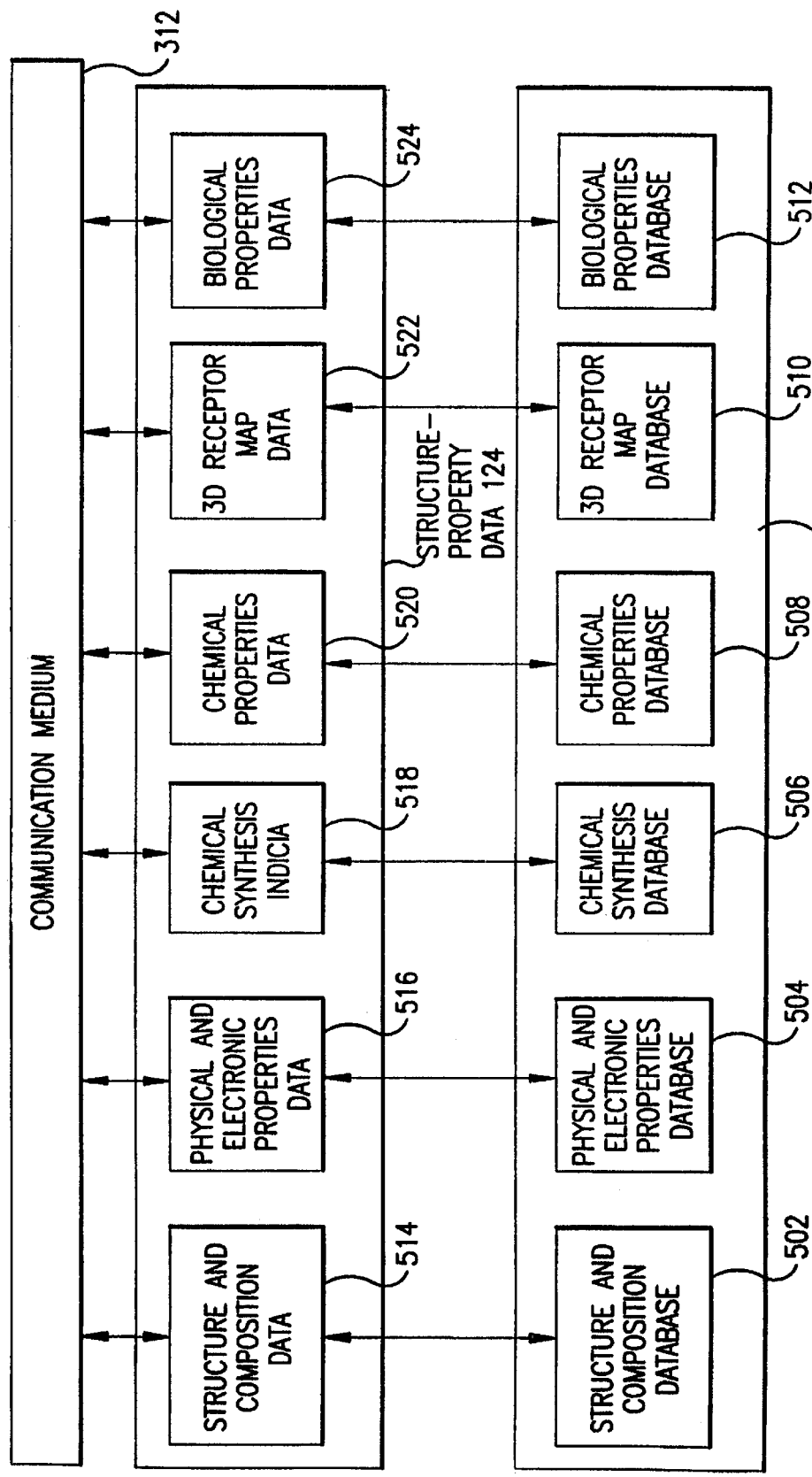
FIG. 5 is a block diagram of a structure-property database that can be employed by the lead generation system illustrated in FIG. 3.

FIG. 5 is a more detailed block diagram of an embodiment of the Structure-Property Database 126. The Structure-Property Database 126 includes a Structure and Composition Database 502, a Physical and Electronic Properties Database 504, a Chemical Synthesis Database 506, a Chemical Properties Database 508, a 3D Receptor Map Database 510, and a Biological Properties Database 512. The Structure and Composition Database 502 stores Structure and Composition Data 514 pertaining to compounds synthesized by the Synthesis Module(s) 112 and analyzed by the Analysis Module(s) 118. Similarly, the Physical and Electronic Properties Database 504, Chemical Synthesis Database 506, Chemical Properties Database 508, 3D Receptor Map Database 510, and Biological Properties Database 512 store Physical and Electronic Properties Data 516, Chemical Synthesis Data 518, Chemical Properties Data 520, 3D Receptor Map Data 522, and Biological Properties Data 524, respectively, pertaining to compounds retrieved from the Chemical Inventory 110 and/or synthesized by the Synthesis Module(s) 112, and analyzed by the Analysis Module(s) 118. The Structure and Composition Data 514, Physical and Electronic Properties Data 516, Chemical Synthesis Data 518, Chemical Properties Data 520, 3D Receptor Map Data 522, and Biological Properties Data 524 collectively represent the Structure-Property Data 124, 128.

In an embodiment, the Structure and Composition Database 502, Physical and Electronic Properties Database 504, Chemical Synthesis Database 506, Chemical Properties Database 508, 3D Receptor Map Database 510, and Biological Properties Database 512 each include one record for each chemical compound retrieved from the Chemical Inventory 110 and/or synthesized by the Synthesis Module(s) 112 and analyzed by the Analysis Module(s) 118 (other database structures could alternatively be used).

7. Operation of the Present Invention

The operation of the lead generation/optimization system 100 shall now be described in detail with reference to the process flowchart 600 of FIG. 6. Steps 602–618 in process flowchart 600 represent a preferred method for identifying chemical compounds having desired properties.

The lead generation/optimization system 100 implements an iterative process where, during each iteration:

(1) a set of Selection Criteria 104 and/or one or more Objective Functions are defined (step 602);

(2) a Directed Diversity Library 108 is selected (step 604);

(3a) compounds in the Directed Diversity Library 108 are retrieved from the Chemical Inventory 110 (step 606); and/or (3b) compounds in the Directed Diversity Library 108 that were not retrieved from the Chemical Inventory 110 are synthesized (step 608);

(4) the compounds in the Directed Diversity Library 108 are analyzed to obtain Structure-Property Data 124 pertaining to compounds (step 612);

(5) the Structure-Property Data 124 are stored in a Structure-Property Database 126 (step 614);

(6) new Leads 122 are identified and classified (step 616);

(7) Structure-Property Models with enhanced predictive and discriminating capabilities are constructed and/or refined to allow the selection and/or refinement of a new set of Selection Criteria 104 for the next iteration (step 618).

In an embodiment, steps 602–618 of flowchart 600 are performed during each iteration of the iterative process as indicated by control line 620 in flowchart 600.

Figure 6:
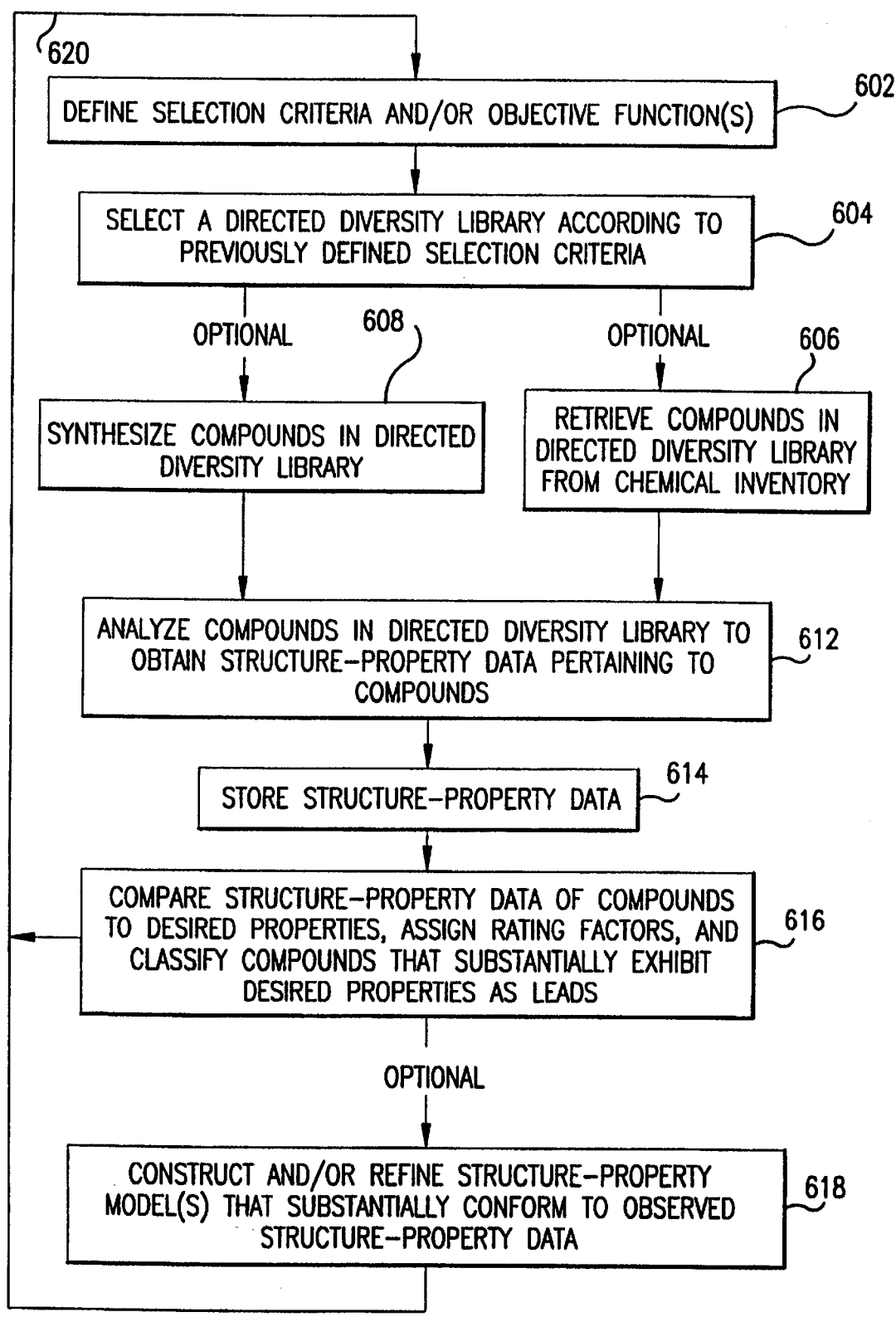
FIG. 6 is a process flowchart illustrating an iterative method for identifying chemical compounds having desired properties.

Referring to FIG. 6, the process begins at step 602, where the Experiment Planner 130 defines Selection Criteria 104 and/or one or more Objective Functions 105. The Experiment Planner 130 defines Selection Criteria 104 and/or Objective Functions 105 based on current Structure-Property Data 124 and Historical Structure-Property Data 128. Historical Structure-Property Data 128 can be identified from previous iterations of the lead generation/optimization system 100 and/or from other M o independent experiments. The Experiment Planner 130 can also define Selection Criteria 104 and/or Objective Functions 105 based on one or more of: Compound Data 132; Reagent Data 136; Desired Properties 120; and Structure-Property Models 192. The Selection Criteria 104 and/or Objective Functions 105 are sent to the Selector 106. Additional details of step 602 are provided below, in the description of the next iteration of the process.

In step 604, the Selector 106 selects a Directed Diversity Library 108. The Selector 106 uses the Selection Criteria 104 and/or Objective Functions 105 that were defined by the Experiment Planner 130 in step 603. The Selector 106 can use a stochastic (or exhaustive, if possible) search/optimization technique. The search can include, but is not limited to, Monte-Carlo Sampling 834, Simulated Annealing 836, Evolutionary Programming 838, and/or a Genetic Algorithm 840, to produce a list of compounds that best satisfy all the Selection Criteria 104 in the manner specified by the Objective Function 105, and will comprise the Directed Diversity Library 108 for the next iteration.

In one embodiment, the Selector 106 selects the Directed Diversity Library 108 for the next iteration using a Monte-Carlo Sampling 834 or Simulated Annealing 836 algorithm. In this embodiment, a collection of compounds that satisfies all the constraints specified by the Experiment Planner 130 represents a 'state', and is encoded in a manner that is most appropriate given those constraints. Thus, the precise encoding of a state can vary, depending on some of the Selection Criteria 104 specified by the Experiment Planner 130.

Figure 18:
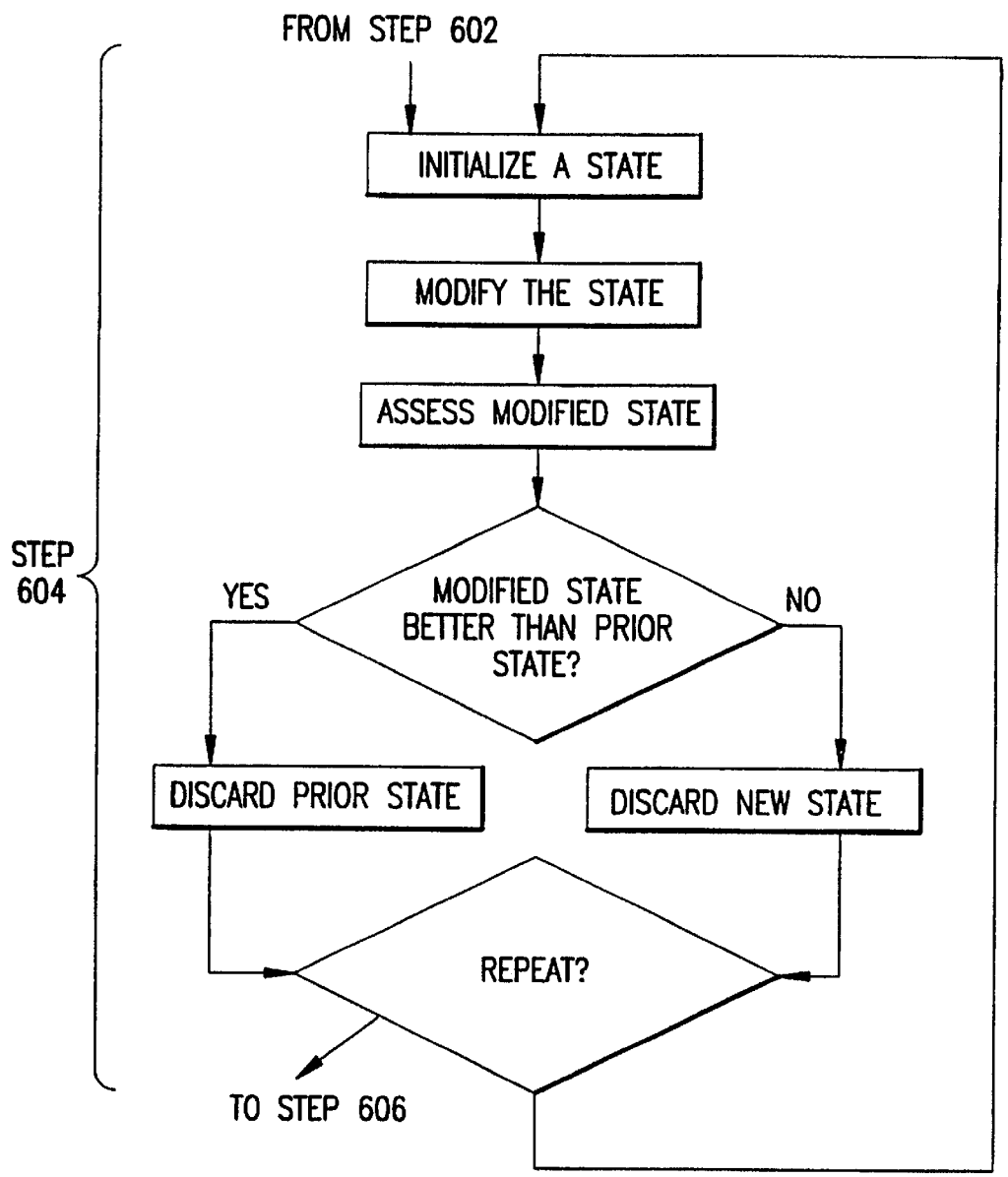
FIG. 18 is a process flowchart illustrating a method for selecting a directed diversity library, in accordance with the present invention.

Referring to the process flowchart of FIG. 18, the process of step 604 is illustrated in greater detail for where a Monte-Carlo Sampling 834 or Simulated Annealing 836 algorithm is used.

In step 1804, a state, i.e., the collection of compounds that will comprise the Directed Diversity Library 108 for the next iteration, is initialized preferably at random. Other initialization approaches could alternatively be used, such as biased or human input. The state is initialized by selecting a set of compounds and/or a set of reagents preferably at random.

In steps 1806–1816, the state is gradually refined by a series of small stochastic 'steps'. The term 'step' means a stochastic (random or partially random) modification of the state's composition, i.e. the compounds comprising the state.

In step 1806, the state is modified. Modification can include sending an randomly generated state to the Server 1204 as Compound List 1302 and receiving Values 1304 for the compounds in the Compound List 1302. The initial state can then be modified, for example, by replacing a compound currently in the state with a compound not currently in the state, or by replacing a building block of one or more compounds currently in the state. The new state can be sent to the Server 1204 as Compound List 1302 and Values 1304 can be returned for the new state.

In step 1808, the quality of the new state can be assessed using the Objective Function 105 specified by the Experiment Planner 130. The quality can be assessed by comparing the new state to the old state using the Metropolis criterion. Alternatively, any other suitable comparison criterion can be used.

In step 1810, if the new state is approved, processing proceeds to step 1812, where the Selector 106 replaces the old state with the new state. If the new state is not approved, processing proceeds to step 1814, where the Selector 106 discards the new state.

From steps 1812 and 1814, processing proceeds to step 1816, where the Selector 106 determines whether to repeat steps 1806–1814 or use the current state as the next Directed Diversity Library 108.

Steps 1806–1816 can be performed under control of a Monte-Carlo Sampling protocol 834, a Simulated Annealing protocol 836, or variants thereof, which are well known to persons skilled in the art. However, it should be understood that the system of the present invention is not limited to these embodiments.

For example, the Selector 106 can use Evolutionary Programming 838 or Genetic Algorithms 840, where the population of states (or chromosomes) is initialized at random and is allowed to evolve through the repeated application of genetic operators, such as crossover, mutation, and selection. The genetic operators alter the composition of the states, either individually (e.g. mutation), or by mixing elements of two or more states (e.g. crossover) in some prescribed manner. Selection is probabilistic, and is based on the relative fitness of these states as measured by the Objective Function 105. As in the case of Monte-Carlo Sampling 834 and Simulated Annealing 836 described above, the states (or chromosomes) are encoded in a manner that is most appropriate given the constraints specified by the Experiment Planner 130.

In addition to Evolutionary Programming 838 and Genetic Algorithms 840, the Selector 106 can also use any other suitable search/optimization algorithm to identify the optimal (or a nearly optimal) Directed Diversity Library 108.

Thus, the precise encoding of a state in step 604 can vary, depending on, among other things, the Selection Criteria 104 specified by the Experiment Planner 130. The implementation of these methods should be straightforward to persons skilled in the art.

Several examples are provided below to illustrate how one or more Selection Criteria 104 can be combined by one or more Objective Functions 105, and how the Selection Criteria 104 and Objective Functions 105 can be used to select a Directed Diversity Library 108 for a next iteration. These examples are provided to illustrate the present invention, not to limit it.

In the first example, the Selector 106 uses Simulated Annealing 836 to identify a set of 50 compounds from a 10,000-membered Compound Library 102 that maximize the Objective Function 105 given by EQ. 13:

$$f(S)=D(S) \qquad \text{EQ. 13}$$

using the Molecular Diversity Criterion described in EQ. 4, and a Euclidean distance measure defined in a normalized 2-dimensional property space (in the example below, the properties of these 10,000 compounds represent uniformly distributed random deviates in the unit square). In a preferred embodiment, the system encodes a state by a pair of index lists, one containing the indices of the compounds currently in the set (Included Set), and another containing the indices of the compounds not currently in the set (Excluded Set). A step (i.e. a modification of the composition of the current state) is performed by swapping one or more indices from the Included and Excluded Sets. The search was carried out in 30 temperature cycles, using 1,000 sampling steps per cycle, an exponential cooling schedule, and the Metropolis acceptance criterion.

Figure 14:
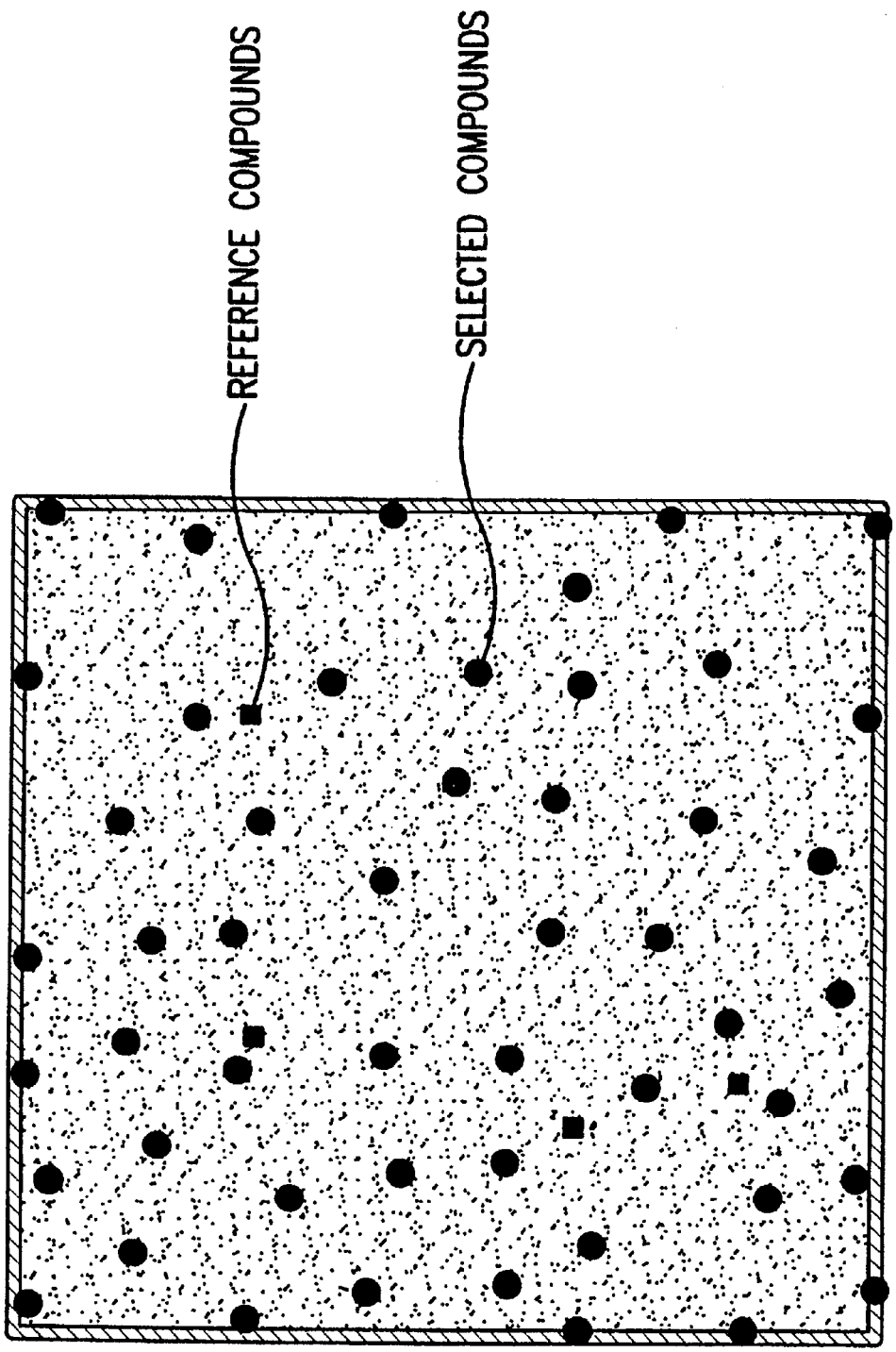
FIG. 14 illustrates a distribution of compounds in a directed diversity library.

The results of the simulation are shown in FIG. 14, where, as the simulation progresses, the selected compounds assume an optimal distribution, i.e. the diversity (spread) of these compounds is maximized. The set of compounds highlighted in FIG. 14 represent a Directed Diversity Library 108 for the next iteration, selected according to the prescribed Selection Criteria 104 and the Objective Function 105 in EQ. 13.

In the second example, the Selector 106 uses Simulated Annealing 836 to identify a set of 50 compounds from a 10,000-membered Compound Library 102 that maximize the Objective Function 105 given by EQ. 14:

$$f(S)=-M(S,L) \qquad \text{EQ. 14}$$

using the Molecular Similarity Criterion described in EQ. 8, a set of 4 reference compounds (chosen at random), and a Euclidean distance measure defined in a normalized 2-dimensional property space. As in the previous example, the properties of these 10,000 compounds represent uniformly distributed random deviates in the unit square. The search was carried out in 30 temperature cycles, using 1,000 sampling steps per cycle, an exponential cooling schedule, and the Metropolis acceptance criterion.

Figure 15:
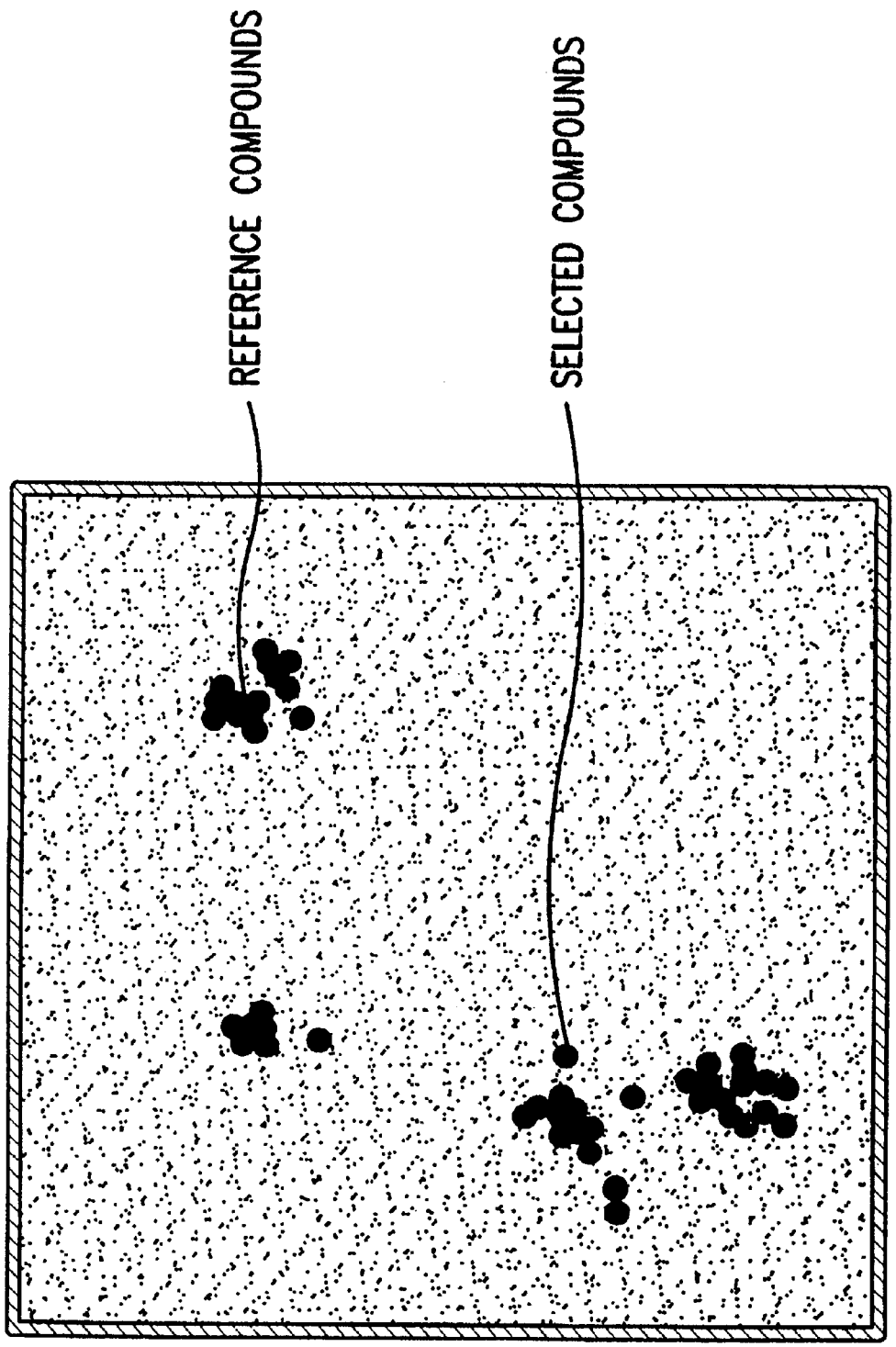
FIG. 15 illustrates another distribution of compounds in a directed diversity library.

The results of the simulation are shown in FIG. 14. As can be seen from FIG, 15, as the simulation progresses, the selected compounds assume an optimal distribution, i.e. the selected compounds cluster tightly around the specified reference compounds. The set of compounds highlighted in FIG. 15 represent a Directed Diversity Library 108 for the next iteration, selected according to the prescribed Selection Criteria 104 and the Objective Function 105 in EQ. 14.

In the third example, the Selector 106 uses Simulated Annealing 836 to identify a set of 50 compounds from a 10,000-membered Compound Library 102 that maximize the Objective Function 105 given by EQ. 15:

$$f(S)=2D(S)-M(S,L) \qquad \text{EQ. 15}$$

using the Molecular Diversity Criterion described in EQ. 4, the Molecular Similarity Criterion described in EQ. 8, a set of 4 reference compounds (chosen at random), and a Euclidean distance measure defined in a normalized 2-dimensional property space. As in the previous example, the properties of these 10,000 compounds represent uniformly distributed random deviates in the unit square. The search was carried out in 30 temperature cycles, using 1,000 sampling steps per cycle, an exponential cooling schedule, and the Metropolis acceptance criterion.

Figure 16:
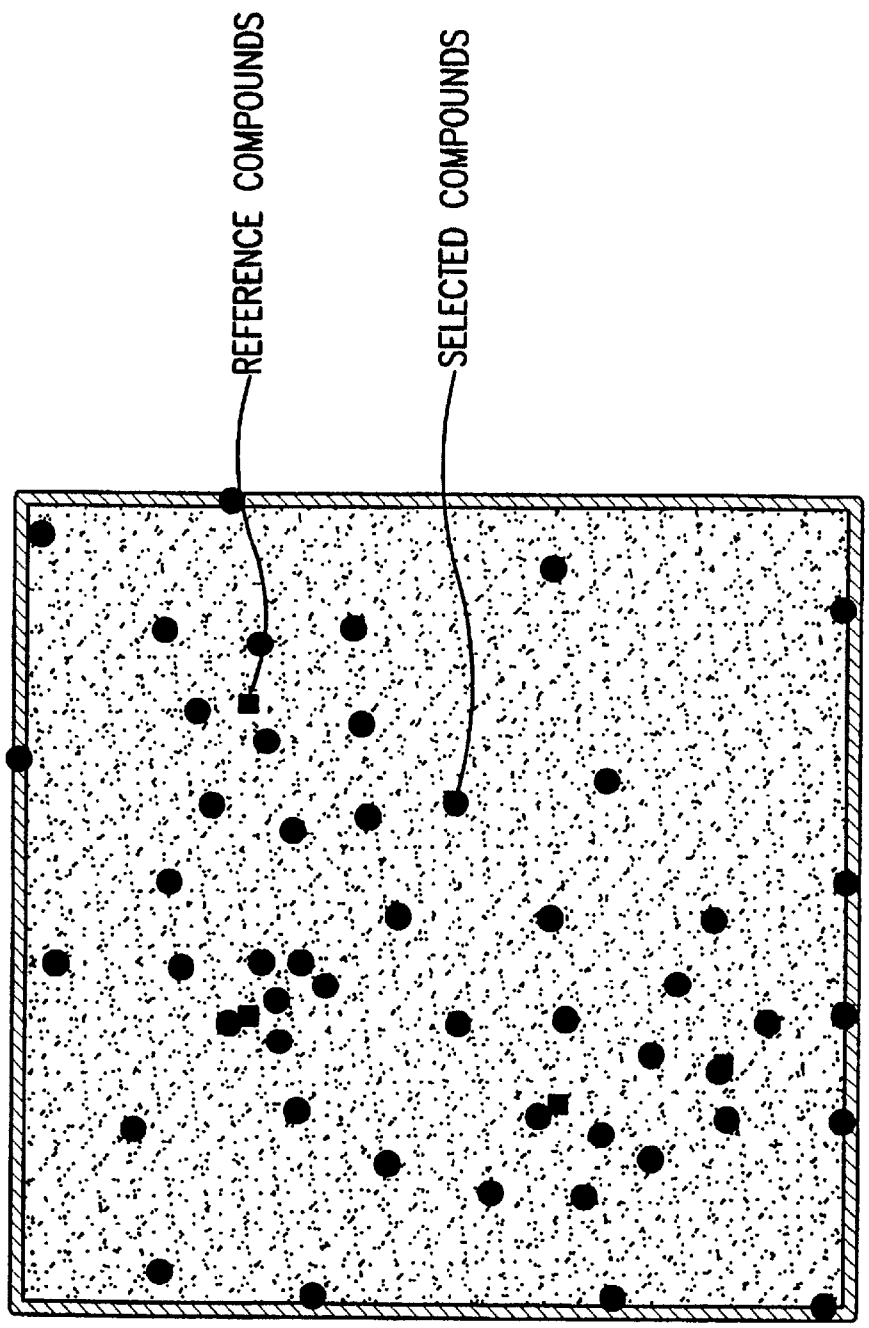
FIG. 16 illustrates another distribution of compounds in a directed diversity library.

EQ. 15 represents a Multi-Objective Function, i.e. an Objective Function 105 that combines two, rather than one, Selection Criteria 104. The Objective Function 105 in EQ. 15 represents an Objective Function 105 that combines molecular diversity and molecular similarity. That is, the Objective Function 105 in EQ. 15 favors solutions that are both diverse and focused. The results of the simulation are shown in FIG. 16. As can be seen from FIG. 16, as the simulation progresses, the selected compounds assume an optimal distribution, i.e. the selected compounds become both diverse and focused. The set of compounds highlighted in FIG. 16 represent a Directed Diversity Library 108 for the next iteration, selected according to the prescribed Selection Criteria 104 and the Objective Function 105 in EQ. 15.

In optional steps 606 and 608, compounds specified in the Directed Diversity Library 108 are retrieved or synthesized. Steps 606 and 608 are said to be optional because one or both of steps 606 and 608 can be performed. In one embodiment, steps 606 and 608 are both employed, when compounds specified in the Directed Diversity Library 108 were previously synthesized, they are retrieved from a chemical inventory in step 606 rather than re-synthesized; when compounds specified in the Directed Diversity Library 108 were not previously synthesized, they are synthesized in step 608. Alternatively, either of steps 606 and 608 could be employed exclusively or could be employed with other methods.

In optional step 606, the Directed Diversity Manager 310 retrieves compounds specified in the Directed Diversity Library 108 that are available in the Chemical Inventory 110. The Chemical Inventory 110 represents any source of available compounds including, but not limited to, a corporate chemical inventory, a supplier of commercially available chemical compounds, a natural product collection, etc.

In one embodiment, the Directed Diversity Manager 310 searches the Chemical Inventory 110 to identify and retrieve existing compounds of the Directed Diversity Library 108. Alternatively, a subset of the Directed Diversity Library 108, as determined by user input, for example, can be searched for and retrieved from the Chemical Inventory 110.

In optional step 608, the compounds in the Directed Diversity Library 108 that were not retrieved from the Chemical Inventory 110 in step 606, are synthesized. In one embodiment, step 608 is performed by one or more are automated robotic Synthesis Modules 112 that receive Robotic Synthesis Instructions 204 from the Synthesis Protocol Generator 202.

More specifically, the Directed Diversity Manager 310 selects Reagent Data 136 from the Reagent Database 138 and generates Robotic Synthesis Instructions 204. The Reagent Data 136 identifies Reagents 114 in the Reagent Inventory 116 that are to be mixed by the one or more Synthesis Modules 112. The Robotic Synthesis Instructions 204 identify the manner in which such Reagents 114 are to be mixed. The manner of mixing can include identifying Reagents 114 to be mixed together, and specifying chemical and/or physical conditions for mixing, such as temperature, length of time, stirring, etc. The one or more Synthesis Modules 112 synthesize compounds in the Directed Diversity Library 108, using selected Reagents 114 from the Reagent Inventory 116, in accordance with the Robotic Synthesis Instructions 204.

In another embodiment, optional step 608 is performed semi-automatically or manually. The chemical compounds that were retrieved from the Chemical Inventory 110 and/or synthesized by the Synthesis Modules 112 (or synthesized manually) collectively represent physical compounds from a Directed Diversity Library 108.

In step 612, one or more Analysis Modules 118 analyze the compounds in the Directed Diversity Library 108 to obtain Structure-Property data 124, pertaining to the compounds. The Analysis Modules 118 receive compounds that were retrieved from the Chemical Inventory 110 in step 606 and compounds that were synthesized by the Synthesis Modules 112 in step 610.

In one embodiment of step 612, one or more Assay Modules 402 can robotically assay the chemical compounds in the Directed Diversity Library 108 to obtain Physical Properties Data 516, Chemical Properties Data 520 and Biological Properties Data 524, pertaining to the chemical compounds.

For example, the Enzyme Activity Assay Module 404 can robotically assay the chemical compounds using well known assay techniques to obtain enzyme activity data relating to the compounds. Enzyme activity data can include inhibition constants $K_i$, maximal velocity $V_{max}$, etc. The Cellular Activity Assay Module 406 can robotically assay the compounds using well known assay techniques to obtain cellular activity data relating to the compounds. The Toxicology Assay Module 408 can robotically assay the compounds using well known assay techniques to obtain toxicology data relating to the compounds. The Bioavailability Assay Module 410 can robotically assay the compounds using well known assay techniques to obtain bioavailability data relating to the compounds. The enzyme activity data, cellular activity data, toxicology data, and bioavailability data represent the Physical Properties Data 516, Chemical Properties Data 520 and Biological Properties Data 524. Alternatively, Physical Properties Data 516 can be obtained by the Physical and Electronic Property Analysis Module 416.

Also during step 612, the Physical and Electronic Properties Analysis Module 416 can analyze the chemical compounds contained in the Directed Diversity Library 108 to obtain Electronic Properties Data 516 pertaining to the chemical compounds. The Electronic Properties Data 516 is stored in the Physical and Electronic Properties Database 504 during step 614.

Also during step 612, the 3D receptor mapping module 418 can obtain 3D Receptor Map Data 522 representing the three-dimensional structure pertaining to a receptor binding site being tested. The 3D Receptor Mapping Module 418 preferably determines the three-dimensional structure of the receptor binding site empirically through X-ray crystallography, nuclear magnetic resonance spectroscopy, and/or as a result of the application of 3D QSAR and receptor field analysis procedures. The Receptor Map Data 522 is stored in the Receptor Map Database 510 during step 614.

Also during step 612, an optional Structure and Composition Analysis Module 414 can analyze the chemical compounds contained in the Directed Diversity Library 108 to obtain Structure and Composition Data 514 pertaining to the chemical compounds. The Structure and Composition Data 514 is stored in the Structure and Composition Database 502 during step 614.

In one embodiment, step 612 is performed robotically, under control of one or more computer programs. Alternatively, step 612 can be performed manually or by some combination of the two.

In step 614, the one or more Analysis Modules 118 store the Structure-Property Data 124 obtained in step 612. The Structure-Property Data 124 can be stored in the Structure-Property Database 126 of the Data Storage Device 314. The Structure-Property Database 126 can also store Historical Structure-Property Data 128. Historical Structure-Property Data 128 can be associated with chemical compounds that were synthesized and analyzed in previous iterations by the Synthesis Modules 112 and the Analysis Modules 118, respectively. Historical Structure-Property Data 128 can also include other pertinent Structure-Property Data obtained from independent experiments.

Using the example from step 612, the Physical Properties Data 516 can be stored in the Physical and Electronic Properties Database 504, the Chemical Properties Data 520 can be stored in the Chemical Properties Database 508 and the Biological Properties Data 524 can be stored in the Biological Properties Database 512.

In one embodiment of the present invention, during execution of steps 612 and 614, a determination is made as to whether a chemical compound was adequately synthesized. The determination is made by the Analysis Modules 118, as shall now be described.

Figure 7:
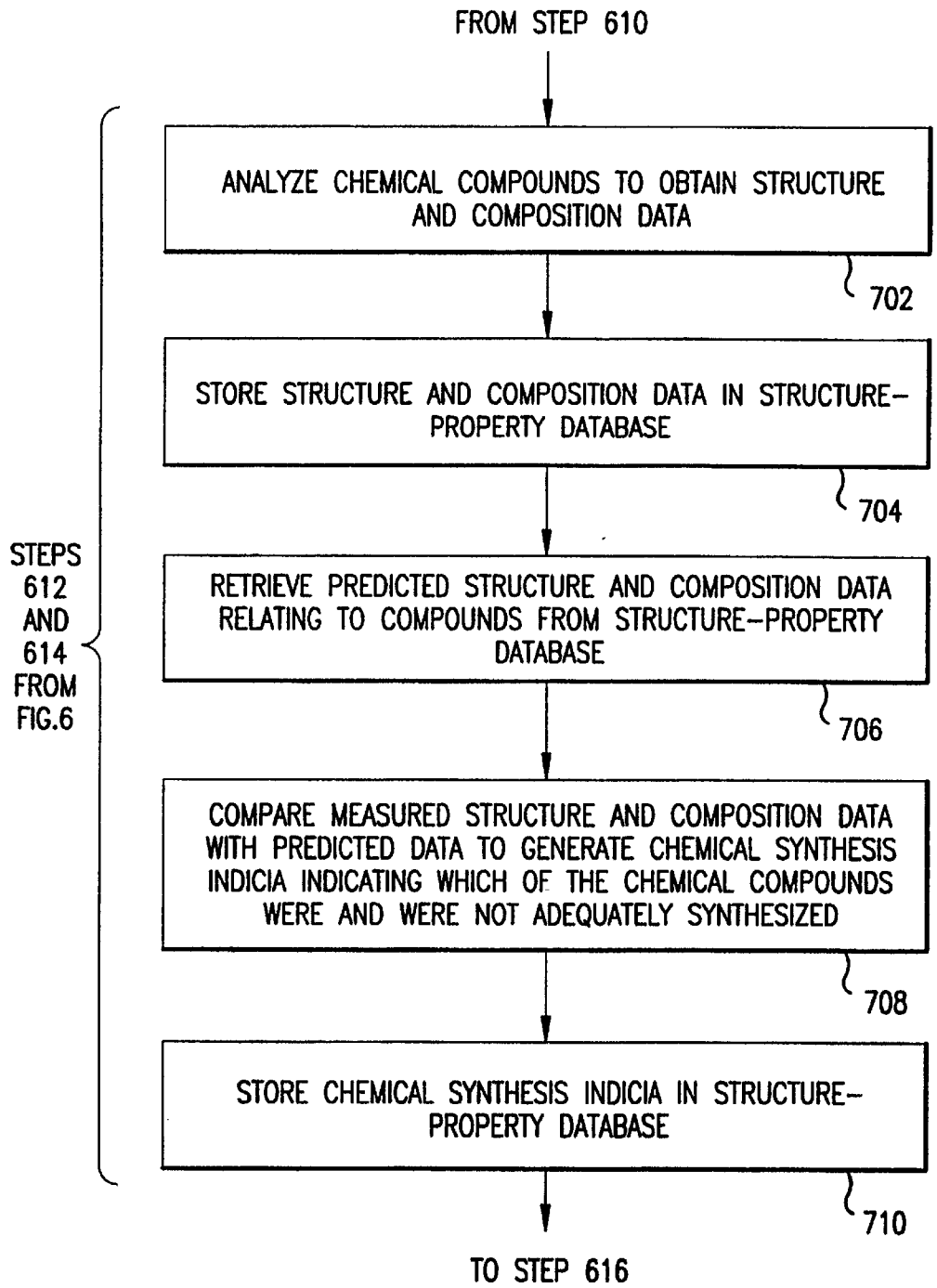
FIG. 7 is a process flowchart illustrating a method for performing steps 612 and 614 of the method illustrated in FIG. 6.

Referring to FIG. 7, the process begins at step 702, where the Structure and Composition Analysis Module 414 analyzes chemical compounds to obtain Structure and Composition Data 514. Preferably, the Structure and Composition Analysis Module 414 analyzes the chemical compounds using well known mass spectra analysis techniques.

In step 704, the Structure and Composition Data 514 is stored in a Structure and Composition Database 502 that forms part of the Structure-Property Database 126.

In step 706, the Chemical Synthesis Indicia Generator 412 retrieves predicted Structure and Composition Data 514 relating to the compounds. The data is retrieved from the Structure-Property Database 126. Preferably, the retrieved data includes predicted mass and structural data for the compounds.

In step 708, the Chemical Synthesis Indicia Generator 412 compares the measured Structure and Composition Data 514 to the predicted data to generate Chemical Synthesis Indicia 518. Based on the comparisons, the Chemical Synthesis Indicia 518 identifies chemical compounds that were adequately synthesized and chemical compounds that were not adequately synthesized.

Preferably, during step 708, the Chemical Synthesis Indicia Generator 412 compares the measured mass of each compound to the predicted mass of the compound. If the measured mass and the predicted mass differ by less than a predetermined amount, the Chemical Synthesis Indicia Generator 412 determines that the chemical compound was adequately synthesized. If the measured mass and the predicted mass differ by more than the predetermined amount, the Chemical Synthesis Indicia Generator 412 determines that the chemical compound was not adequately synthesized. This predetermined amount can depend on the sensitivity of the instrument used for the structure and composition analysis.

In step 710, the Chemical Synthesis Indicia Generator 412 generates Chemical Synthesis Indicia 518 pertaining to the compounds in the Directed Diversity Library 108, and stores such Chemical Synthesis Indicia 518 in the Chemical Synthesis Database 506. The Chemical Synthesis Indicia 518 for each compound is a first value (such as "1") if the compound was adequately synthesized (as determined in step 708), and is a second value (such as "0") if the compound was not adequately synthesized.

After step 710, control passes to step 616.

In step 616, the Directed Diversity Manager 310 compares the Structure-Property Data 124, pertaining to the compounds in the Directed Diversity Library 108, to the Desired Properties 120. The Desired Properties 120 might have been entered by human operators using the input device 316, or read from a computer file. The Directed Diversity Manager 310 compares the data to determine whether any of the compounds substantially conforms to the Desired Properties 120. When a compound substantially conforms to the Desired Properties 120, it can be classified as a Lead compound 122.

When an insufficient number of compounds substantially exhibit the Desired Properties 120, (i.e., an insufficient number of Lead Compounds 122), the compounds can be rated in order to select new Leads 122. The Directed Diversity Manager 310 can assign one or more rating factors to each compound in the Directed Diversity Library 108, based on how closely the compound's properties match the Desired Properties 120. The one or more rating factors can be represented by numerical or linguistic values. Numerical rating factors represent a sliding scale between a low value, corresponding to a property profile far from the Prescribed Set of Properties 120, and a high value, corresponding to a property profile identical, or very similar, to the Prescribed Set of Properties 120. Linguistic rating factors can include values such as "poor," "average," "good," "very good," etc.

In optional step 618, one or more Structure-Property Models 192 are generated and/or refined. Structure-Property Models 192 are generated and/or refined to conform to observed Structure-Property Data 124 and Historical Structure-Property Data 128. The resulting Structure-Property Models 192 can be used by the Experiment Planner 130 and/or the Selector 106 to predict the properties of compounds in the Compound Library 102 whose real properties are hitherto unknown. The Structure-Property Models can be used by the Experiment Planner 130 to define and/or refine a set of Selection Criteria 104 that depend upon the predictions of the Structure-Property Models.

Figure 17:
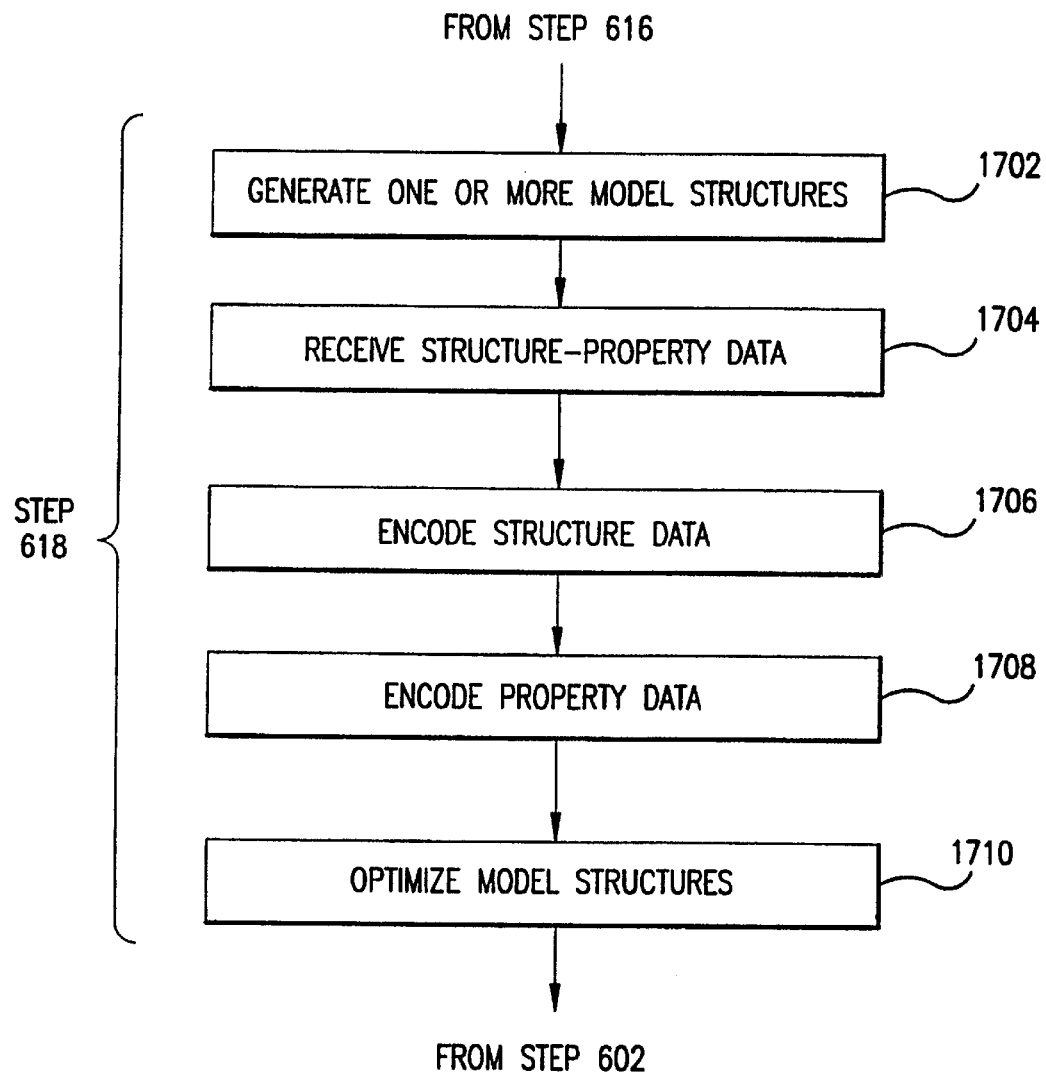
FIG. 17 is a process flowchart illustrating a method for generating structure-property models in accordance with the present invention.

Referring to the process flowchart of FIG. 17, step 618 shall now be described in detail. The process begins at step 1702 where one or more Model Structures 820 are defined by Structure-Property Model Generator 800. The Structure-Property Model Generator 800 can defines Model Structures 820 based on Statistics 802, Neural Networks 804, Fuzzy Logic 806, and/or other Model-Specific Methods 808. The Model Structure 820 can combine elements of Statistics 802, Neural Networks 804, Fuzzy Logic 806, and/or Model-Specific Methods 808. Such Model Structures 820 are hereafter referred to as Hybrid Model Structures or Hybrid Models.

In step 1704, Structure-Property Model Generator 800 receives Structure-Property Data 124 and 128. Structure-Property Data 124 and 128 is separated into Structure Data 824 and Property Data 828.

In step 1706, Structure Data 824 is encoded as Encoded Structure Data 826. Structure Data 824 is encoded in a form that is appropriate for the particular Model Structure 820.

In step 1708, Property Data 828 is encoded as Encoded Property Data 830. Property Data 828 is encoded in a form that is appropriate for the particular Model Structure.

In step 1710, the Trainer 822 optimizes, or trains, the Model Structure 820 that was generated in step 1702. Trainer 822 uses Encoded Structure Data 826, and Encoded Property Data 830 to derive one or more Structure-Property Models 842. Trainer 822 uses one or more of Gradient Minimization 832, Monte-Carlo Sampling 834, Simulated Annealing 836, Evolutionary Programming 838, and/or a Genetic Algorithm 840, depending upon the type of Structure Model 820 that is being optimized.

After step 1710, step 618 is complete and control passes back to step 602 for defining another set of Selection Criteria 104 and/or Objective Functions 105 and then to step 604 for selecting another Directed Diversity Library 108 to analyze. The Directed Diversity Library 108 for the next iteration can be selected using one or more Selection Criteria 104, one or more Objective Functions 105, and one or more selection phases. As used herein, a selection phase refers to a single run of the Selector 106 using a Monte-Carlo Sampling 834, Simulated Annealing 836, Evolutionary Programming 838, and/or a Genetic Algorithm 840.

8. Conclusions

The present invention has been described above with the aid of functional building blocks illustrating the performance of specified functions and relationships thereof. The boundaries of these functional building blocks have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for identifying one or more target chemical compounds having desired properties, comprising the steps of:

(1) identifying an electronically stored library of chemical compounds;

(2) receiving a list of one or more desired properties that the one or more target chemical compounds shall possess;

(3) generating a set of one or more selection criteria from the list of one or more desired properties, wherein said set of one or more selection criteria includes one or more functions that receive property values for the one or more chemical compounds and that return one or more selection criteria values for the one or more chemical compounds;

(4) picking one or more initial sets of chemical compounds from the library of chemical compounds, each said one or more initial sets of chemical compounds including a plurality of chemical compounds, wherein a plurality of said one or more initial sets of chemical compounds are not identical to one another;

(5) using the set of one or more selection criteria and properties values for the one or more chemical compounds in the one or more initial sets of chemical compounds to calculate selection criteria values for the one or more initial sets of chemical compounds, whereby the selection criteria values indicate an extent to which the one or more initial sets of chemical compounds meet the set of one or more selection criteria;

(6) picking one or more new sets of chemical compounds from the library of chemical compounds, each said one or more new sets of chemical compounds including a plurality of chemical compounds, wherein a plurality of said one or more new sets of chemical compounds are not identical to one another and wherein at least on of said one or more new sets of chemical compounds are not identical to at least one of said one or more initial sets of chemical compounds;

(7) using the set of one or more selection criteria and property values for the one or more chemical compounds in the one or more new sets of chemical compounds to calculate selection criteria values for the one or more new sets of chemical compounds, whereby the selection criteria values indicate an extent to which the one or more new sets of chemical compounds meet the set of one or more selection criteria;

(8) repeating steps (6) and (7) a plurality of times;

(9) selecting a first set of chemical compounds from the one or more initial sets of chemical compounds and the one or more new sets of chemical compounds, based on a comparison of the respective selection criteria values;

(10) obtaining physical samples of the first set of chemical compounds;

(11) experimentally determining structure-property data from the physical samples of said first set of chemical compounds; and

(12) determining, from at least the experimentally determined structure-property data of the first set of chemical compounds, whether any of the chemical compounds in the first set of chemical compounds exhibit one or more properties that are similar to one or more of the desired properties that one or more target chemical compounds shall possess.

2. The method according to claim 1, further comprising the steps of:

(13) updating the property values for the one or more chemical compounds with the experimentally determined structure-property data obtained in step (11); and

(14) repeating steps 1–12, using the updated property values for the one or more chemical compounds in steps (5), (7), and (8).

3. The method according to claim 2, wherein step (14) comprises the step of generating a second set of one or more selection criteria and using the second set of selection criteria when repeating steps in steps (5), (7), and (8).

4. The method according to claim 3, wherein step (14) further comprises the step of revising the first set of one or more selection criteria to generate the second set of one or more selection criteria.

5. The method according to claim 4, wherein step (14) further comprises the step of revising one or more of the one or more functions of the first set of one or more selection criteria.

6. The method according to claim 2, wherein step (14) further comprises the step of repeating steps 1–12, using a second library of chemical compounds.

7. The method according to claim 6, wherein the first and second libraries are the same libraries.

8. The method according to claim 6, wherein the first and second libraries are not the same libraries.

9. The method according to claim 6, wherein step (14) further comprises the step of adding one or more chemical compounds to the first library of chemical compounds to generate the second library of chemical compounds.

10. The method according to claim 6, wherein step (14) further comprises the step of removing one or more chemical compounds from the first library of chemical compounds to generate the second library of chemical compounds.

11. The method according to claim 1, wherein step (3) comprises the steps of:

(a) generating one or more objective functions that describe an extent to which a set of one or more chemical compounds shall satisfy one or more selection criteria.

12. The method according to claim 11, wherein the objective function comprises one or more multi-objective functions.

13. The method according to claim (1), wherein step (3) comprises the step of:

(a) generating one or more structure-property models that predict one or more desired properties of chemical compounds.

14. The method according to claim 1, wherein step (6) comprises the step of replacing one or more compounds in one or more of the initial sets of chemical compounds to generate the one or more of the new sets of chemical compounds.

15. The method according to claim 1, wherein steps (5) through (9) are implemented using one or more of the following techniques:

(a) Monte Carlo;

(b) simulated annealing;

(c) evolutionary programming; and (d) genetic algorithms.

16. The method according to claim 1, wherein step (3) comprises the step of generating a function that returns an indication of diversity between a plurality of the compounds.

17. The method according to claim 1, wherein step (3) comprises the step of generating a function that returns an indication of a similarity between one or more of the compounds and one or more reference compounds.

18. The method according to claim 1, wherein step (3) comprises the step of generating a function that returns an indication of one or more of the following:
   a cost of synthesizing one or more of the compounds;
   a cost of screening one or more of the compounds; and
   a cost of testing one or more of the compounds.

19. The method according to claim 1, wherein step (3) comprises the step of generating a function that returns an indication of an availability of one or more of the compounds.

20. The method according to claim 1, wherein step (3) comprises the step of generating a function that returns an indication of an availability of one or more reagents required to synthesize one or more of the compounds.

21. The method according to claim 1, wherein step (3) comprises the step of generating a function that returns an indication of a predicted ease of synthesis of one or more of the compounds.

22. The method according to claim 1, wherein step (3) comprises the step of generating a function that returns an indication of a predicted yield of synthesis of one or more of the compounds.

23. The method according to claim 1, wherein step (3) comprises the step of generating a function that predicts an ability of one or more of the compounds to fit a receptor binding site.

24. The method according to claim 1, wherein step (3) comprises the step of generating a function that predicts an ability of one or more of the compounds to bind selectively to a receptor binding site.

25. The method according to claim 1, wherein step (3) comprises the step of generating a function that predicts an ability of one or more of the compounds to fit a 3-dimensional receptor map model.

26. The method according to claim 1, wherein step (3) comprises the step of generating a function that predicts a bioavailability of one or more of the compounds.

27. The method according to claim 1, wherein step (3) comprises the step of generating a function that predicts a toxicity of one or more compounds.

28. The method according to claim 1, wherein step (3) comprises the step of generating a function that derives additional selection criteria from information pertaining to one or more of the compounds.

29. The method according to claim 1, wherein step (3) comprises the step of generating a function that predicts an ability of one or more of the compounds to exhibit one or more desired properties.

30. The method according to claim 1, wherein step (3) comprises the step of generating a function that predicts an ability of one or more of the compounds to test a validity of one or more structure-property models.

31. The method according to claim 1, wherein step (3) comprises the step of generating a function that predicts an ability of one or more of the compounds to discriminate between two or more structure-property models.

32. The method according to claim 1, wherein step (3) comprises the step of generating one or more functions that perform a plurality of the following functions:
   returns an indication of diversity between a plurality of the compounds;
   returns an indication of a similarity between one or more of the compounds and one or more reference compounds;
   returns an indication of a cost of one or more of the compounds;
   returns an indication of an availability of one or more of the compounds;
   returns an indication of an availability of one or more reagents required to synthesize one or more of the compounds;
   returns an indication of a predicted ease of synthesis of one or more of the compounds;
   returns an indication of a predicted yield of synthesis of one or more of the compounds;
   predicts an ability of one or more of the compounds to fit a receptor binding site;
   predicts an ability of one or more of the compounds to bind selectively to a receptor binding site;
   predicts an ability of one or more of the compounds to fit a 3-dimensional receptor map model;
   predicts a bioavailability of one or more of the compounds;
   predicts a toxicity of one or more compounds;
   derives additional selection criteria from information pertaining to one or more of the compounds;
   predicts an ability of one or more of the compounds to exhibit one or more desired properties;
   predicts an ability of one or more of the compounds to test a validity of one or more structure-property models;
   returns an indication of whether a compound is identified in a patent; and
   predicts an ability of one or more of the compounds to discriminate between two or more structure-property models.

33. The method according to claim 1, wherein said selection criteria further comprises one or more constraints for selecting the first set of compounds.

34. The method according to claim 33, wherein step (3) further comprises the step of providing a list of compounds to be excluded from the list of one or more compounds.

35. The method according to claim 33, wherein step (3) further comprises the step of providing a list of reagents that can be accommodated by a synthesizing system, whereby a compound is excluded from the list of compounds if the compound must be synthesized and if the synthesis requires a reagent not on the list of reagents.

36. The method according to claim 1, wherein step (1) comprises the step of identifying a library of chemical compounds that are one or more of:
   collectable from an in-house source;
   acquirable from an outside source; and
   synthesizable.

37. The method according to claim 1, wherein step (10) comprises one or more of the following steps:
   obtaining one or more of the compound samples from an in-house source;
   obtaining one or more of the compound samples from an outside source; and
   snythesizing one or more of the compound samples.

38. The method according to claim 1, wherein the property values for the chemical compounds include structure-property data and non-structure-property data.

39. The method according to claim 1, wherein steps (5) and (7) comprise the step of:
   (a) evaluating an extent to which a set of compounds satisfies a plurality of selection criteria.

40. The method according to claim 1, wherein at least a portion of said set of one or more selection criteria is embodied in a computer readable form, and wherein steps (5)–(9) are performed, at least partially, in a processor.

41. A computer program product comprising a computer useable medium having computer program logic stored therein to enable a computer system to select a set of chemical compounds from an electronically stored library of chemical compounds for laboratory testing, to evaluate experimentally determined structure-property data for the chemical compounds obtained from laboratory testing, and to determine whether one or more of the chemical compounds in the selected get of chemical compounds exhibit one or more properties that are similar to one or more desired properties, wherein said computer program logic comprises:
   a receiving function that receives a list of one or more desired properties that one or more target compounds shall possess and property values for chemical compounds in the library of chemical compounds;
   a selection criteria generating function that generates a set of one or more selection criteria from the from the list of one or more desired properties, said set of one or more selection criteria including one or more functions that receive property values for the one or more chemical compounds and that return one or more selection criteria values, whereby said selection criteria values indicate extents to which the one or more chemical compounds meet the set of one or more selection criteria;
   a compound selection function that:
      picks one or more initial sets of chemical compounds from the library of chemical compounds, each said one or more initial sets of chemical compounds including a plurality of chemical compounds, wherein a plurality of said one or more initial sets of chemical compounds are not identical to one another,
      uses the selection criteria and the property values for the one or more chemical compounds in the one or more initial sets of chemical compounds to calculate selection criteria values for the one or more initial sets of chemical compounds, whereby the selection criteria values indicate extents to which the one or more initial sets of chemical compounds meet the set of one or more selection criteria,
      picks one or more new sets of chemical compounds from the library of chemical compounds, each said one or more new sets of chemical compounds including a plurality of chemical compounds, wherein a plurality of said one or more new sets of chemical compounds are not identical to one another and wherein at least one of said one or more new sets of chemical compounds are not identical to at least one of said one or more initial sets of chemical compounds,
      uses the selection criteria and the property values for the one or more chemical compounds in the one or more new sets of chemical compounds to calculate selection criteria values for the one or more new sets of chemical compounds, whereby the selection criteria values indicate extents to which the one or more new sets of chemical compounds meet the set of one or more selection criteria, and
      selects a first set of compounds from the one or more initial sets of compounds and the one or more new sets of chemical compounds, based on a comparison of the respective selection criteria values; and
   a chemical compound analysis function that receives experimentally determined structure-property data for the first set of compounds and that determines from at least the actual structure-property data of the first set of chemical compounds, whether any of the chemical compounds in the first set of chemical compounds exhibit one or more properties that are similar to one or more of the desired properties that one or more target chemical compounds shall possess.

42. A system for identifying one or more target chemical compounds having desired properties, comprising:
   means for identifying an electronically stored library of chemical compounds;
   means for receiving a list of one or more desired properties that the one or more target chemical compounds shall possess;
   means for generating a set of one or more selection criteria from the list of one or more desired properties, wherein said set of one or more selection criteria include one or more functions that receive property values for the one or more chemical compounds and that return one or more selection criteria values for the one or more chemical compounds;
   means for picking one or more initial sets of chemical compounds from the library of chemical compounds, each said one or more initial sets of chemical compounds including a plurality of chemical compounds, wherein a plurality of said one or more initial sets of chemical compounds are not identical to one another;
   means for using the selection criteria and the property values for the one or more chemical compounds in the one or more initial sets of chemical compounds to calculate selection criteria values for the one or more initial sets of chemical compounds, whereby the selection criteria values indicate an extent to which the one or more initial sets of chemical compounds meet the set of one or more selection criteria;
   means for picking one or more new sets of chemical compounds from the library of chemical compounds, each said one or more new sets of chemical compounds including a plurality of chemical compounds, wherein a plurality of said one or more new sets of chemical compounds are not identical to one another and wherein at least one of said one or more new sets of chemical compounds are not identical to at least one of said one or more initial sets of chemical compounds;
   means for using the selection criteria and the property values for the one or more chemical compounds in the one or more new sets of chemical compounds to calculate selection criteria values for the one or more new sets of chemical compounds, whereby the selection criteria values indicate an extent to which the one or more new sets of chemical compounds meet the set of one or more selection criteria;
   means for selecting a first set of chemical compounds from the one or more initial sets of chemical compounds and the one or more new sets of chemical compounds, based on a comparison of the respective selection criteria values;
   means for obtaining physical samples of the first set of chemical compounds;

means for experimentally determining structure-property data from physical samples of the first set of chemical compounds; and means for determining, from at least the experimentally determined structure-property data of the first set of chemical compounds, whether any of the chemical compounds in the first set of chemical compounds exhibit one or more properties that are similar to one or more of the desired properties that one or more target chemical compounds shall possess.

* * * * *

UNITED STATES PATENT AND TRADEMARK OFFICE
CERTIFICATE OF CORRECTION

PATENT NO. : 6,421,612 B1
DATED : July 16, 2002
INVENTOR(S) : Agrafiotis et al.

It is certified that error appears in the above-identified patent and that said Letters Patent is hereby corrected as shown below:

Title page,
Item [56], References Cited, FOREIGN PATENT DOCUMENTS, please add the following citations:

-- WO 94/28504
  WO 95/0106
  WO 97/27559
  WO 98/20459 --

Column 51,
Line 45, please replace "least on of" with -- least one of --.

Column 54,
Line 64, please replace "snythesizing" with -- synthesizing --.

Column 55,
Line 17, please replace "get" with -- set --.
Line 26, please delete the second occurrence of "from the".

Signed and Sealed this

Fourth Day of March, 2003

JAMES E. ROGAN
*Director of the United States Patent and Trademark Office*